United States Patent
Zheng et al.

(10) Patent No.: US 12,252,554 B2
(45) Date of Patent: Mar. 18, 2025

(54) ANALOGS THAT TARGET MITOCHONDRIAL DISEASES

(71) Applicant: Stealth BioTherapeutics Inc., Needham, MA (US)

(72) Inventors: Guozhu Zheng, Lexington, MA (US); Mark J. Bamberger, South Glastonbury, CT (US); Inese Smukste, Weston, MA (US)

(73) Assignee: Stealth BioTherapeutics Inc., Needham, MA (US)

( * ) Notice: Subject to any disclaimer, the term of this patent is extended or adjusted under 35 U.S.C. 154(b) by 723 days.

(21) Appl. No.: 17/414,168

(22) PCT Filed: Nov. 19, 2019

(86) PCT No.: PCT/US2019/062284
§ 371 (c)(1),
(2) Date: Jun. 15, 2021

(87) PCT Pub. No.: WO2020/131283
PCT Pub. Date: Jun. 25, 2020

(65) Prior Publication Data
US 2022/0041654 A1 Feb. 10, 2022

Related U.S. Application Data

(60) Provisional application No. 62/781,156, filed on Dec. 18, 2018.

(51) Int. Cl.
*A61K 38/00* (2006.01)
*C07K 5/11* (2006.01)
*C07K 5/117* (2006.01)

(52) U.S. Cl.
CPC .......... *C07K 5/1019* (2013.01); *C07K 5/1024* (2013.01); *A61K 38/00* (2013.01)

(58) Field of Classification Search
None
See application file for complete search history.

(56) References Cited

U.S. PATENT DOCUMENTS

| 8,697,657 B2 | 4/2014 | Wilson |
| 11,325,943 B2 | 5/2022 | Duncan |
| 2012/0329730 A1* | 12/2012 | Szeto ............ A61P 43/00 514/21.7 |
| 2014/0093897 A1 | 4/2014 | Szeto et al. |
| 2016/0151446 A1 | 6/2016 | Wilson |
| 2022/0041653 A1 | 2/2022 | Zheng et al. |

FOREIGN PATENT DOCUMENTS

| WO | WO-2011/091357 A1 | 7/2011 |
| WO | WO-2012/006569 A1 | 1/2012 |
| WO | WO-2014/134554 A1 | 9/2014 |
| WO | WO-2015/134096 A1 | 9/2015 |
| WO | WO-2015/183984 A2 | 12/2015 |
| WO | WO-2016/144352 A2 | 9/2016 |
| WO | WO-2017/093897 A1 | 6/2017 |
| WO | WO-2017/117381 A1 | 7/2017 |
| WO | WO-2017/180535 A1 | 10/2017 |
| WO | WO-2017/201433 A1 | 11/2017 |
| WO | WO-2019/099481 A1 | 5/2019 |
| WO | WO-2020/131283 A1 | 6/2020 |

OTHER PUBLICATIONS

International Search Report and Written Opinion for International Application No. PCT/US2019/062284 mailed Mar. 16, 2020.
Cerrato et al., "Novel Cell and 8208; penetrating peptide targeting mitochondira", The Faseb Journal, 29(11): 4589-4599 (2015).
Extended European Search Report for EP Application No. 19900766.7 dated Jul. 21, 2022.

* cited by examiner

*Primary Examiner* — Thomas S Heard
(74) *Attorney, Agent, or Firm* — Foley Hoag LLP; Dana M. Gordon; Hilary Dorr Lang

(57) ABSTRACT

Disclosed are analogs of elamipretide (MTP-131). The compounds are useful for the treatment and prevention of ischemia-reperfusion injury (e.g., cardiac ischemia-reperfusion injury) or myocardial infarction.

25 Claims, 2 Drawing Sheets

Figure 1

| CAS No. | Vendor (Catalog No.) or Literature Citation | Structure |
|---|---|---|
| 96539-87-6 | Aldrich (38473) | 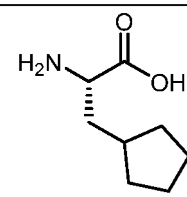 |
| 155760-02-4 | QM Bio (8253011) | 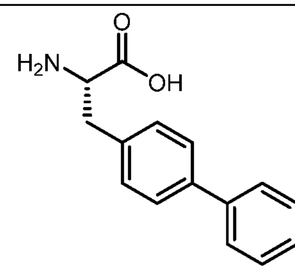 |
| 2935-35-5 | Alfa Aesar (30314) | 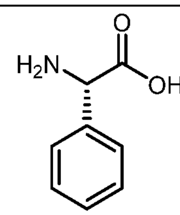 |
| 95975-81-8 | Do, et al. Helvetica, 1979, V. 62, No. 4, 956-964. | 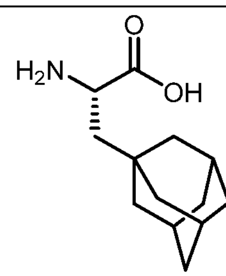 |

Figure 2

| CAS No. | Vendor (Catalog No.) or Literature Citation | Structure |
|---|---|---|
| 81806-45-3 | e-Novation Chemicals (D111000) | 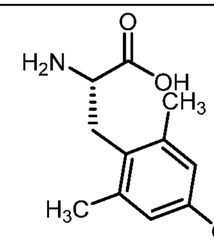 |
| 1482-98-0 | Aldrich (19589) | 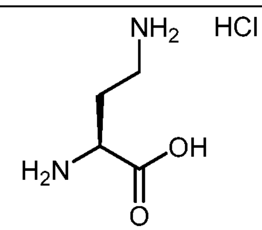 |
| 119434-75-2 | Aldrich (670553) | 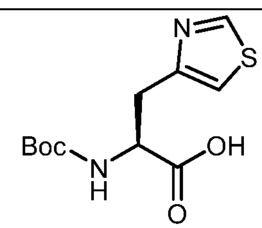 |
| 70702-47-5 | Alfa Aesar (H63132) | 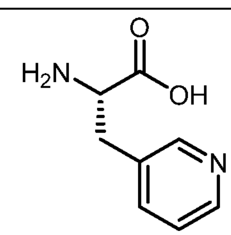 |

ANALOGS THAT TARGET MITOCHONDRIAL DISEASES

RELATED APPLICATIONS

This application is a U.S. National Stage Application of International Application No. PCT/US19/62284, filed Nov. 19, 2019; which claims the benefit of priority to U.S. Provisional Patent Application No. 62/781,156, filed Dec. 18, 2018.

BACKGROUND OF THE INVENTION

Elamipretide (MTP-131) is a mitochondria-targeting peptide compound with therapeutic potential for treating diseases associated with mitochondrial dysfunction. Because of the potential therapeutic applications of elamipretide (MTP-131), there exists a need to develop analogs of these compounds that have an improved therapeutic profile.

SUMMARY OF THE INVENTION

An aspect of the invention is an analog of elamipretide (MTP-131).

More specifically, the invention provides a compound of formula (I), or a pharmaceutically acceptable salt thereof:

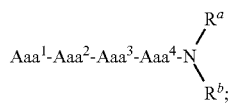

wherein:

$Aaa^1$ is an amino acid residue selected from the group consisting of:

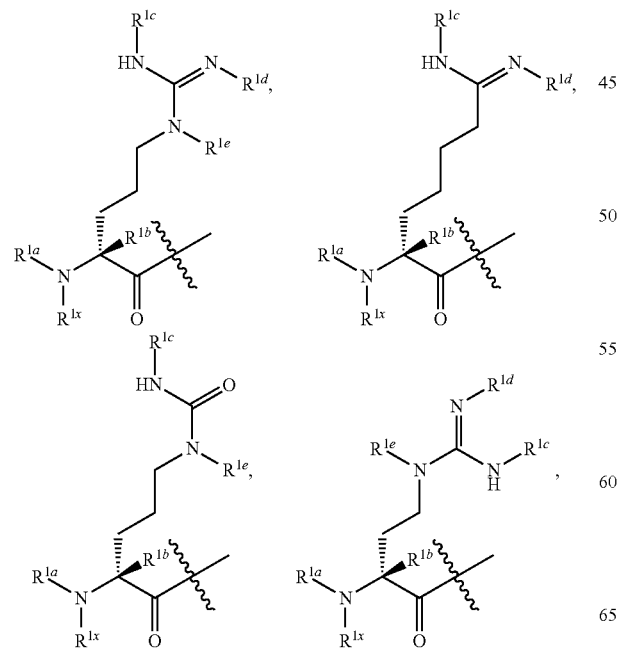

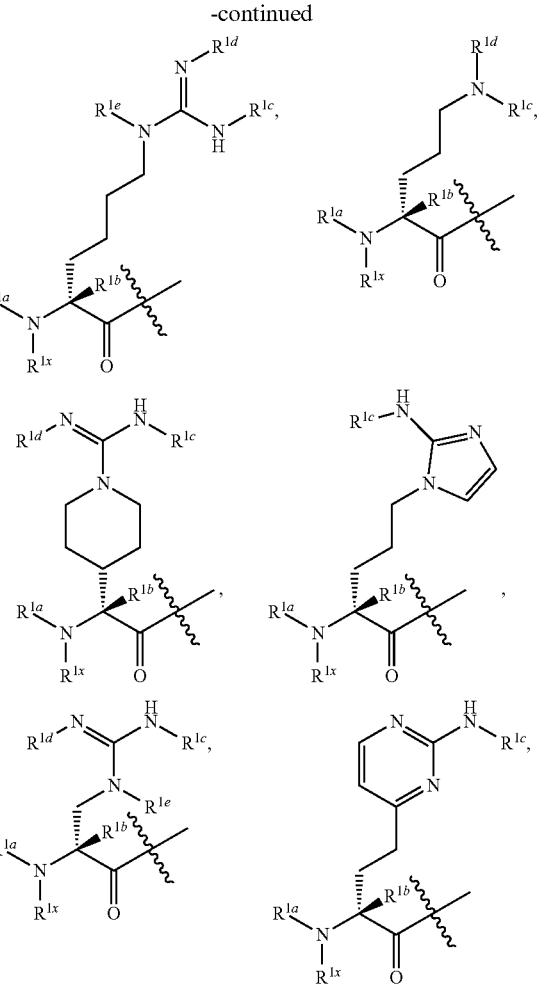

$Aaa^2$ is an amino acid residue selected from the group consisting of:

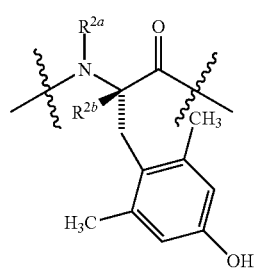

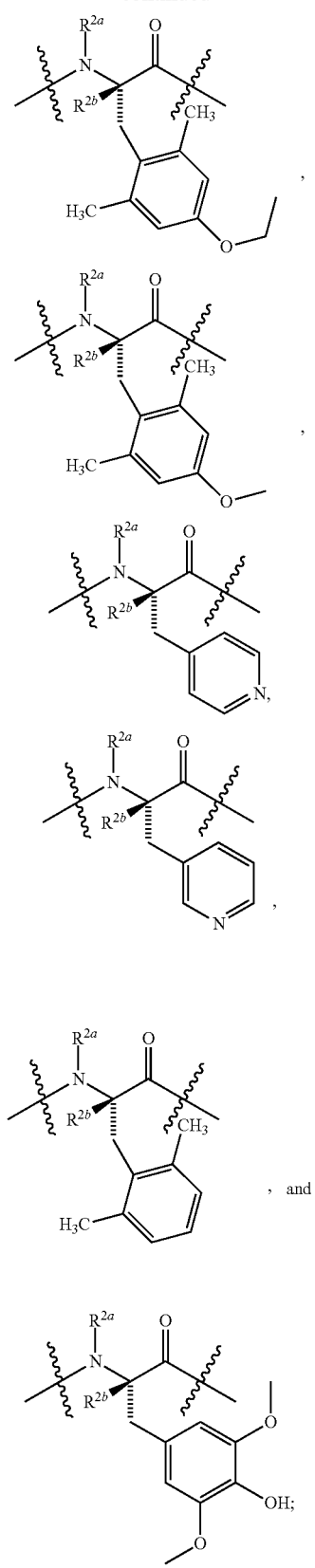
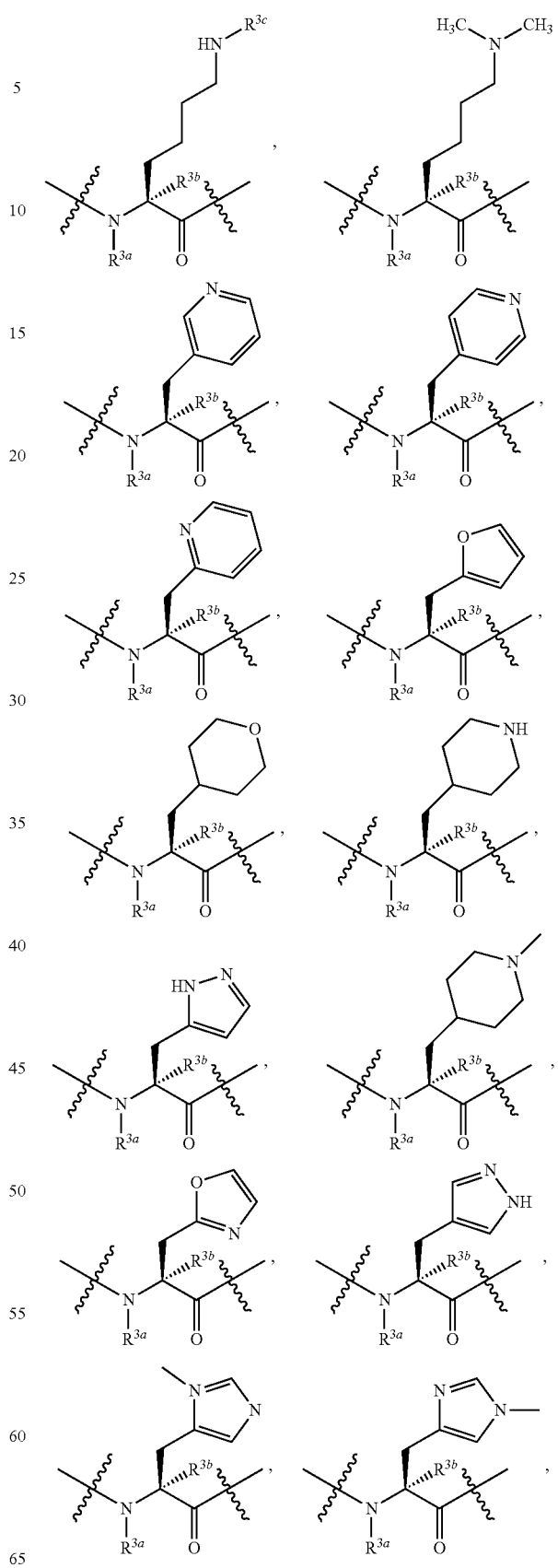
Aaa[3] is an amino acid residue selected from the group consisting of:

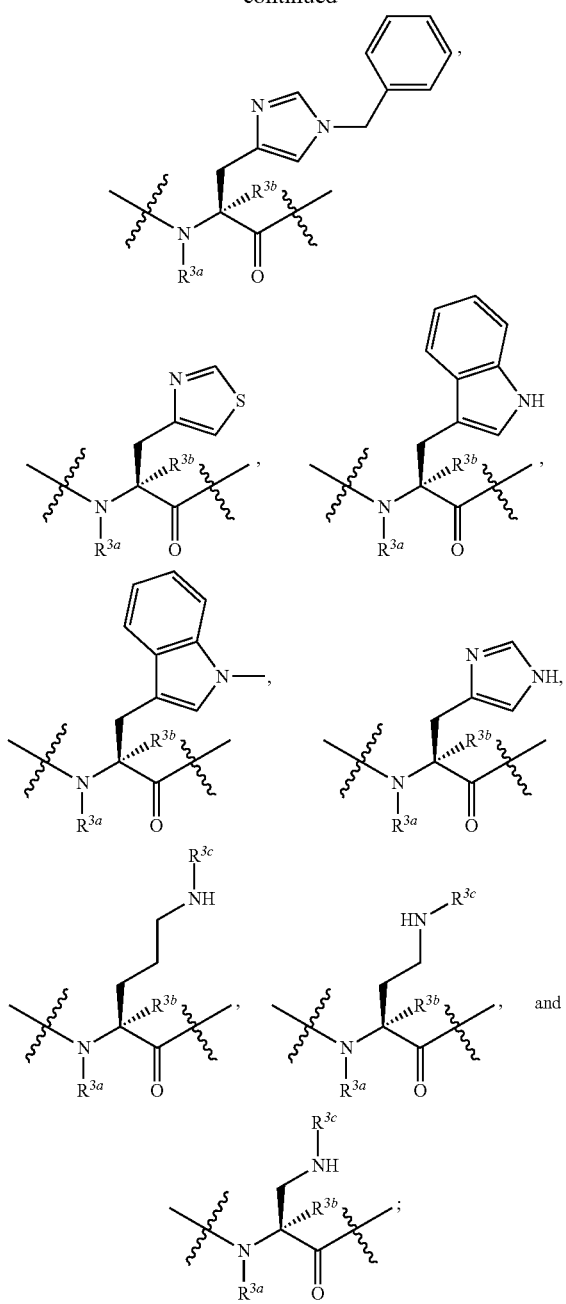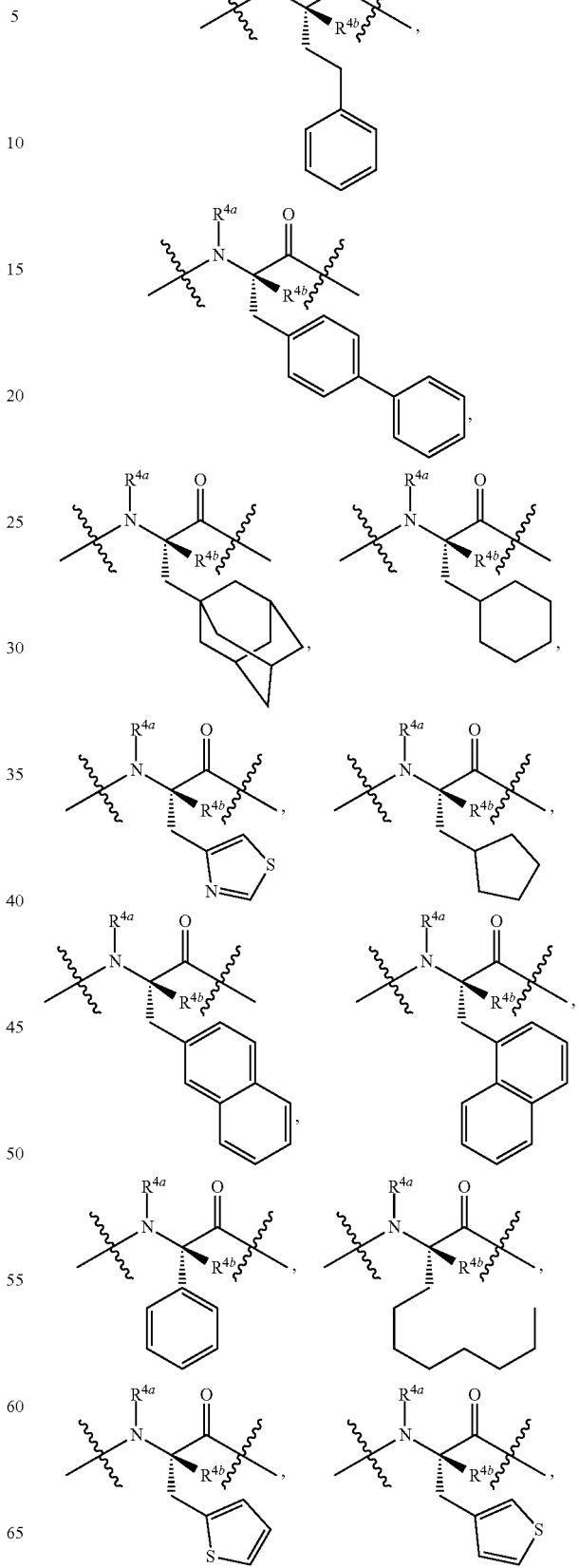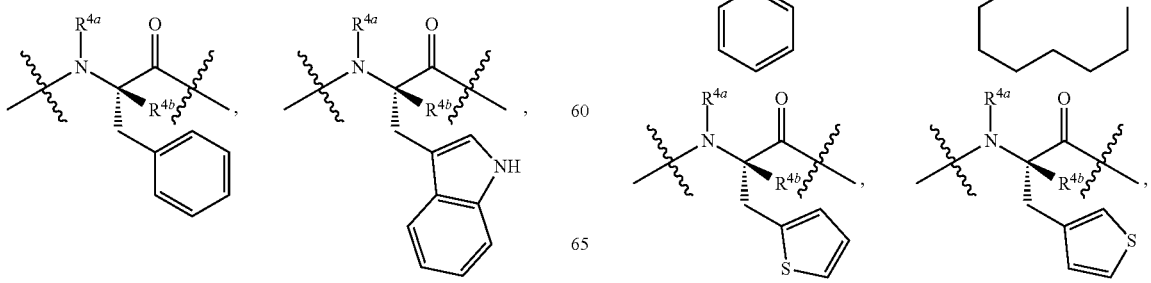

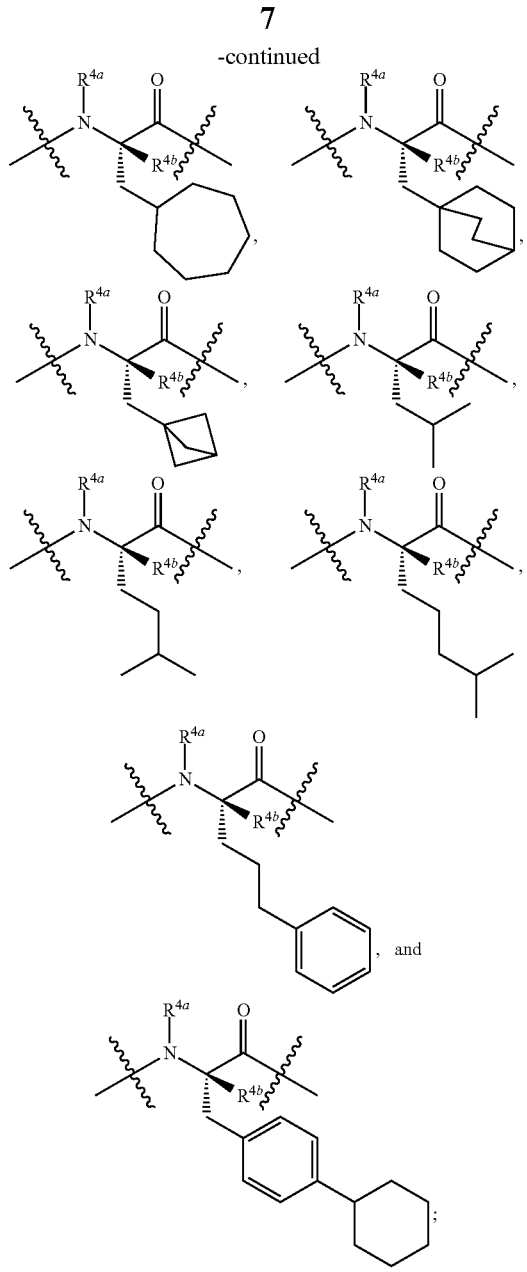

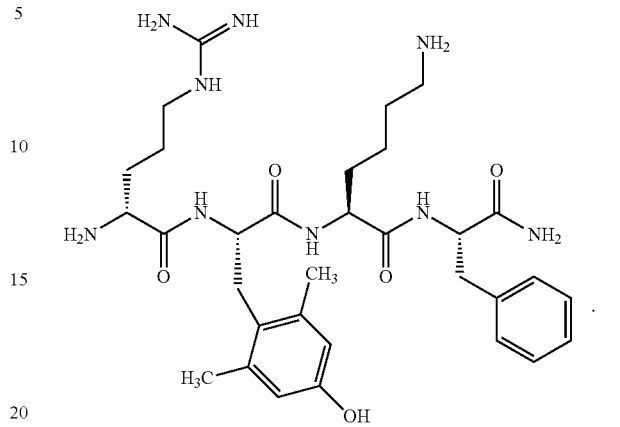

$R^{1a}, R^{1b}, R^{1e}, R^{1x}, R^{2a}, R^{2b}, R^{3a}, R^{3b}, R^{3c}, R^{4a},$ and $R^{4b}$ are each independently selected from the group consisting of H, methyl, ethyl, propyl, cyclopropyl, cyclobutyl, and $(C_1-C_6)$alkyl; or $R^{1a}$ and $R^{1x}$ together with the N atom to which they are attached form a 4-6-membered heterocyclyl; and $R^a, R^b, R^{1c}$ and $R^{1d}$ are each independently selected from the group consisting of H, methyl, ethyl, propyl, cyclopropyl, cyclobutyl, $(C_1-C_6)$alkyl, $C(O)((C_1-C_6)$alkyl), $C(O)((C_1-C_6)$haloalkyl), $C(O)O((C_1-C_6)$alkyl), and $C(O)O(aryl(C_1-C_6)$alkyl); or $R^a$ and $R^b$ together with the N atom to which they are attached form a 4-6-membered heterocyclyl;

provided that the compound of formula (I) is not (MTP-131)

Another aspect of the invention is a pharmaceutical composition, comprising a compound of the invention; and a pharmaceutically acceptable carrier.

The invention also provides methods of treating or preventing ischemia-reperfusion injury, comprising administering to a subject in need thereof a therapeutically effective amount of a compound of the invention.

The invention also provides methods of treating or preventing myocardial infarction, comprising administering to a subject in need thereof a therapeutically effective amount of a compound of the invention.

BRIEF DESCRIPTION OF THE DRAWINGS

FIG. 1 depicts various amino acid residues useful in the present invention.

FIG. 2 depicts various amino acid residues useful in the present invention.

DETAILED DESCRIPTION OF THE INVENTION

Elamipretide (MTP-131; D-Arg-DMT-Lys-Phe-NH$_2$, wherein DMT is 2,6-dimethyl-L-Tyr) is a mitochondria-targeting compound with therapeutic potential for treating ischemia-reperfusion injury (e.g., cardiac ischemia-reperfusion injury), and myocardial infarction. Analogs of this compound may have improved therapeutic profiles, including improved metabolic properties, selectivity, or potency.

Accordingly, in certain embodiments, the invention provides a compound of formula (I), or a pharmaceutically acceptable salt thereof:

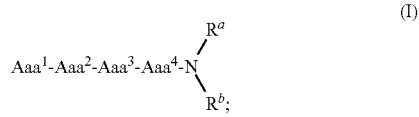

wherein:

Aaa$^1$ is an amino acid residue selected from the group consisting of:

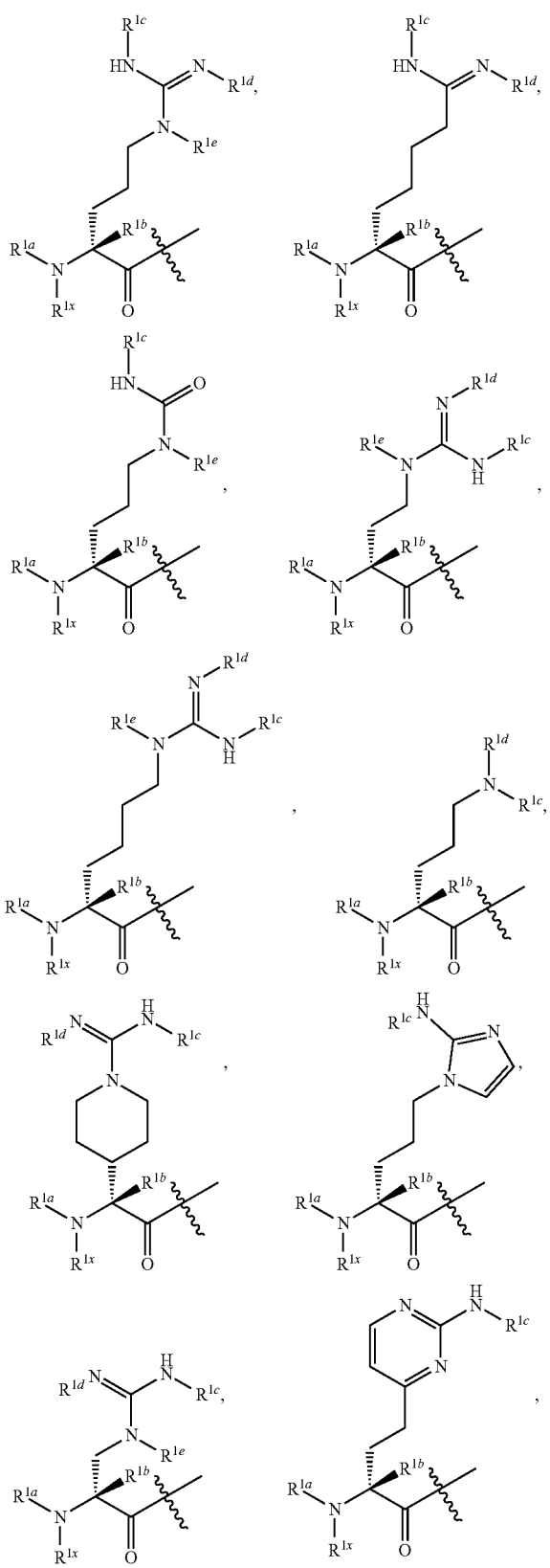
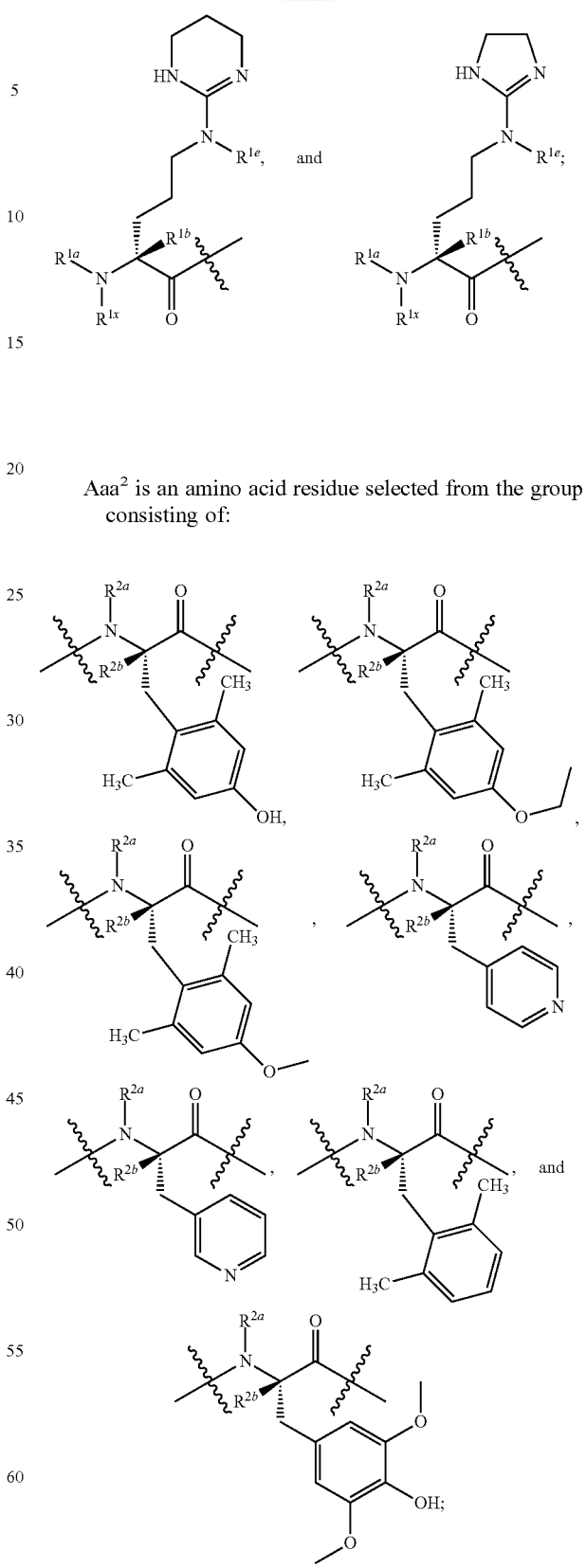
Aaa² is an amino acid residue selected from the group consisting of:
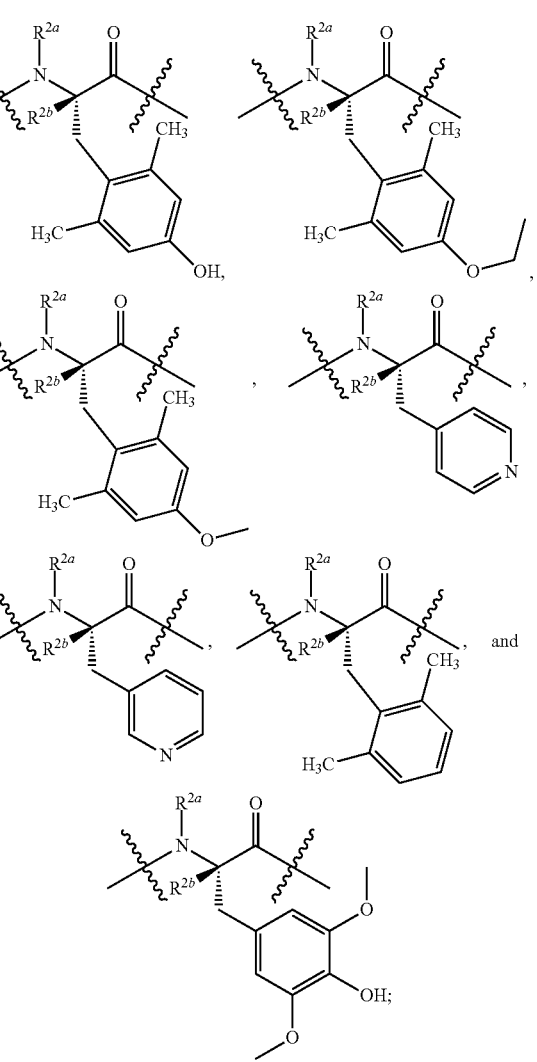
Aaa³ is an amino acid residue selected from the group consisting of:

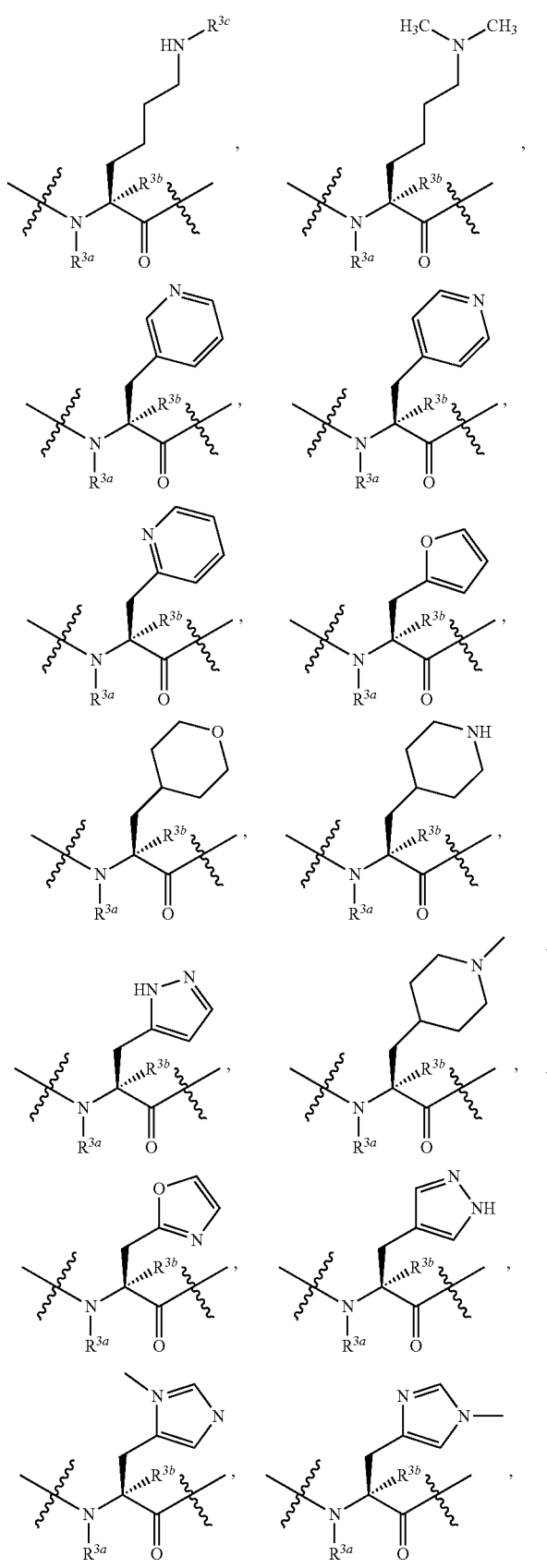
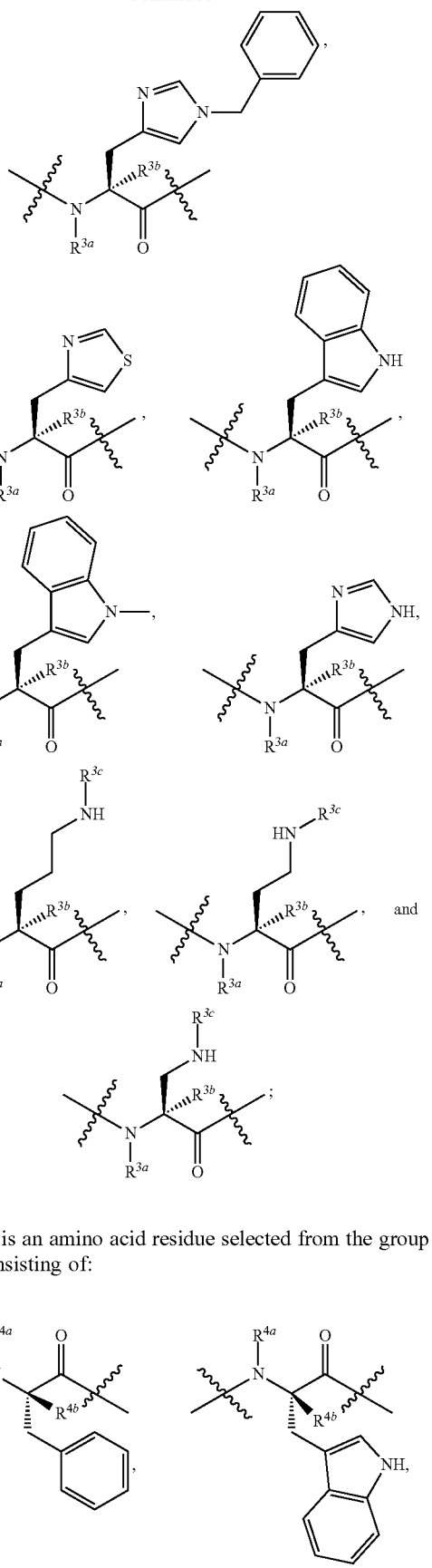
-continued
Aaa⁴ is an amino acid residue selected from the group consisting of:

-continued

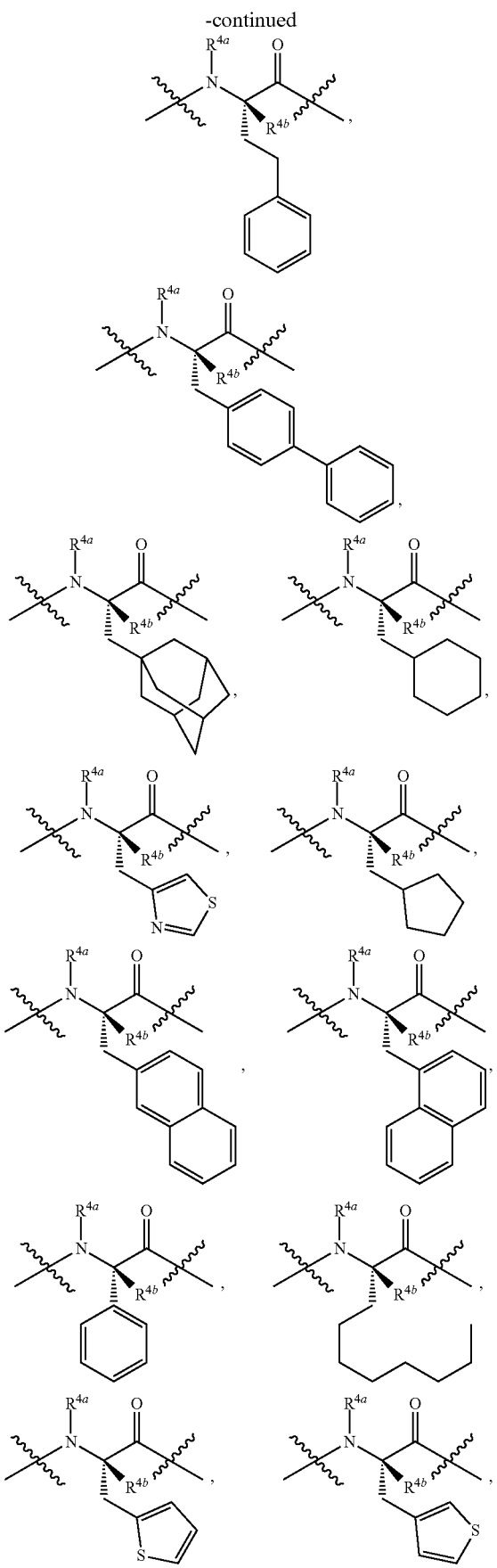

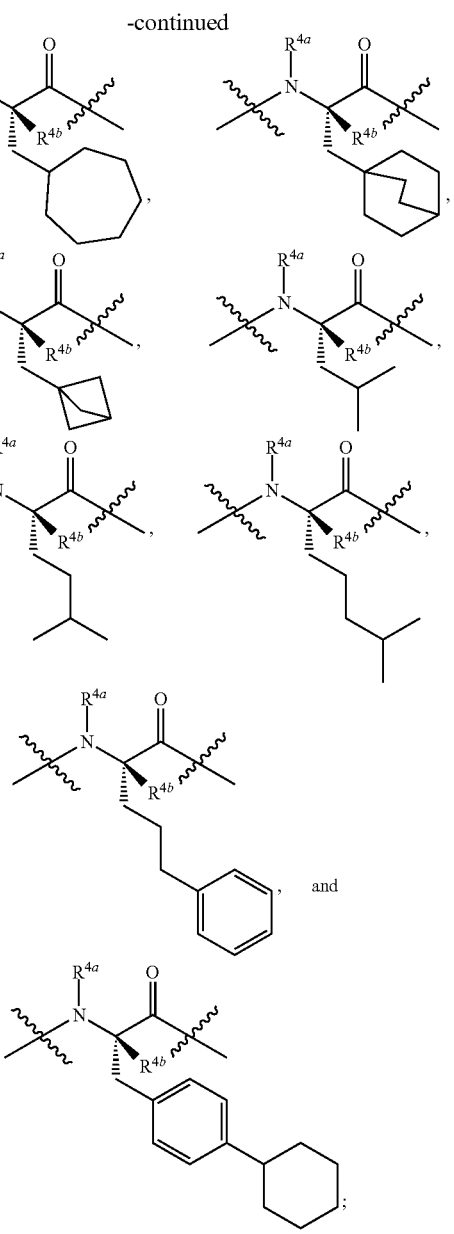

and $R^{1a}$, $R^{1b}$, $R^{1e}$, $R^{1x}$, $R^{2a}$, $R^{2b}$, $R^{3a}$, $R^{3b}$, $R^{3c}$, $R^{4a}$, and $R^{4b}$ are each independently selected from the group consisting of H, methyl, ethyl, propyl, cyclopropyl, cyclobutyl, and $(C_1\text{-}C_6)$alkyl; or $R^{1a}$ and $R^{1x}$ together with the N atom to which they are attached form a 4-6-membered heterocyclyl; and $R^a$, $R^b$, $R^{1c}$ and $R^{1d}$ are each independently selected from the group consisting of H, methyl, ethyl, propyl, cyclopropyl, cyclobutyl, $(C_1\text{-}C_6)$alkyl, C(O)$((C_1\text{-}C_6)$alkyl), C(O)$((C_1\text{-}C_6)$haloalkyl), C(O)O$((C_1\text{-}C_6)$alkyl), and C(O)O(aryl$(C_1\text{-}C_6)$alkyl); or $R^a$ and $R^b$ together with the N atom to which they are attached form a 4-6-membered heterocyclyl;

provided that the compound of formula (I) is not

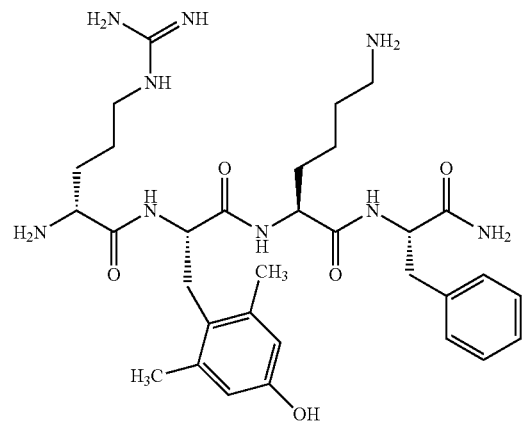

In certain embodiments, $R^{1a}$ and $R^{1x}$ are independently H, methyl, ethyl, propyl, cyclopropyl, or cyclobutyl; or $R^{1a}$ and $R^{1x}$ together with the N atom to which they are attached form a 4-6-membered heterocyclyl.

In certain embodiments, $Aaa^1$ is selected from the group consisting of

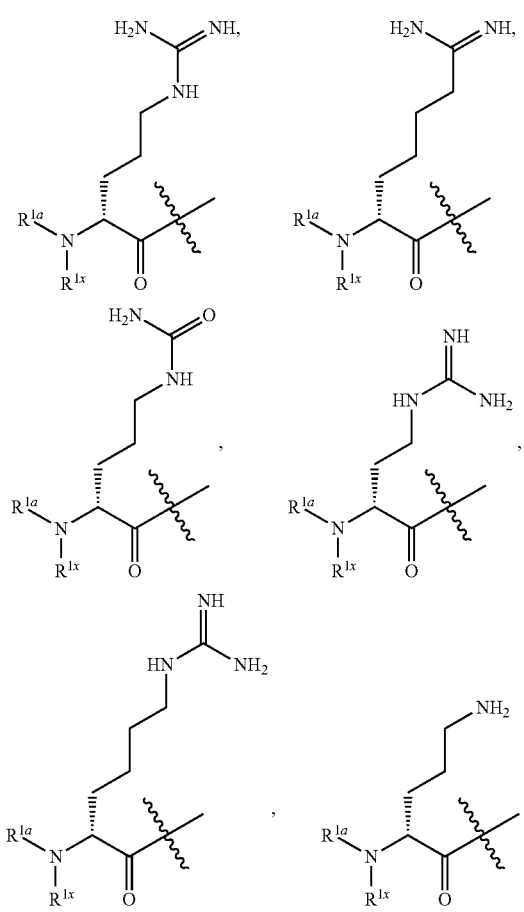

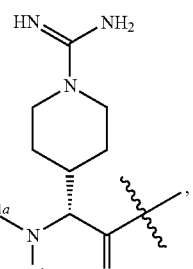

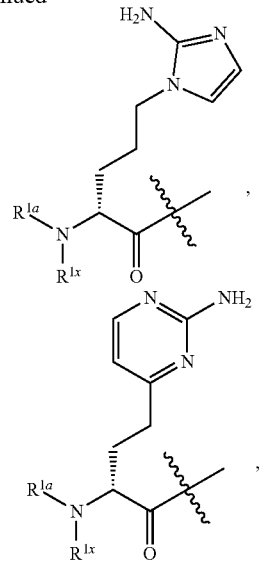

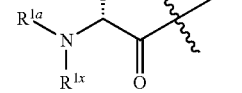

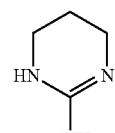

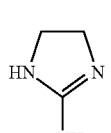

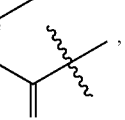

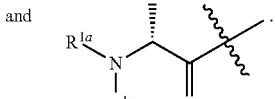

In further embodiments, $Aaa^1$ is

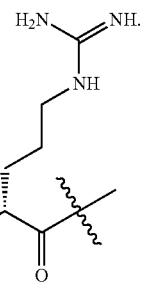

Alternatively, in certain embodiments, $Aaa^1$ is an amino acid residue selected from the group consisting of:

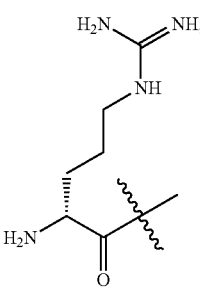 [SMILES: *C(=O)[C@H](N)CCCNC(=N)N]

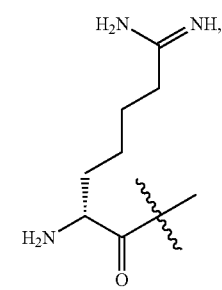

-continued
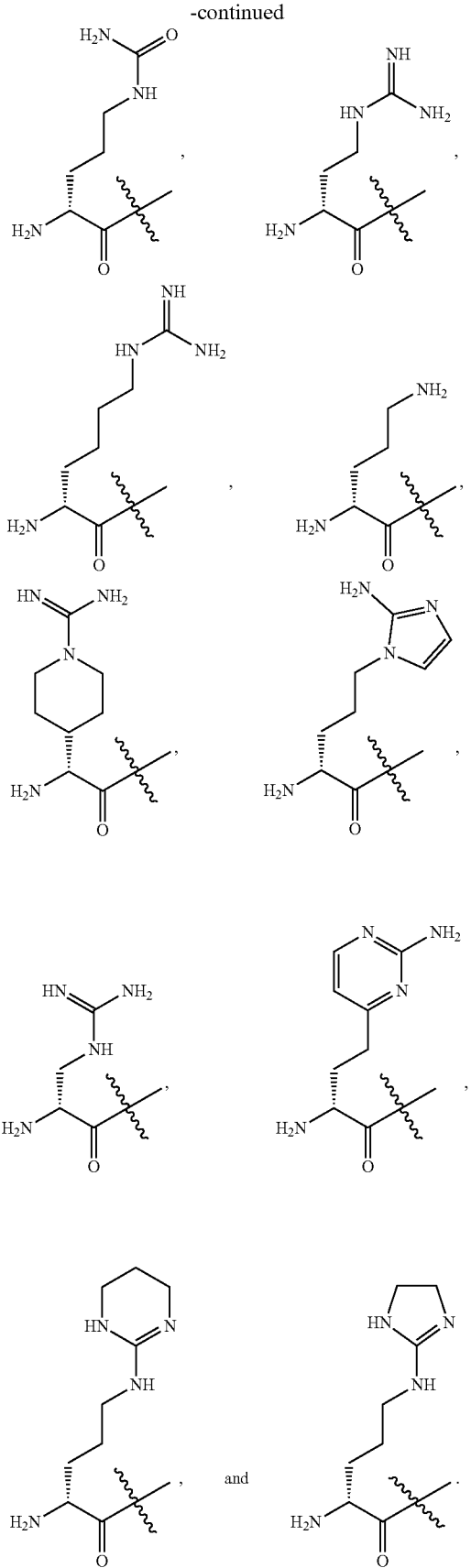
In some embodiments, Aaa$^1$ is
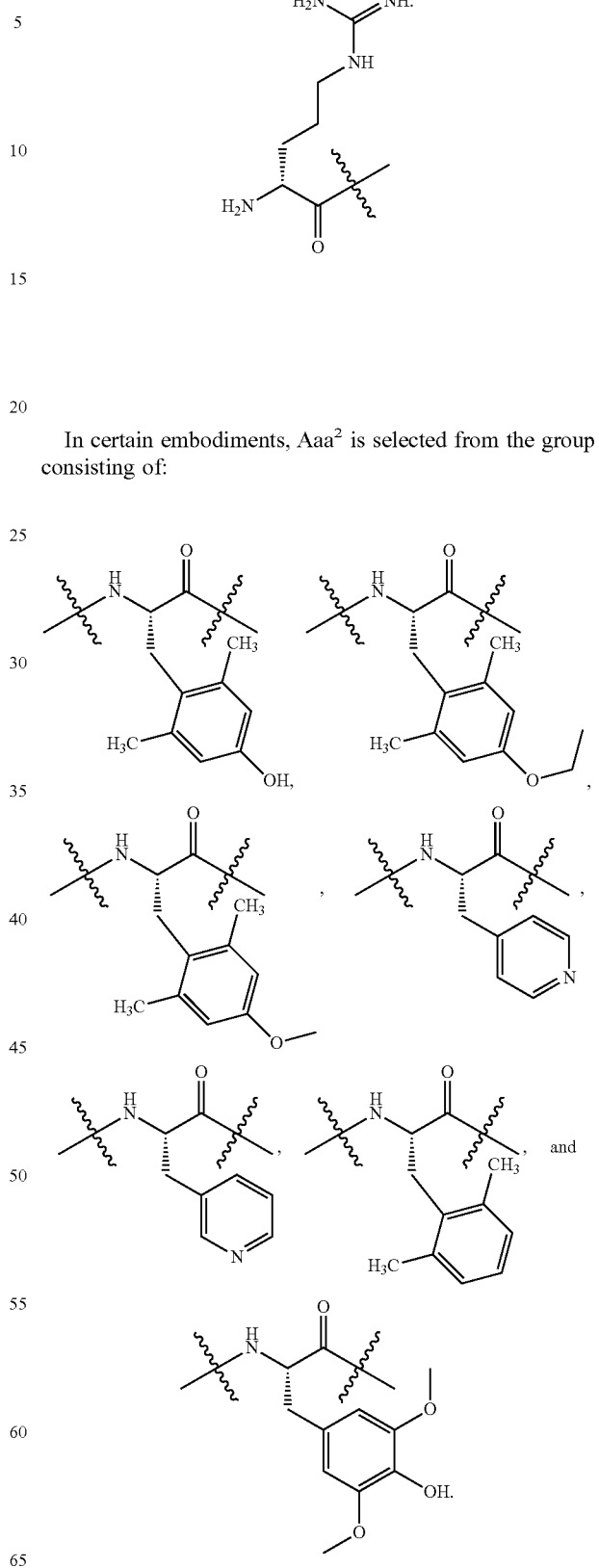
In certain embodiments, Aaa$^2$ is selected from the group consisting of:

In certain embodiments, Aaa² is
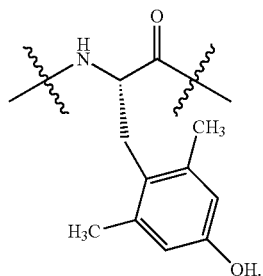 [SMILES: *N[C@@H](Cc1c(C)cc(O)cc1C)C(*)=O]
In certain embodiments, $R^{3b}$ is H or methyl.
In some embodiments, Aaa³ is selected from the group consisting of:
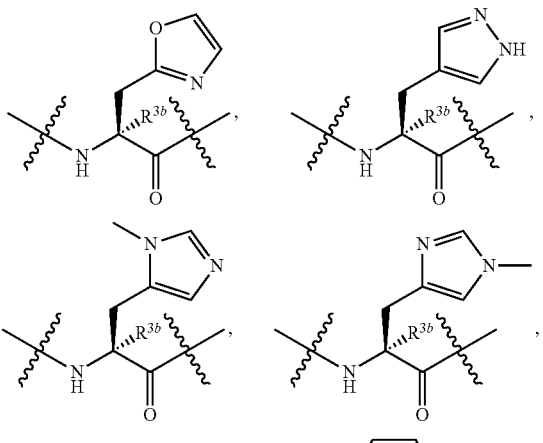
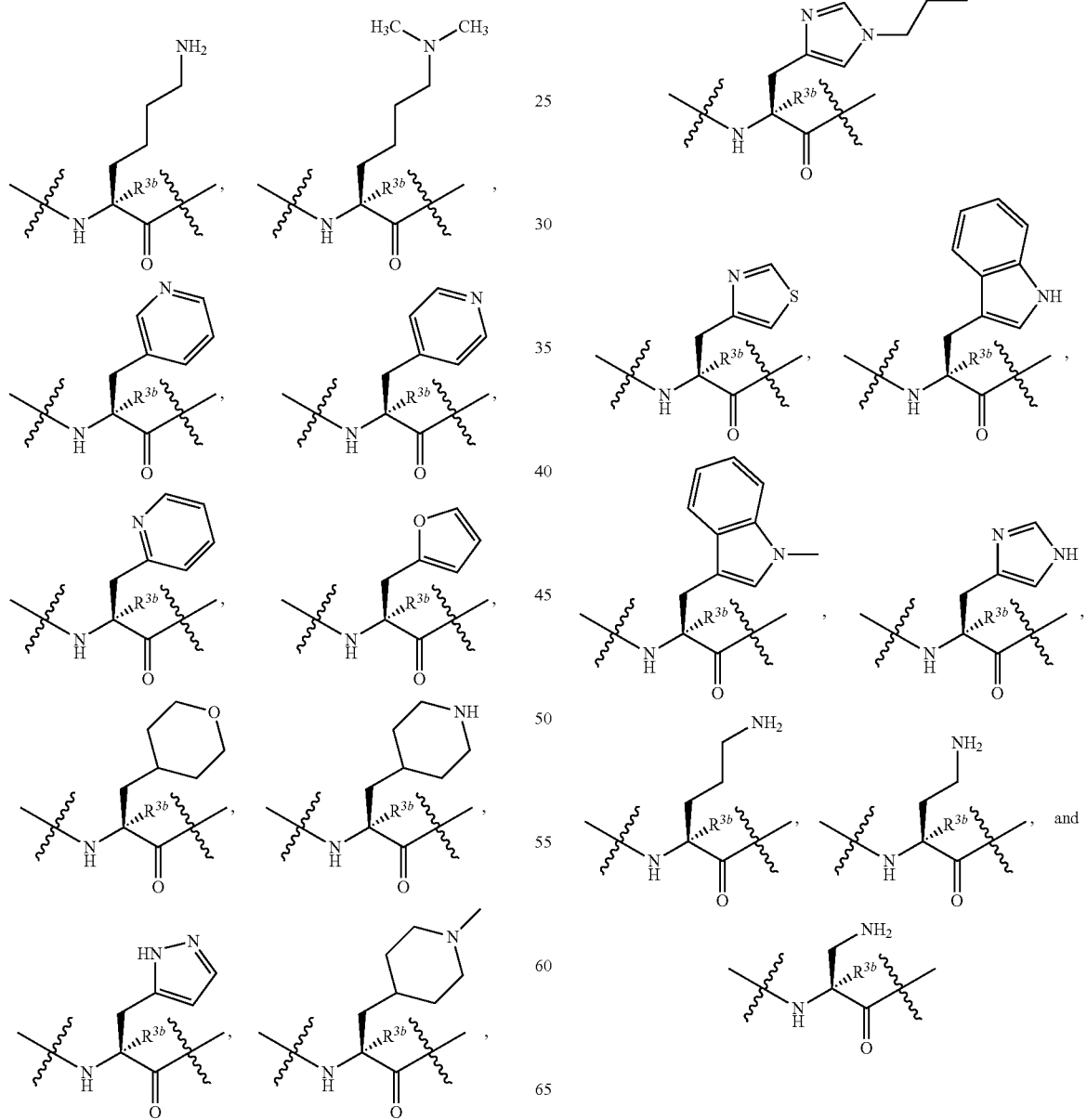

For example, Aaa³ may be
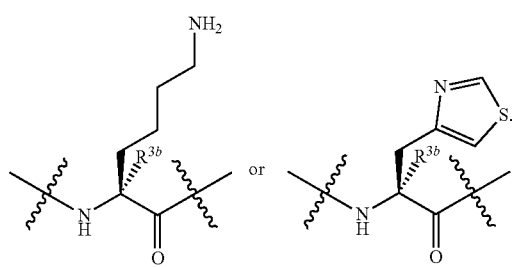
Alternatively, in some embodiments, Aaa³ is selected from the group consisting of:
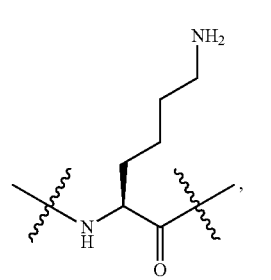
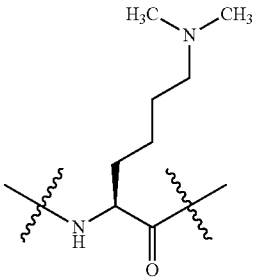
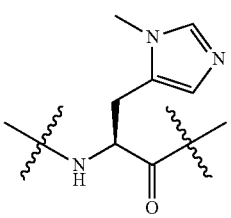
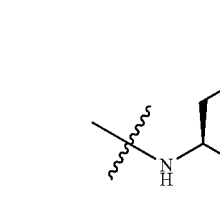
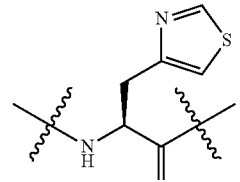
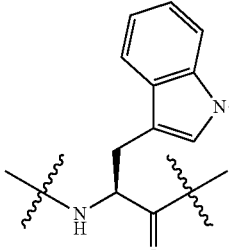
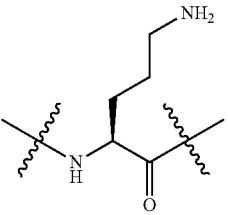
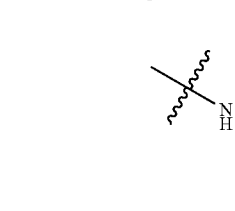
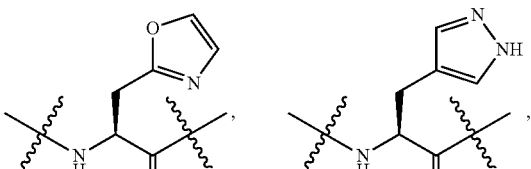
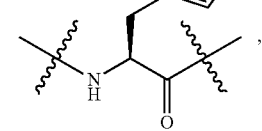
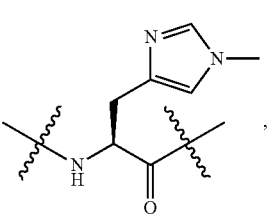
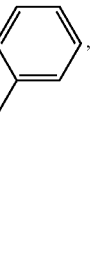
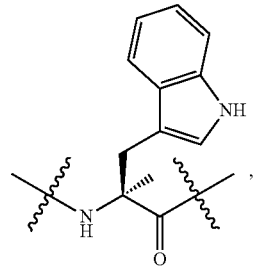
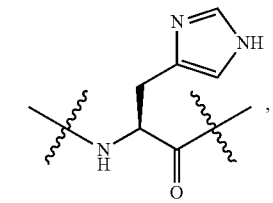
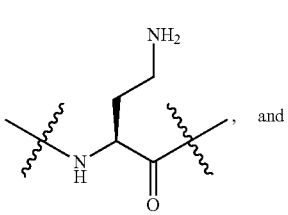
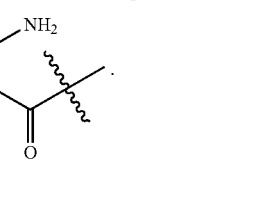

In certain embodiments, Aaa³ is
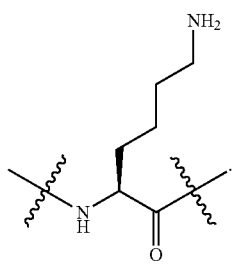
In certain embodiments, $R^{4a}$ and $R^{4b}$ are each independently H or methyl.
In certain embodiments, Aaa⁴ is
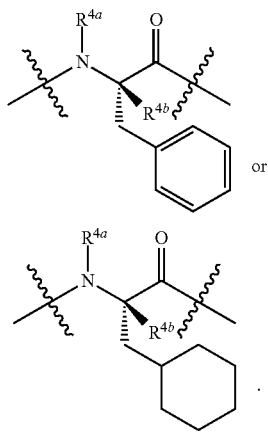
Alternatively, in some embodiments, Aaa⁴ is selected from the group consisting of:
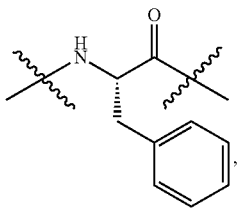 , 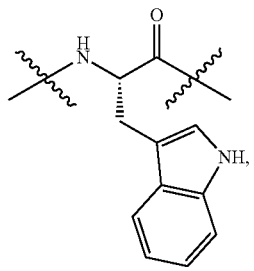 ,
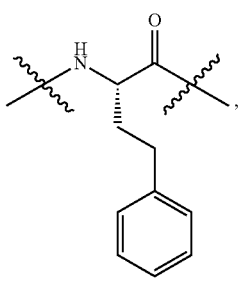 ,
-continued
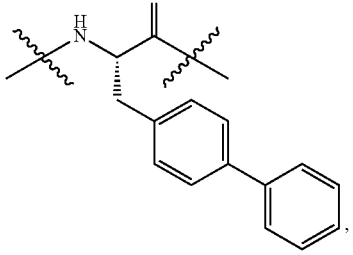 ,
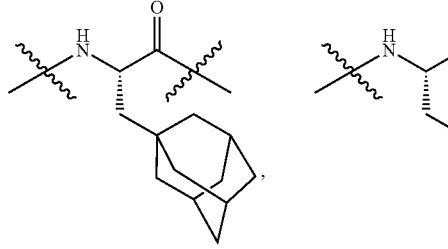
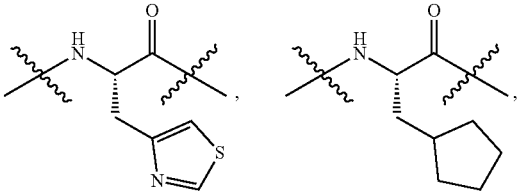
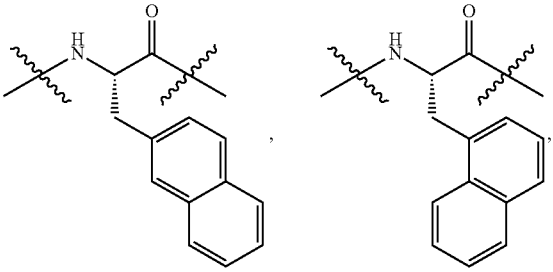
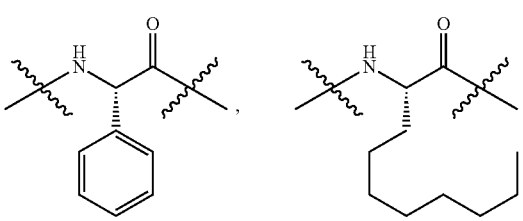
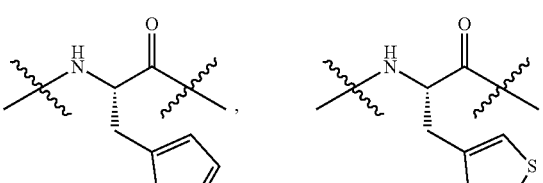
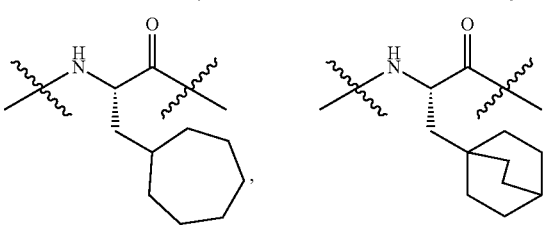

-continued
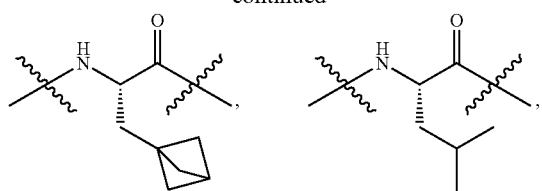
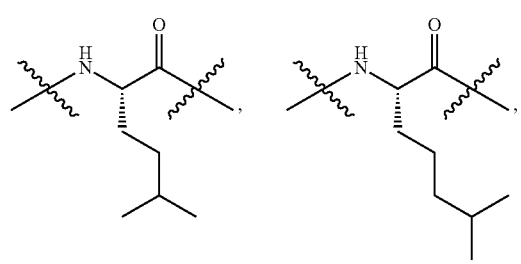
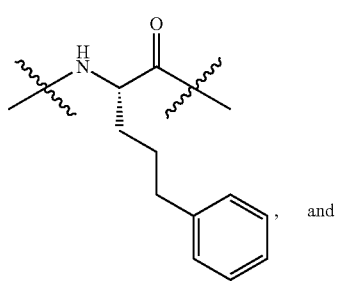
, and
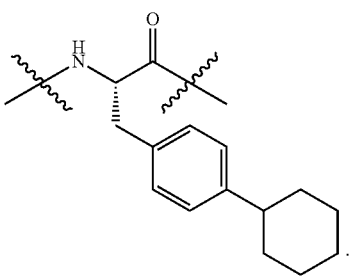
In certain embodiments, Aaa[4] is
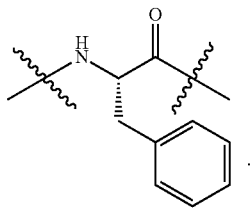 [SMILES: *N[C@@H](Cc1ccccc1)C(*)=O]
In certain embodiments, $R^a$ and $R^b$ are each independently H or methyl, preferably H.
In certain embodiments, the compound of formula (I) is selected from the following table:
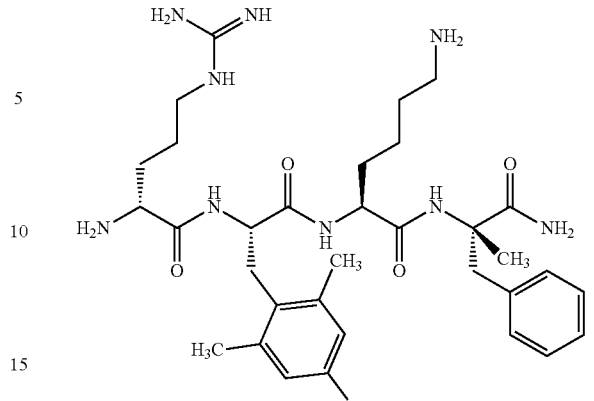
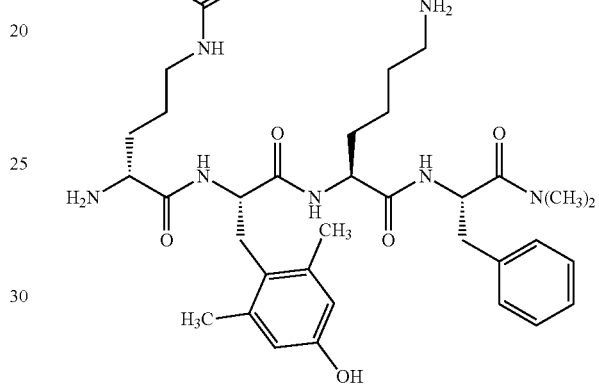
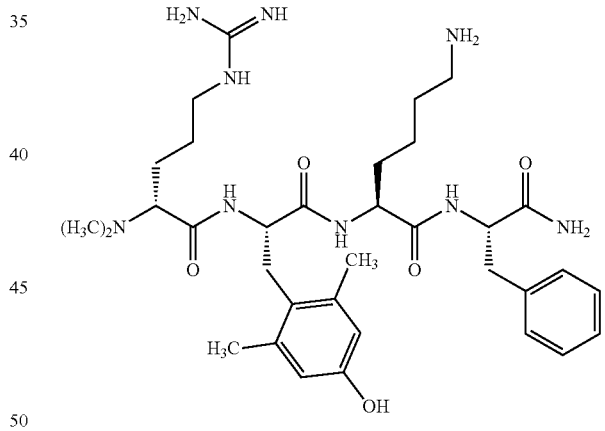
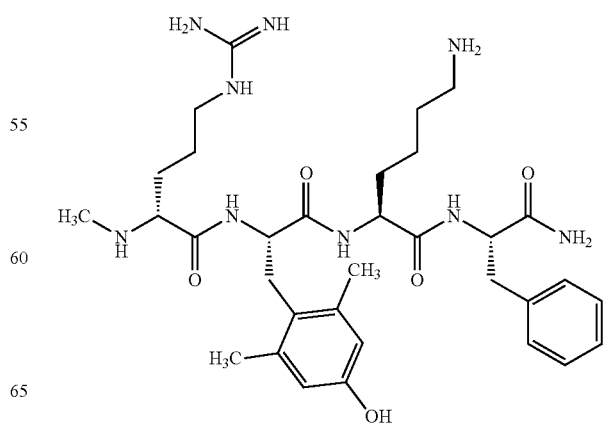

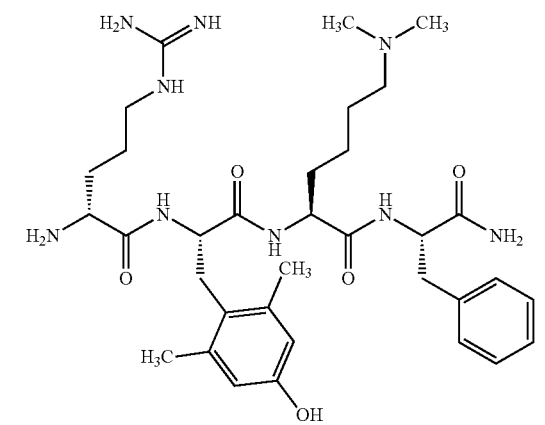 [SMILES: Cc1cc(O)cc(C)c1C[C@H](NC(=O)[C@H](N)CCCNC(=N)N)C(=O)N[C@@H](CCCCN(C)C)C(=O)N[C@@H](Cc1ccccc1)C(N)=O]
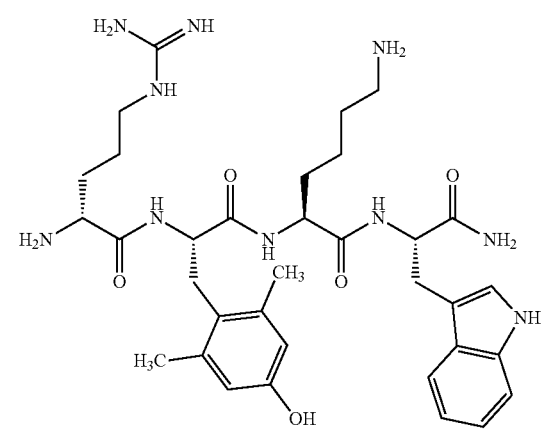 [SMILES: Cc1cc(O)cc(C)c1C[C@H](NC(=O)[C@H](N)CCCNC(=N)N)C(=O)N[C@@H](CCCCN)C(=O)N[C@@H](Cc1c[nH]c2ccccc12)C(N)=O]
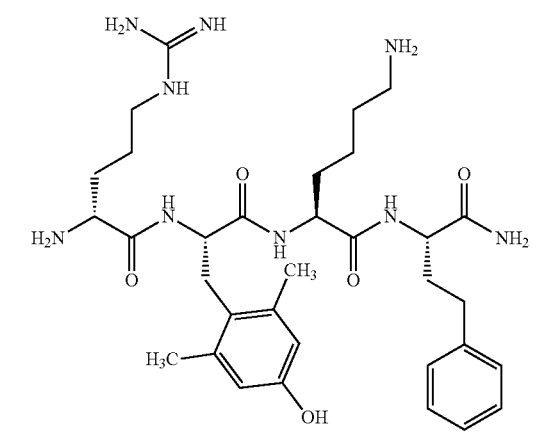 [SMILES: Cc1cc(O)cc(C)c1C[C@H](NC(=O)[C@H](N)CCCNC(=N)N)C(=O)N[C@@H](CCCCN)C(=O)N[C@@H](CCc1ccccc1)C(N)=O]
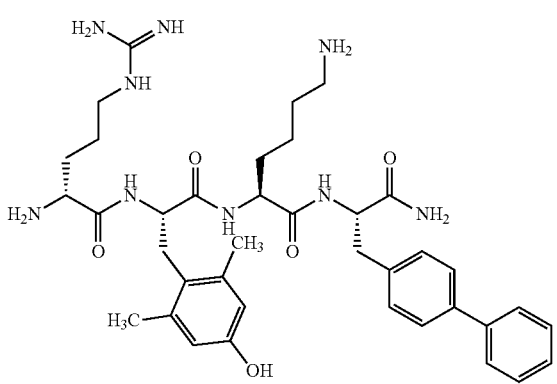 [SMILES: Cc1cc(O)cc(C)c1C[C@H](NC(=O)[C@H](N)CCCNC(=N)N)C(=O)N[C@@H](CCCCN)C(=O)N[C@@H](Cc1ccc(-c2ccccc2)cc1)C(N)=O]
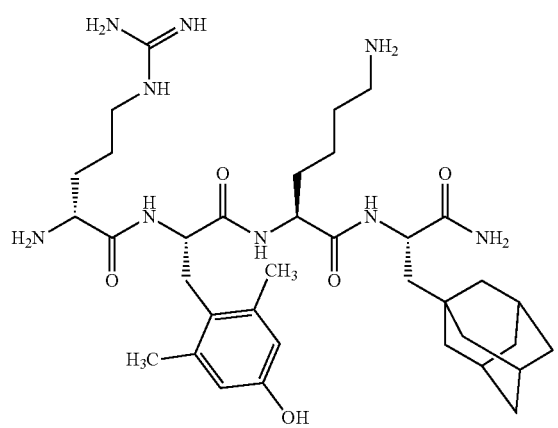 [SMILES: Cc1cc(O)cc(C)c1C[C@H](NC(=O)[C@H](N)CCCNC(=N)N)C(=O)N[C@@H](CCCCN)C(=O)N[C@@H](CC12CC3CC(CC(C3)C1)C2)C(N)=O]
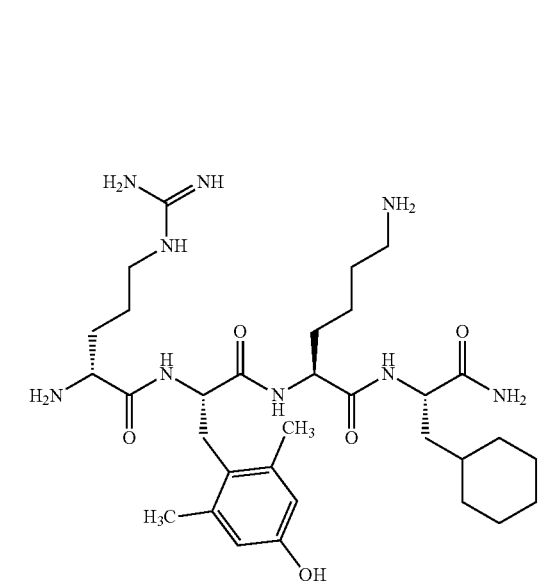 [SMILES: Cc1cc(O)cc(C)c1C[C@H](NC(=O)[C@H](N)CCCNC(=N)N)C(=O)N[C@@H](CCCCN)C(=O)N[C@@H](CC1CCCCC1)C(N)=O]
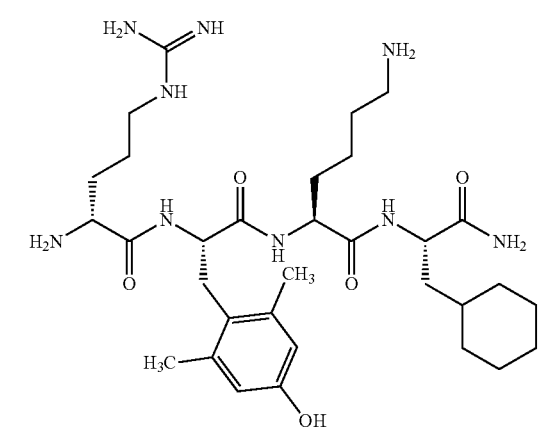
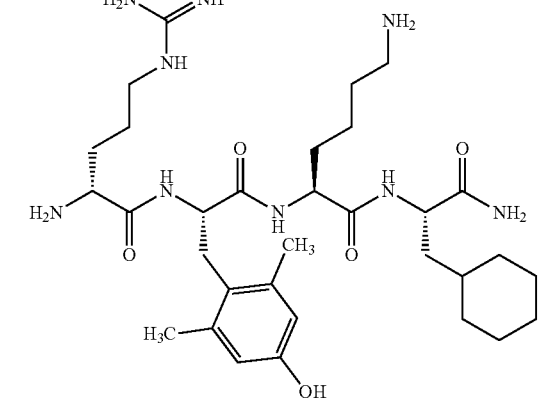

29
-continued
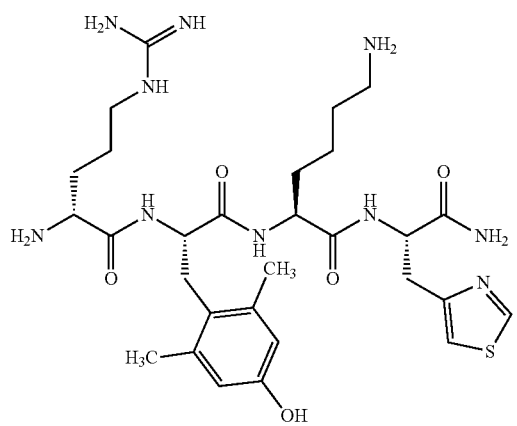 [SMILES: Cc1cc(O)cc(C)c1C[C@H](NC(=O)[C@H](N)CCCNC(=N)N)C(=O)N[C@@H](CCCCN)C(=O)N[C@@H](Cc1cscn1)C(N)=O]
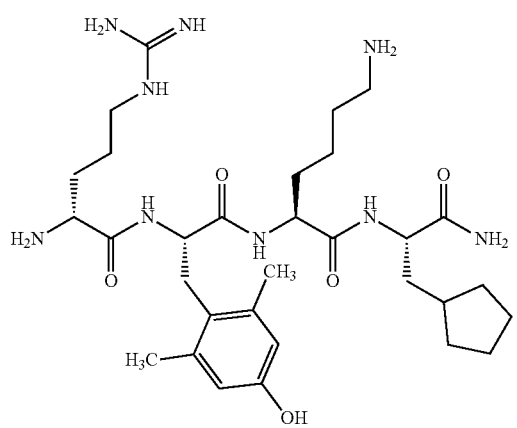 [SMILES: Cc1cc(O)cc(C)c1C[C@H](NC(=O)[C@H](N)CCCNC(=N)N)C(=O)N[C@@H](CCCCN)C(=O)N[C@@H](CC1CCCC1)C(N)=O]
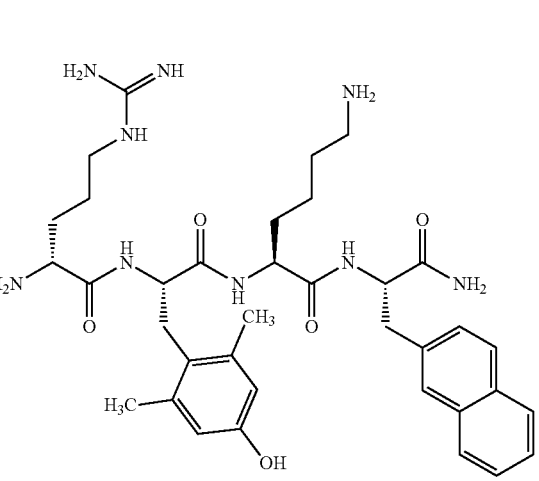
30
-continued
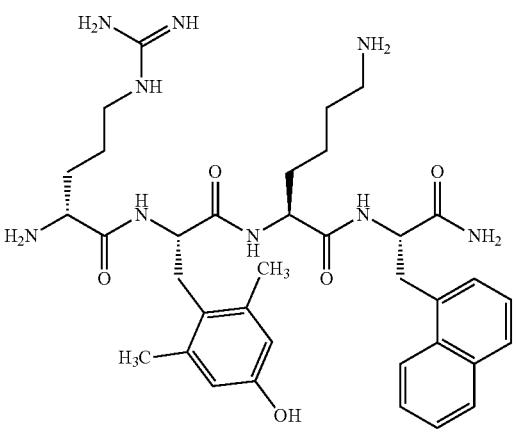 [SMILES: Cc1cc(O)cc(C)c1C[C@H](NC(=O)[C@H](N)CCCNC(=N)N)C(=O)N[C@@H](CCCCN)C(=O)N[C@@H](Cc1cccc2ccccc12)C(N)=O]
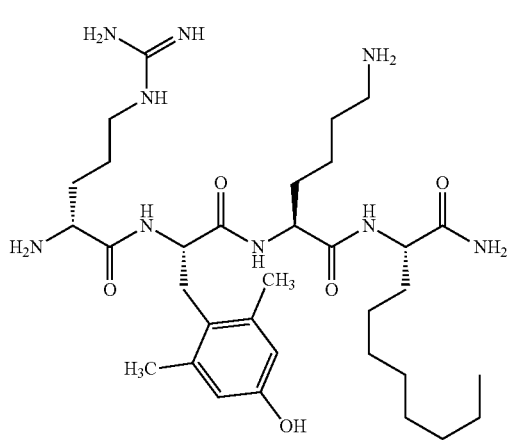 [SMILES: CCCCCCCC[C@H](NC(=O)[C@H](CCCCN)NC(=O)[C@H](Cc1c(C)cc(O)cc1C)NC(=O)[C@H](N)CCCNC(=N)N)C(N)=O]

-continued
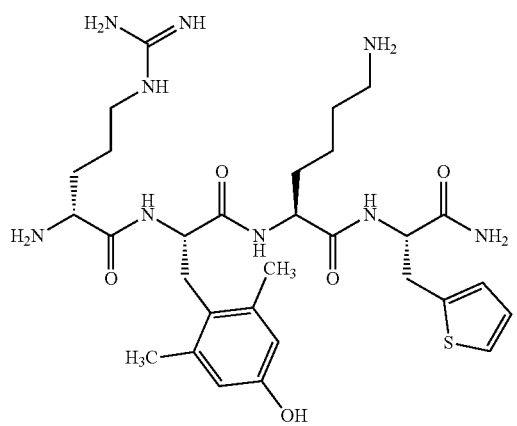 [SMILES: Cc1cc(O)cc(C)c1C[C@H](NC(=O)[C@H](N)CCCNC(=N)N)C(=O)N[C@@H](CCCCN)C(=O)N[C@@H](Cc1cccs1)C(N)=O]
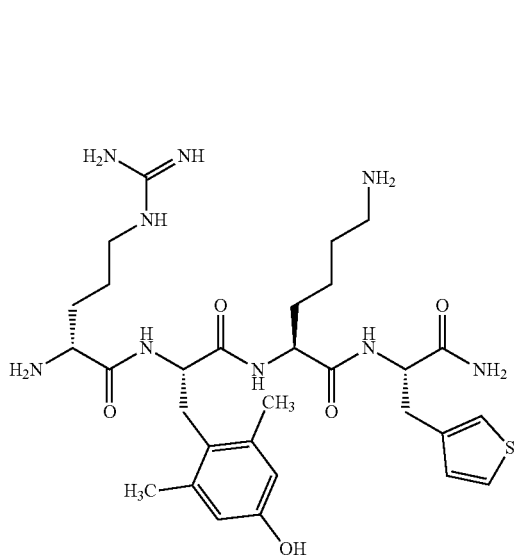 [SMILES: Cc1cc(O)cc(C)c1C[C@H](NC(=O)[C@H](N)CCCNC(=N)N)C(=O)N[C@@H](CCCCN)C(=O)N[C@@H](Cc1ccsc1)C(N)=O]
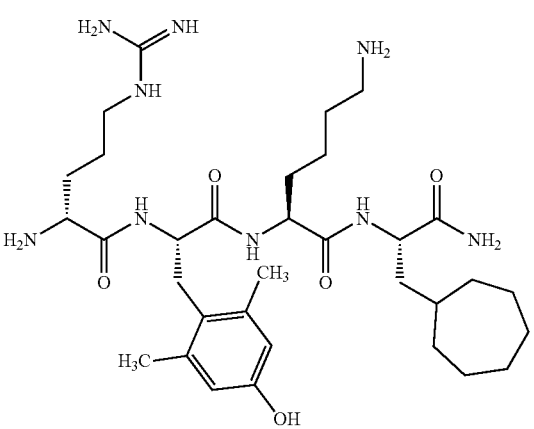 [SMILES: Cc1cc(O)cc(C)c1C[C@H](NC(=O)[C@H](N)CCCNC(=N)N)C(=O)N[C@@H](CCCCN)C(=O)N[C@@H](CC1CCCCCC1)C(N)=O]
-continued
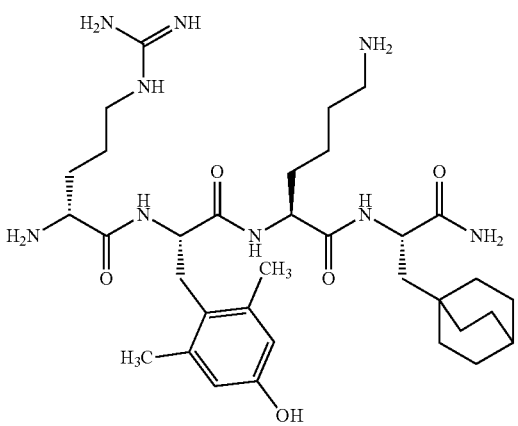 [SMILES: Cc1cc(O)cc(C)c1C[C@H](NC(=O)[C@H](N)CCCNC(=N)N)C(=O)N[C@@H](CCCCN)C(=O)N[C@@H](CC12CCC(CC1)CC2)C(N)=O]
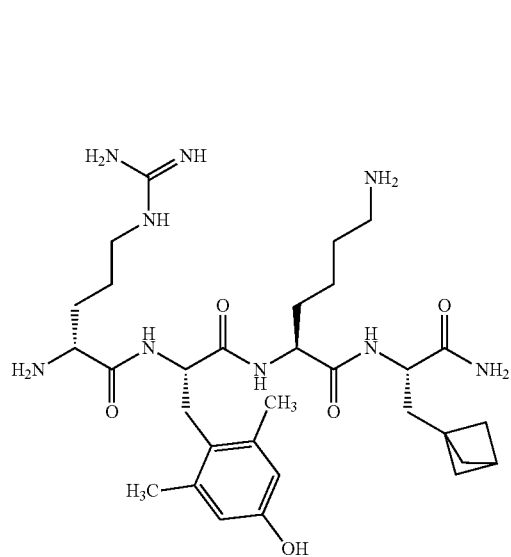 [SMILES: Cc1cc(O)cc(C)c1C[C@H](NC(=O)[C@H](N)CCCNC(=N)N)C(=O)N[C@@H](CCCCN)C(=O)N[C@@H](CC12CC(C1)C2)C(N)=O]
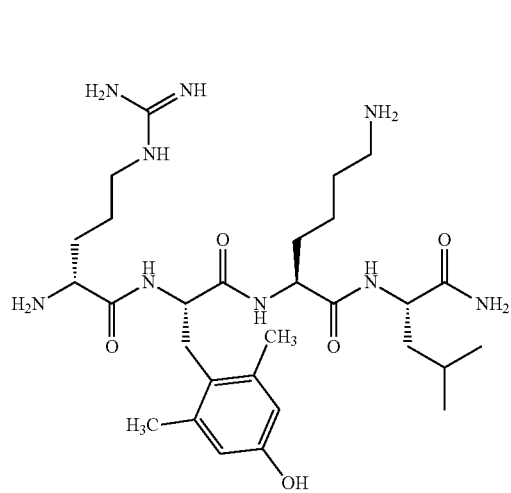 [SMILES: Cc1cc(O)cc(C)c1C[C@H](NC(=O)[C@H](N)CCCNC(=N)N)C(=O)N[C@@H](CCCCN)C(=O)N[C@@H](CC(C)C)C(N)=O]

33
-continued
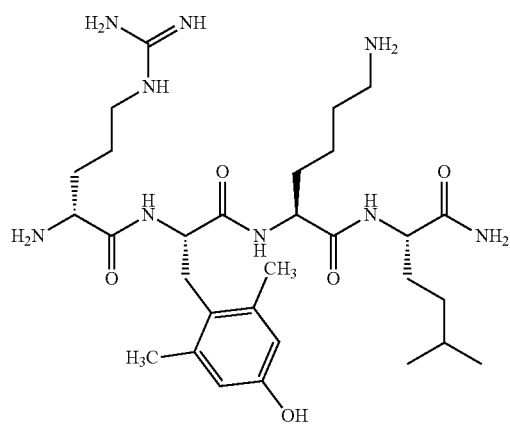 [SMILES: Cc1cc(O)cc(C)c1C[C@H](NC(=O)[C@H](N)CCCNC(=N)N)C(=O)N[C@@H](CCCCN)C(=O)N[C@@H](CCC(C)C)C(N)=O]
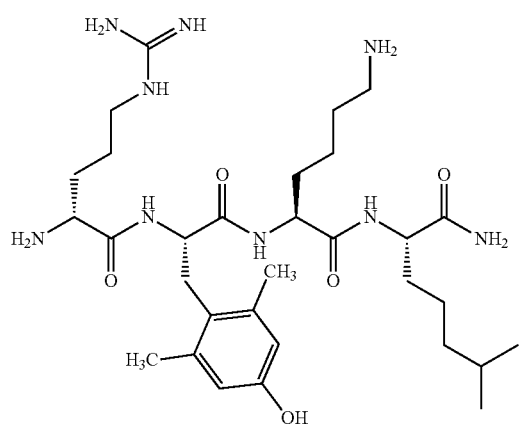 [SMILES: Cc1cc(O)cc(C)c1C[C@H](NC(=O)[C@H](N)CCCNC(=N)N)C(=O)N[C@@H](CCCCN)C(=O)N[C@@H](CCCC(C)C)C(N)=O]
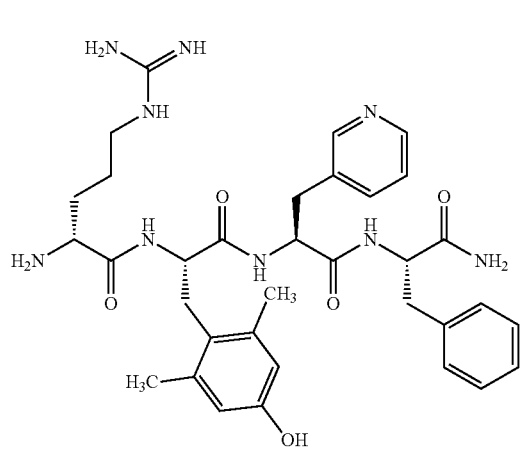 [SMILES: Cc1cc(O)cc(C)c1C[C@H](NC(=O)[C@H](N)CCCNC(=N)N)C(=O)N[C@@H](Cc1cccnc1)C(=O)N[C@@H](Cc1ccccc1)C(N)=O]
34
-continued
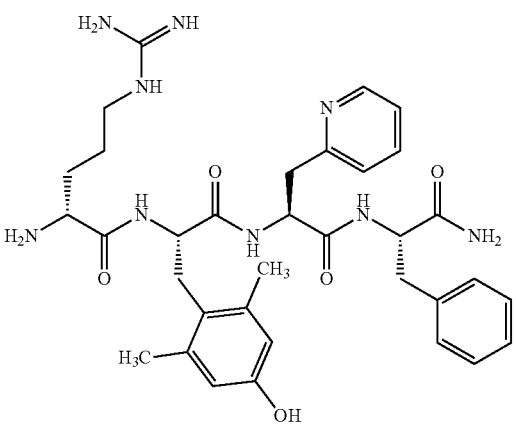 [SMILES: Cc1cc(O)cc(C)c1C[C@H](NC(=O)[C@H](N)CCCNC(=N)N)C(=O)N[C@@H](Cc1ccccn1)C(=O)N[C@@H](Cc1ccccc1)C(N)=O]
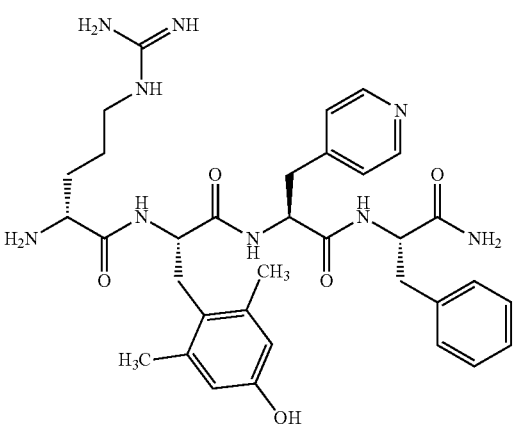 [SMILES: Cc1cc(O)cc(C)c1C[C@H](NC(=O)[C@H](N)CCCNC(=N)N)C(=O)N[C@@H](Cc1ccncc1)C(=O)N[C@@H](Cc1ccccc1)C(N)=O]
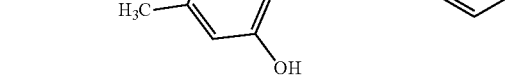

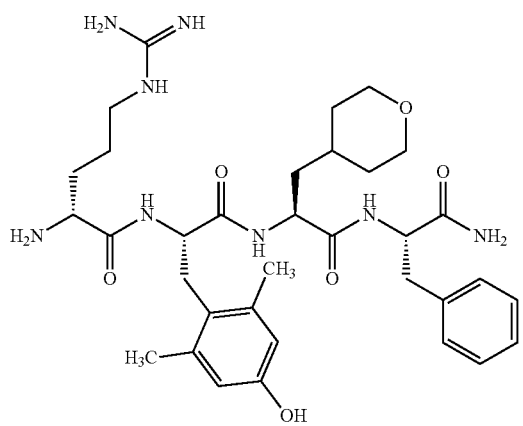 [SMILES: Cc1cc(O)cc(C)c1C[C@H](NC(=O)[C@H](N)CCCNC(=N)N)C(=O)N[C@@H](CC1CCOCC1)C(=O)N[C@@H](Cc1ccccc1)C(N)=O]
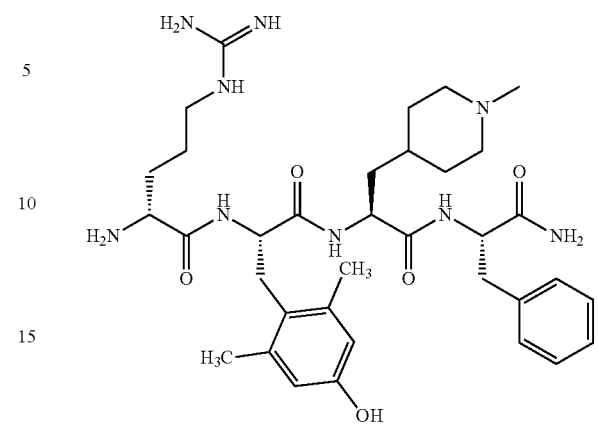
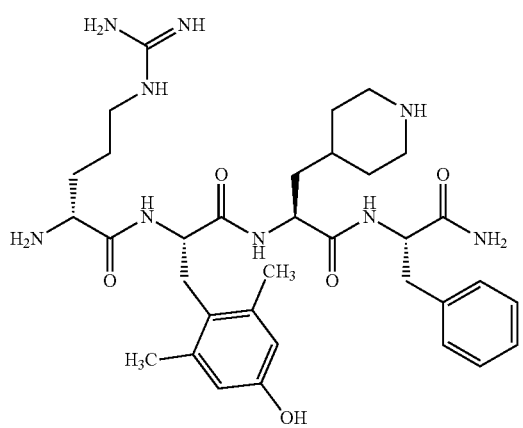 [SMILES: Cc1cc(O)cc(C)c1C[C@H](NC(=O)[C@H](N)CCCNC(=N)N)C(=O)N[C@@H](CC1CCNCC1)C(=O)N[C@@H](Cc1ccccc1)C(N)=O]
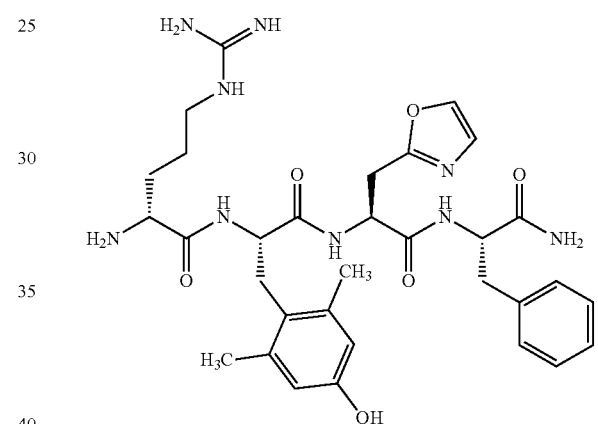
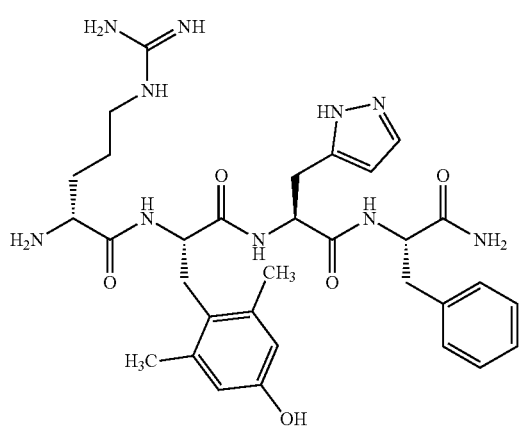 [SMILES: Cc1cc(O)cc(C)c1C[C@H](NC(=O)[C@H](N)CCCNC(=N)N)C(=O)N[C@@H](Cc1ccn[nH]1)C(=O)N[C@@H](Cc1ccccc1)C(N)=O]
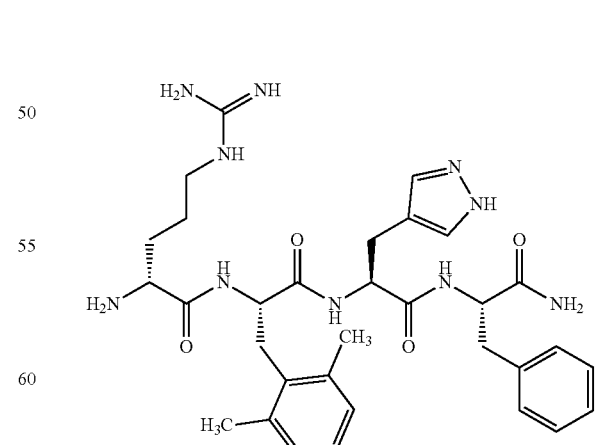

37
-continued
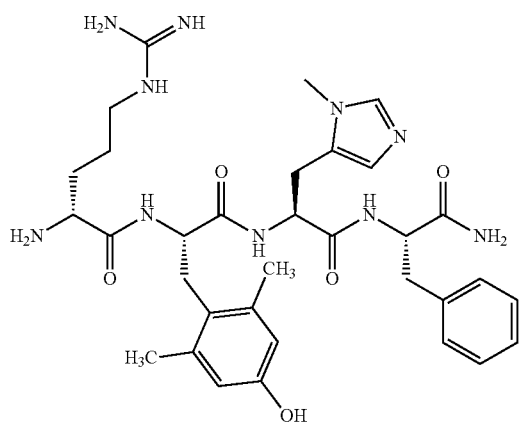 [SMILES: Cc1cc(O)cc(C)c1C[C@H](NC(=O)[C@H](N)CCCNC(=N)N)C(=O)N[C@@H](Cc1cncn1C)C(=O)N[C@@H](Cc1ccccc1)C(N)=O]
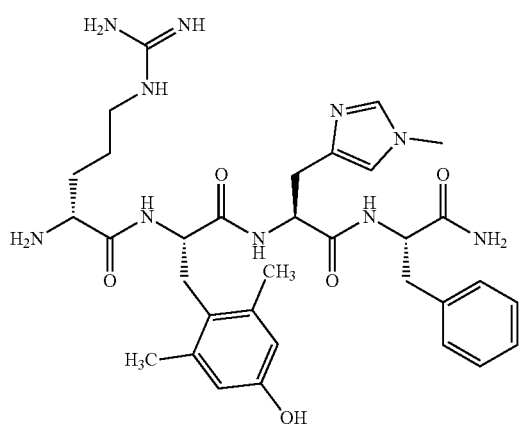 [SMILES: Cc1cc(O)cc(C)c1C[C@H](NC(=O)[C@H](N)CCCNC(=N)N)C(=O)N[C@@H](Cc1cn(C)cn1)C(=O)N[C@@H](Cc1ccccc1)C(N)=O]
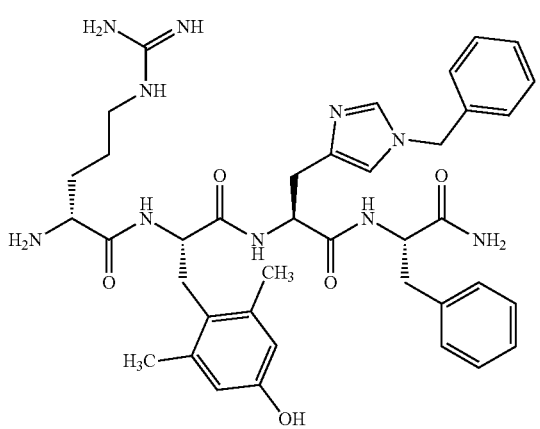 [SMILES: Cc1cc(O)cc(C)c1C[C@H](NC(=O)[C@H](N)CCCNC(=N)N)C(=O)N[C@@H](Cc1cn(Cc2ccccc2)cn1)C(=O)N[C@@H](Cc1ccccc1)C(N)=O]
38
-continued
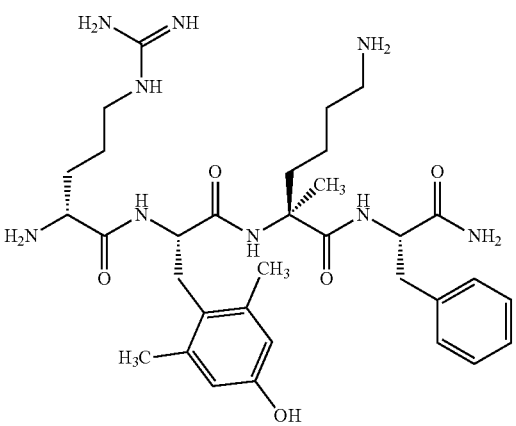 [SMILES: Cc1cc(O)cc(C)c1C[C@H](NC(=O)[C@H](N)CCCNC(=N)N)C(=O)N[C@@](C)(CCCCN)C(=O)N[C@@H](Cc1ccccc1)C(N)=O]
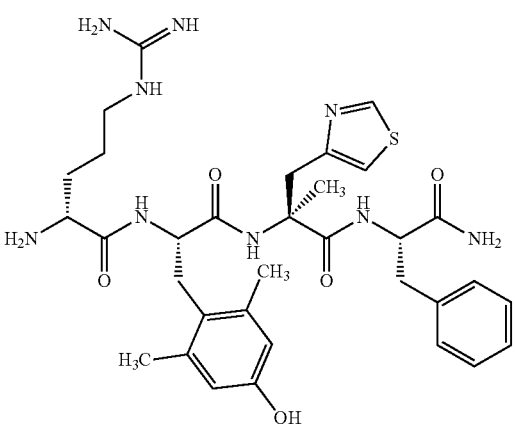 [SMILES: Cc1cc(O)cc(C)c1C[C@H](NC(=O)[C@H](N)CCCNC(=N)N)C(=O)N[C@@](C)(Cc1cscn1)C(=O)N[C@@H](Cc1ccccc1)C(N)=O]
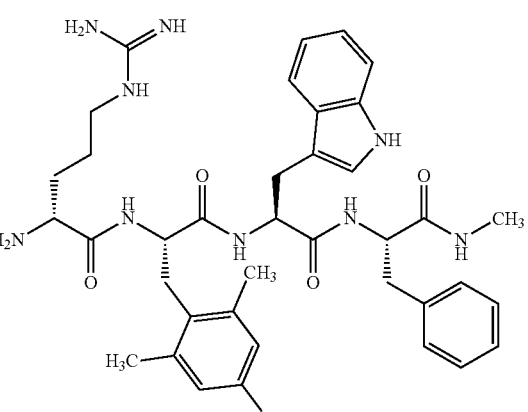

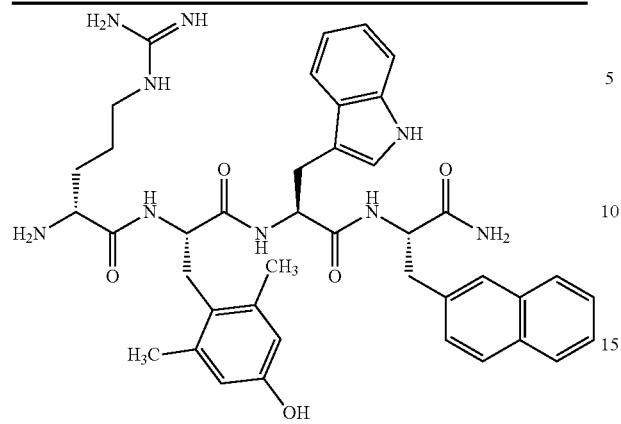
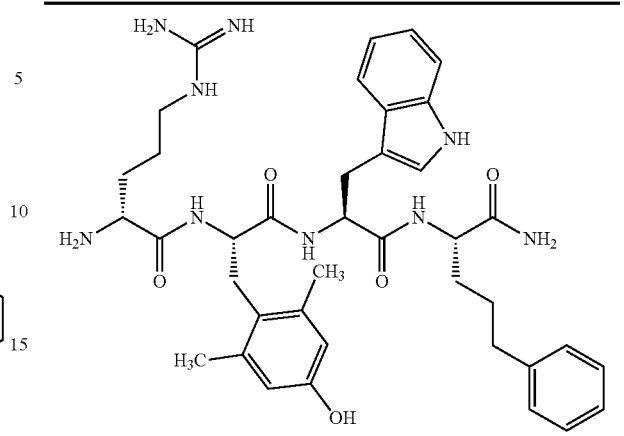
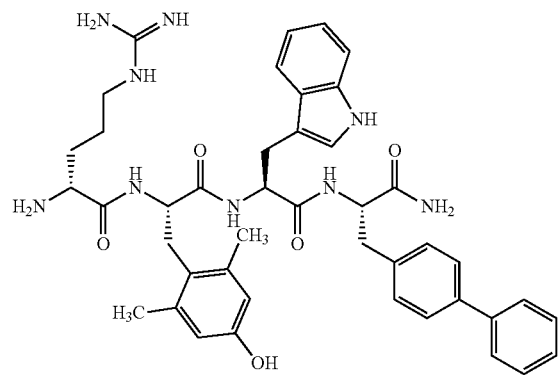 [SMILES: Cc1cc(O)cc(C)c1C[C@H](NC(=O)[C@H](N)CCCNC(=N)N)C(=O)N[C@@H](Cc1c[nH]c2ccccc12)C(=O)N[C@@H](Cc1ccc(-c2ccccc2)cc1)C(N)=O]
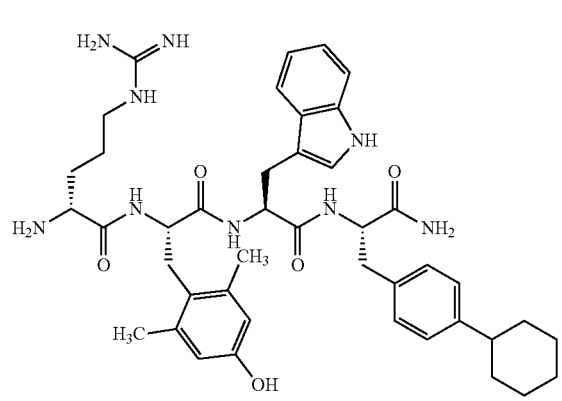
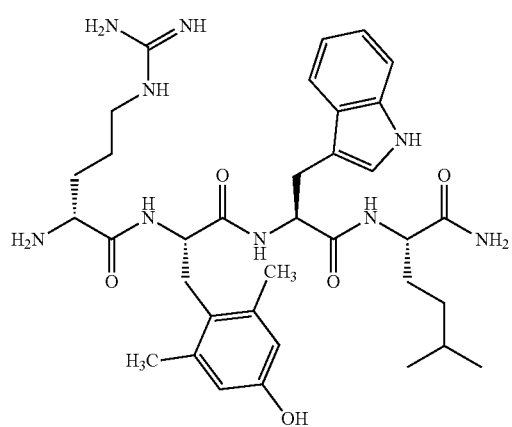 [SMILES: Cc1cc(O)cc(C)c1C[C@H](NC(=O)[C@H](N)CCCNC(=N)N)C(=O)N[C@@H](Cc1c[nH]c2ccccc12)C(=O)N[C@@H](CCC(C)C)C(N)=O]
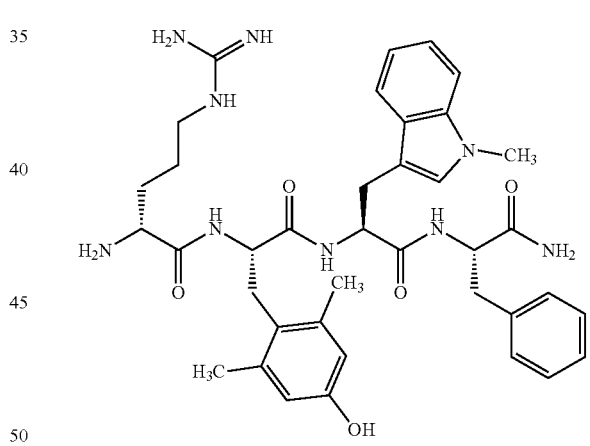
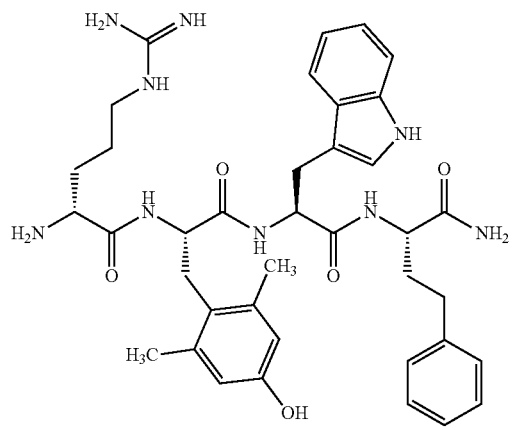 [SMILES: Cc1cc(O)cc(C)c1C[C@H](NC(=O)[C@H](N)CCCNC(=N)N)C(=O)N[C@@H](Cc1c[nH]c2ccccc12)C(=O)N[C@@H](CCc1ccccc1)C(N)=O]
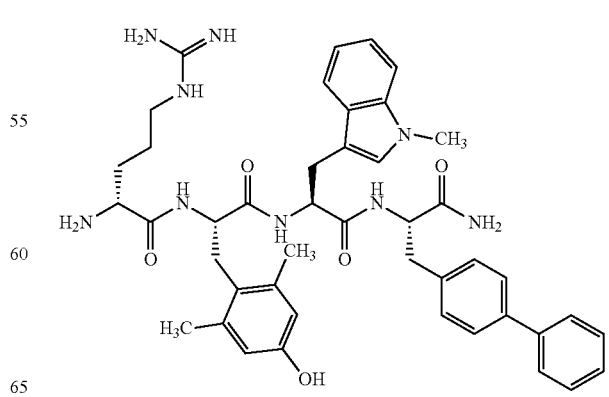

41
-continued
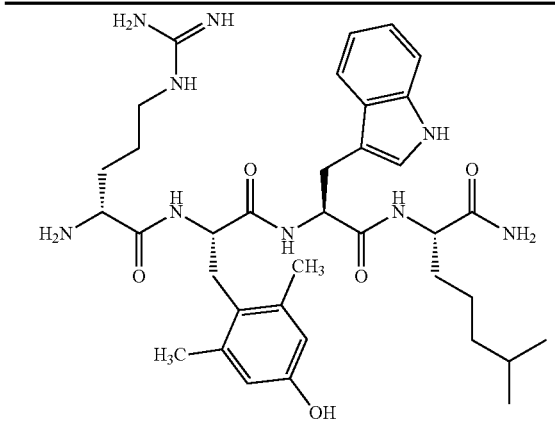
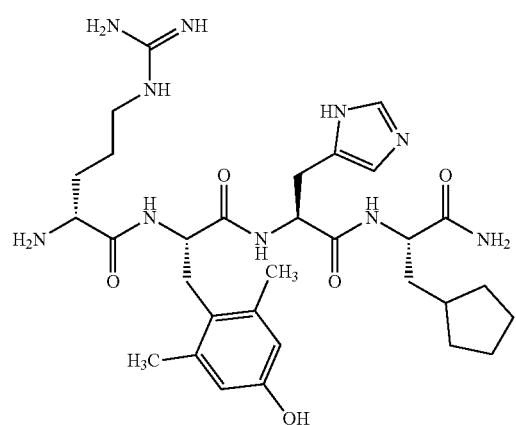 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](CC1CCCC1)C(N)=O]
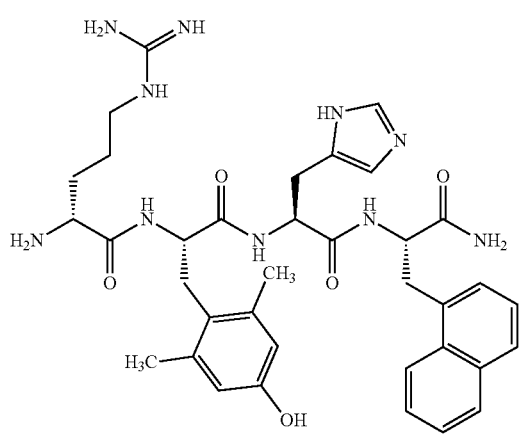 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](Cc1cccc2ccccc12)C(N)=O]
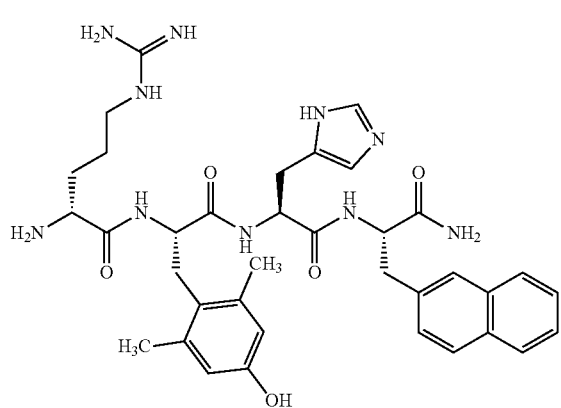 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](Cc1ccc2ccccc2c1)C(N)=O]
42
-continued
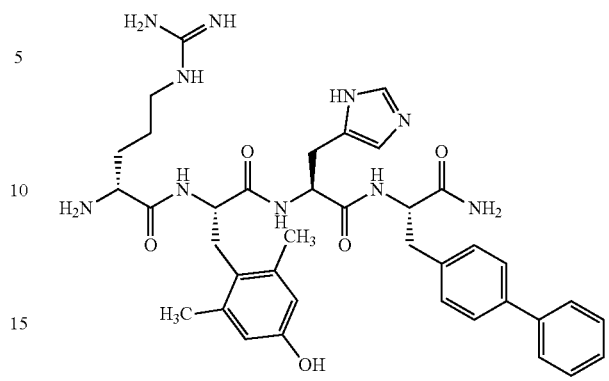
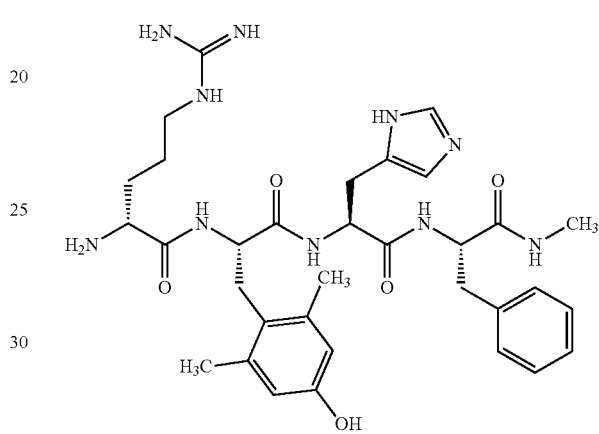
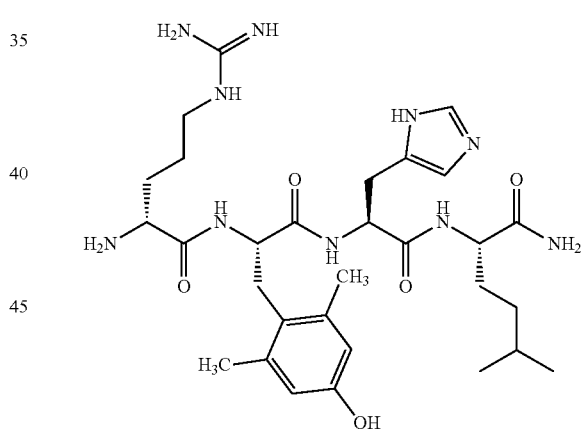
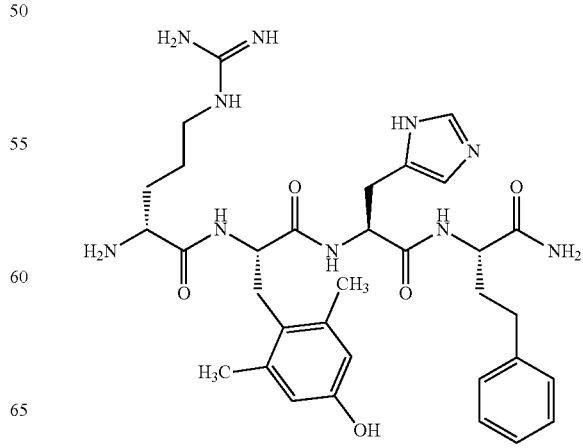

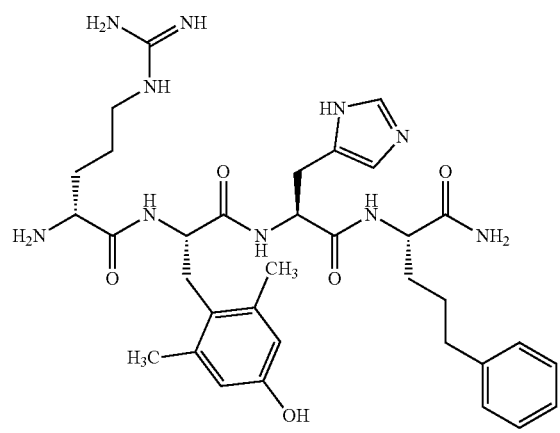 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](CCCc1ccccc1)C(N)=O]
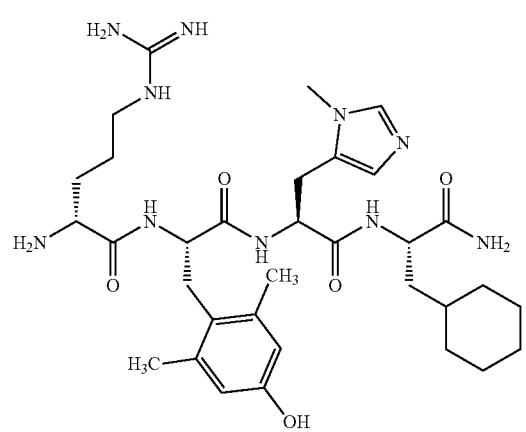 [SMILES: Cc1cc(O)cc(C)c1C[C@H](NC(=O)[C@H](N)CCCNC(=N)N)C(=O)N[C@@H](Cc1cncn1C)C(=O)N[C@@H](CC1CCCCC1)C(N)=O]
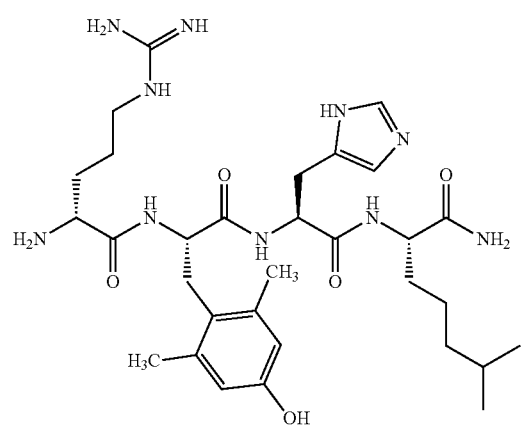 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](CCCC(C)C)C(N)=O]
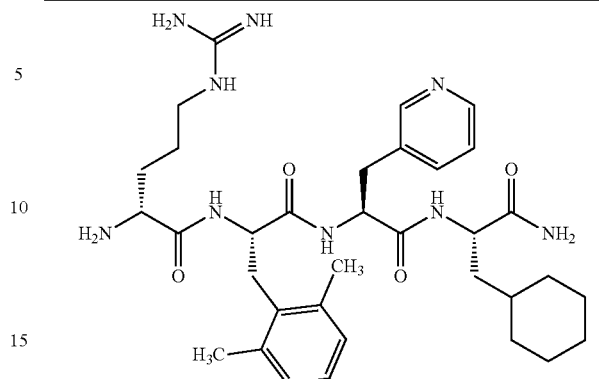
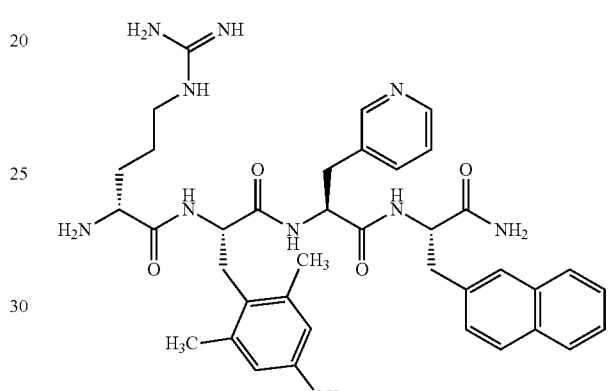
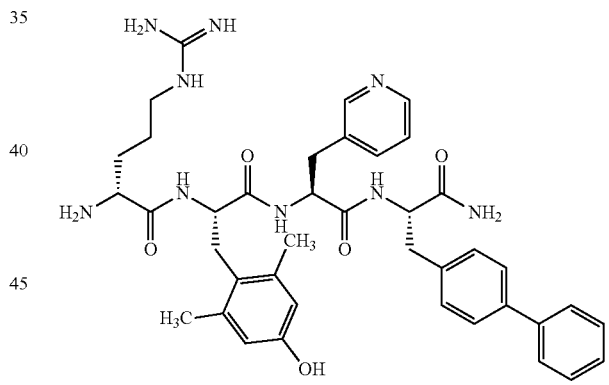
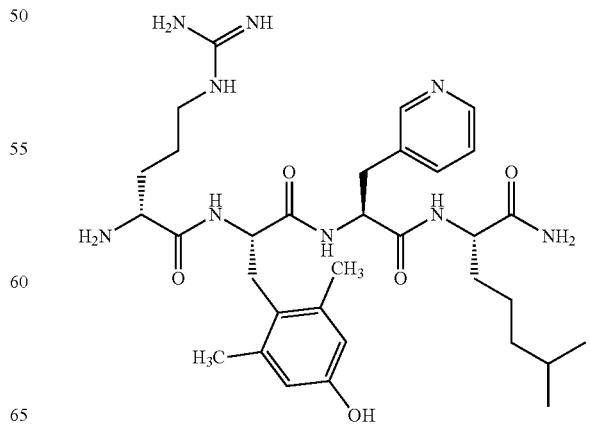

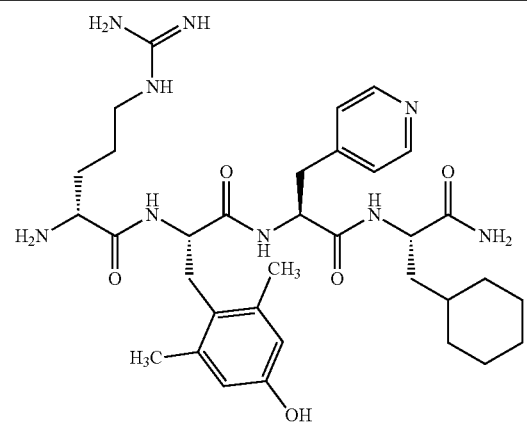
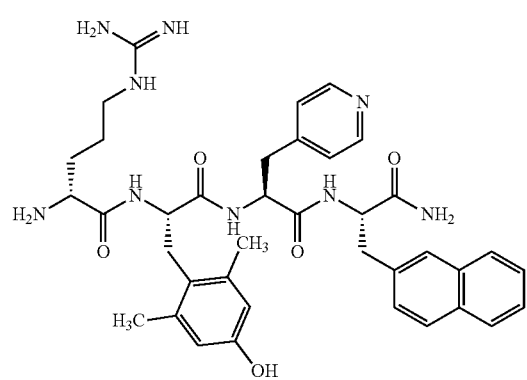 [SMILES: Cc1cc(O)cc(C)c1C[C@H](NC(=O)[C@H](N)CCCNC(=N)N)C(=O)N[C@@H](Cc1cccnc1)C(=O)N[C@@H](Cc1ccc2ccccc2c1)C(N)=O]
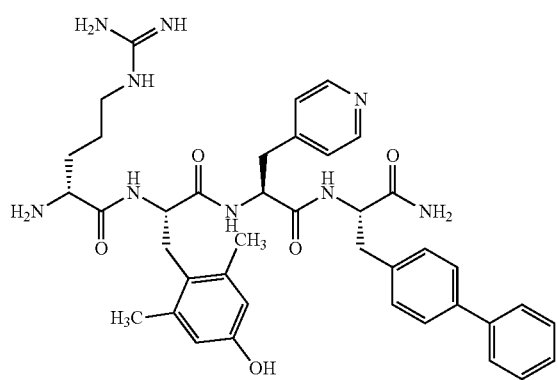 [SMILES: Cc1cc(O)cc(C)c1C[C@H](NC(=O)[C@H](N)CCCNC(=N)N)C(=O)N[C@@H](Cc1ccncc1)C(=O)N[C@@H](Cc1ccc(-c2ccccc2)cc1)C(N)=O]
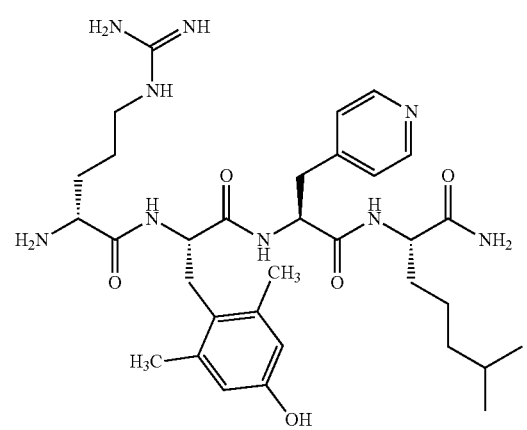 [SMILES: Cc1cc(O)cc(C)c1C[C@H](NC(=O)[C@H](N)CCCNC(=N)N)C(=O)N[C@@H](Cc1ccncc1)C(=O)N[C@@H](CCCC(C)C)C(N)=O]
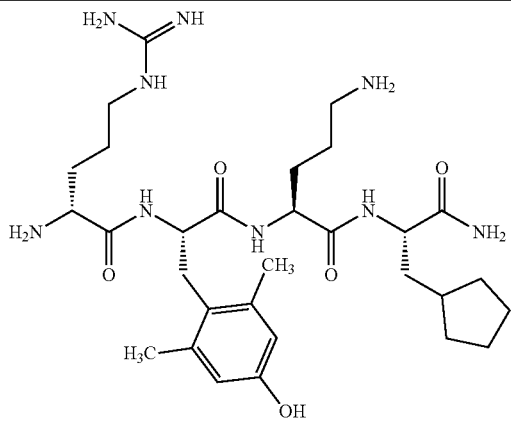
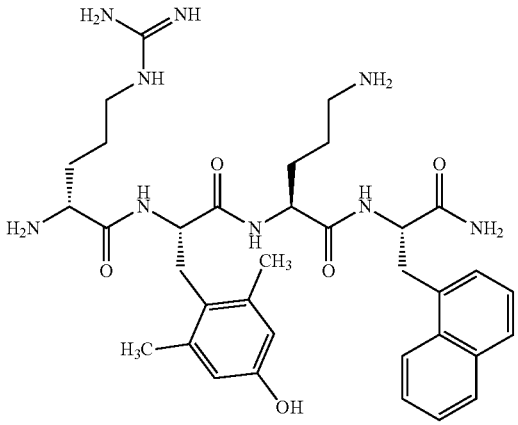 [SMILES: Cc1cc(O)cc(C)c1C[C@H](NC(=O)[C@H](N)CCCNC(=N)N)C(=O)N[C@@H](CCCN)C(=O)N[C@@H](Cc1cccc2ccccc12)C(N)=O]
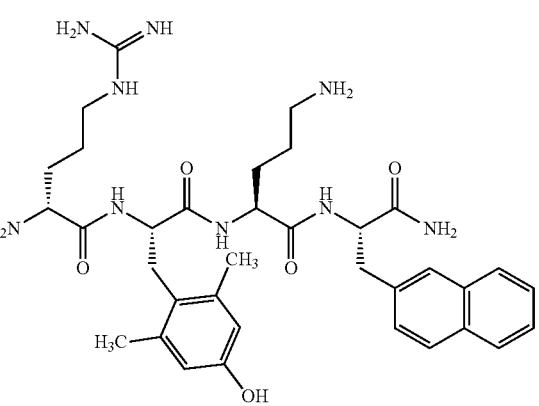
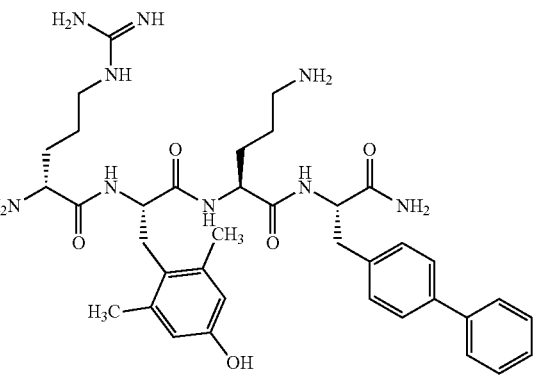

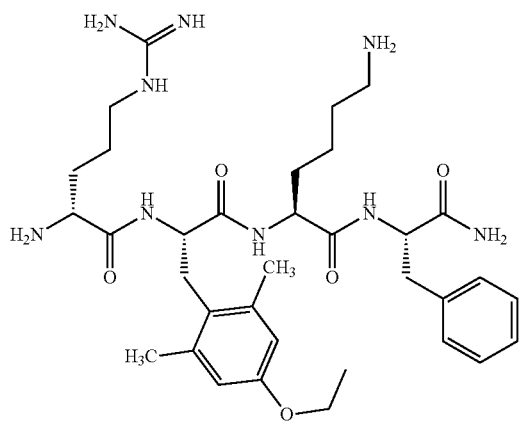 [SMILES: CCOc1cc(C)c(C[C@H](NC(=O)[C@H](N)CCCNC(=N)N)C(=O)N[C@@H](CCCCN)C(=O)N[C@@H](Cc2ccccc2)C(N)=O)c(C)c1]
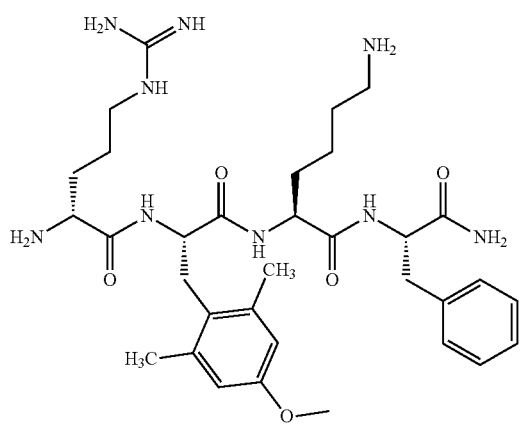 [SMILES: COc1cc(C)c(C[C@H](NC(=O)[C@H](N)CCCNC(=N)N)C(=O)N[C@@H](CCCCN)C(=O)N[C@@H](Cc2ccccc2)C(N)=O)c(C)c1]
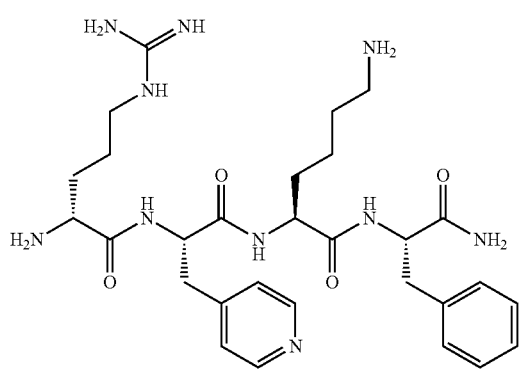 [SMILES: N=C(N)NCCC[C@@H](N)C(=O)N[C@@H](Cc1ccncc1)C(=O)N[C@@H](CCCCN)C(=O)N[C@@H](Cc1ccccc1)C(N)=O]
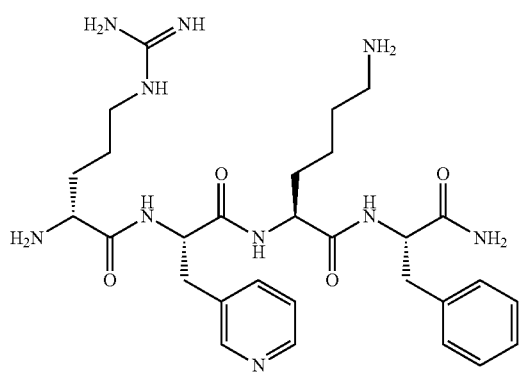 [SMILES: N=C(N)NCCC[C@@H](N)C(=O)N[C@@H](Cc1cccnc1)C(=O)N[C@@H](CCCCN)C(=O)N[C@@H](Cc1ccccc1)C(N)=O]
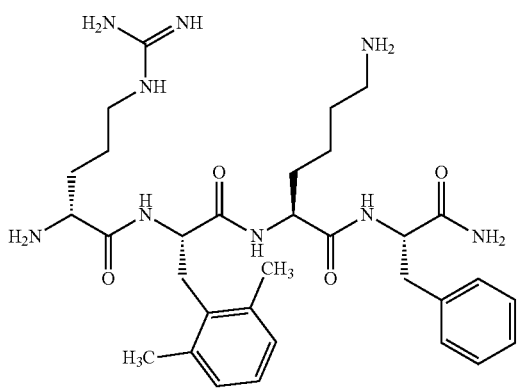 [SMILES: Cc1cccc(C)c1C[C@H](NC(=O)[C@H](N)CCCNC(=N)N)C(=O)N[C@@H](CCCCN)C(=O)N[C@@H](Cc1ccccc1)C(N)=O]
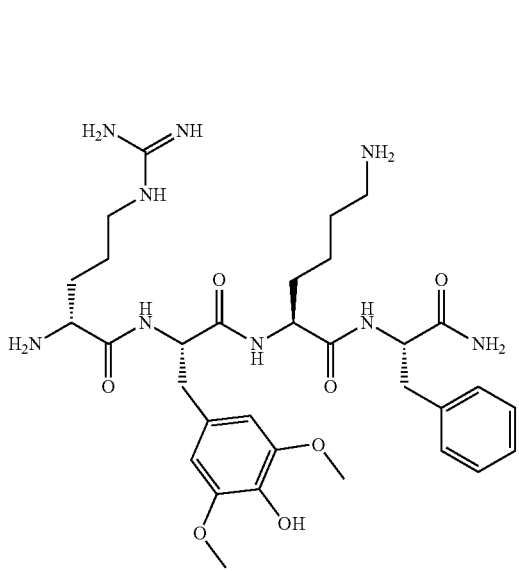 [SMILES: COc1cc(C[C@H](NC(=O)[C@H](N)CCCNC(=N)N)C(=O)N[C@@H](CCCCN)C(=O)N[C@@H](Cc2ccccc2)C(N)=O)cc(OC)c1O]
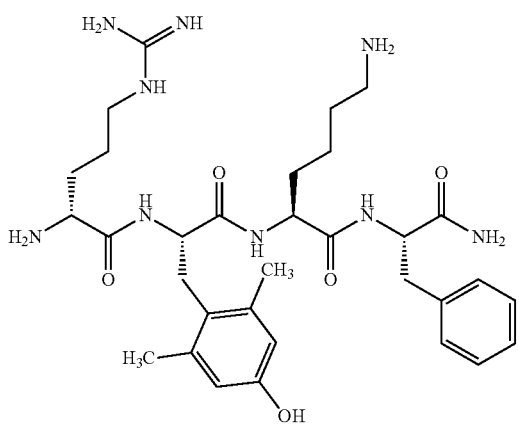 [SMILES: Cc1cc(O)cc(C)c1C[C@H](NC(=O)[C@H](N)CCCNC(=N)N)C(=O)N[C@@H](CCCCN)C(=O)N[C@@H](Cc1ccccc1)C(N)=O]

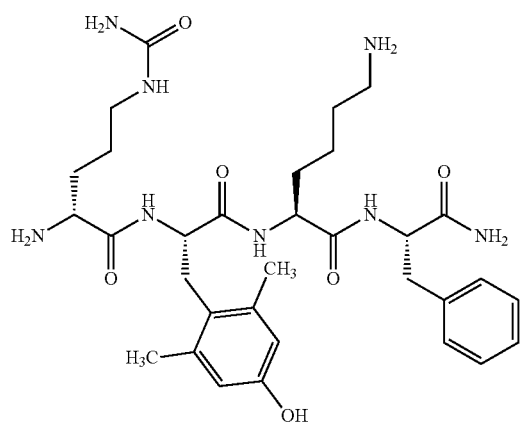 [SMILES: Cc1cc(O)cc(C)c1C[C@H](NC(=O)[C@H](N)CCCNC(N)=O)C(=O)N[C@@H](CCCCN)C(=O)N[C@@H](Cc1ccccc1)C(N)=O]
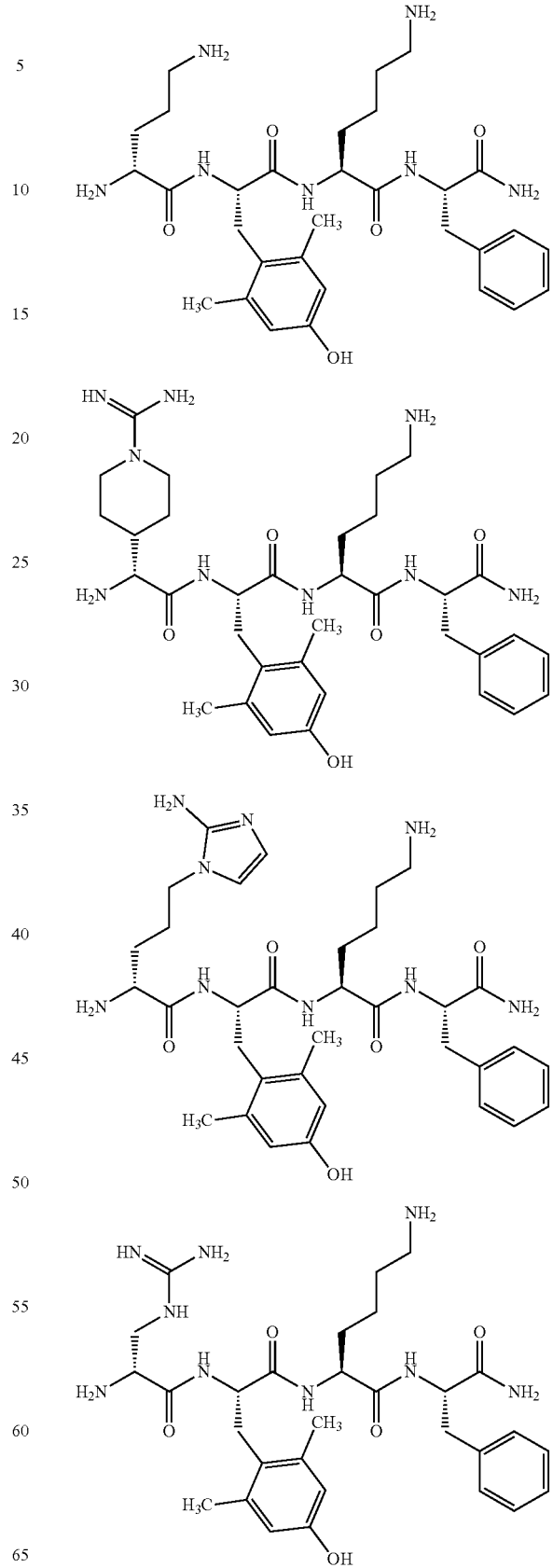

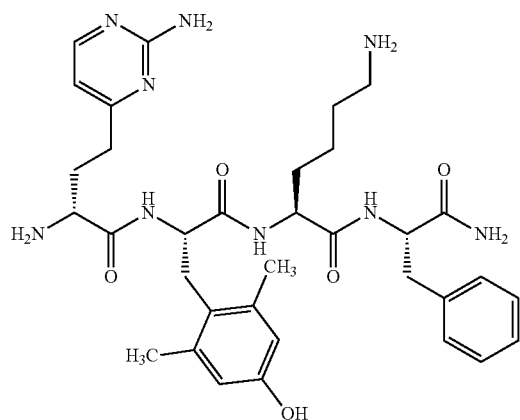 [SMILES: Cc1cc(O)cc(C)c1C[C@H](NC(=O)[C@H](N)CCc1ccnc(N)n1)C(=O)N[C@@H](CCCCN)C(=O)N[C@@H](Cc1ccccc1)C(N)=O]
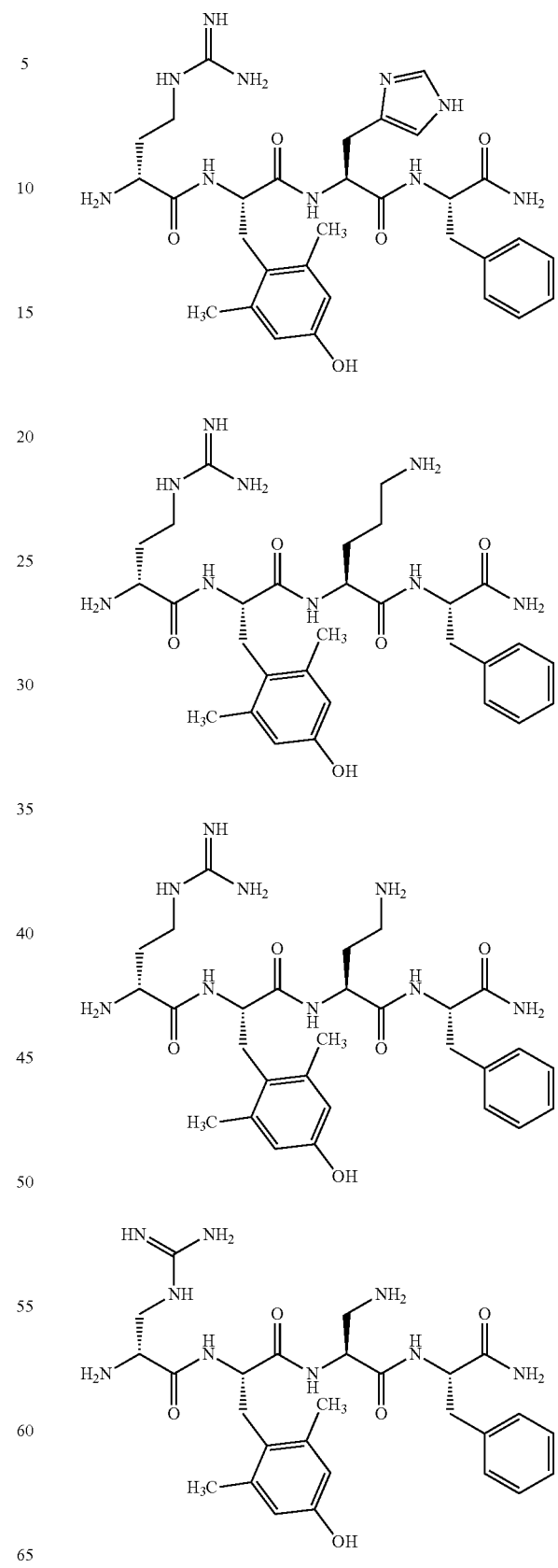

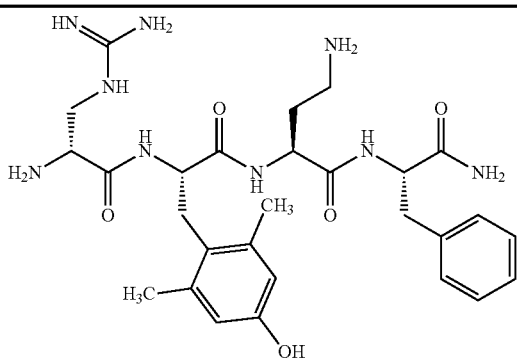

Peptide Synthesis

The peptidic compounds of the invention may be prepared using a peptide synthesis method, such as conventional liquid-phase peptide synthesis or solid-phase peptide synthesis, or by peptide synthesis by means of an automated peptide synthesizer (Kelley et al., Genetics Engineering Principles and Methods, Setlow, J. K. eds., Plenum Press NY. (1990) Vol. 12, pp. 1 to 19; Stewart et al., Solid-Phase Peptide Synthesis (1989) W. H.; Houghten, Proc. Natl. Acad. Sci. USA (1985) 82: p. 5132). The peptide thus produced can be collected or purified by a routine method, for example, chromatography, such as gel filtration chromatography, ion exchange column chromatography, affinity chromatography, reverse phase column chromatography, and HPLC, ammonium sulfate fractionation, ultrafiltration, and immunoadsorption.

In a solid-phase peptide synthesis, peptides are typically synthesized from the carbonyl group side (C-terminus) to amino group side (N-terminus) of the amino acid chain. In certain embodiments, an amino-protected amino acid is covalently bound to a solid support material through the carboxyl group of the amino acid, typically via an ester or amido bond and optionally via a linking group. The amino group may be deprotected and reacted with (i.e., "coupled" with) the carbonyl group of a second amino-protected amino acid using a coupling reagent, yielding a dipeptide bound to a solid support. These steps (i.e., deprotection, coupling) may be repeated to form the desired peptide chain. Once the desired peptide chain is complete, the peptide may be cleaved from the solid support.

In certain embodiments, the protecting groups used on the amino groups of the amino acid residues include 9-fluorenylmethyloxycarbonyl group (Fmoc) and t-butyloxycarbonyl (Boc). The Fmoc group is removed from the amino terminus with base while the Boc group is removed with acid. In alternative embodiments, the amino protecting group may be formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methylsulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group.

Many amino acids bear reactive functional groups in the side chain. In certain embodiments, such functional groups are protected in order to prevent the functional groups from reacting with the incoming amino acid. The protecting groups used with these functional groups must be stable to the conditions of peptide synthesis, but may be removed before, after, or concomitantly with cleavage of the peptide from the solid support.

In certain embodiments, the solid support material used in the solid-phase peptide synthesis method is a gel-type support such as polystyrene, polyacrylamide, or polyethylene glycol. Alternatively, materials such as pore glass, cellulose fibers, or polystyrene may be functionalized at their surface to provide a solid support for peptide synthesis.

Coupling reagents that may be used in the solid-phase peptide synthesis described herein are typically carbodiimide reagents. Examples of carbodiimide reagents include, but are not limited to, N,N'-dicyclohexylcarbodiimide (DCC), 1-(3-dimethylaminopropyl)-3-ethylcarbodiimide (EDC), N-cyclohexyl-N'-isopropylcarbodiimide (CIC), N,N'-diisopropylcarbodiimide (DIC), N-tert-butyl-N'-methylcarbodiimide (BMC), N-tert-butyl-N'-ethylcarbodiimide (BEC), bis[[4-(2,2-dimethyl-1,3-dioxolyl)]-methyl]carbodiimide (BDDC), and N,N-dicyclopentylcarbodiimide. DCC is a preferred coupling reagent.

In certain embodiments, a compound of the invention, for example, the compound pictured below, is synthesized in a linear sequential fashion, according to the solid phase synthesis depicted in Scheme 1:

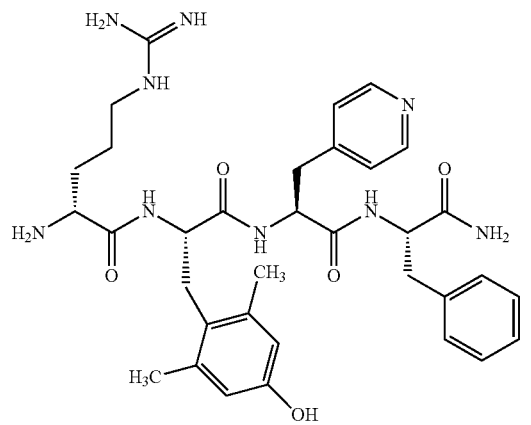

For reference in the following schemes,

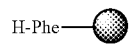

indicates

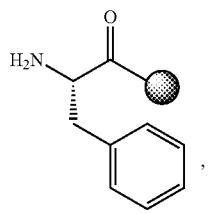

wherein

represents a solid support and optionally a linking group. Additionally, the abbreviation 4-Pal indicates a residue of 3-(4-pyridyl)-alanine. 3-(4-pyridyl)-alanine has the following structure:

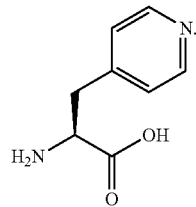

The abbreviation DMT indicates a residue of 2,6-dimethyltyrosine. 2,6-Dimethyltyrosine has the following structure:

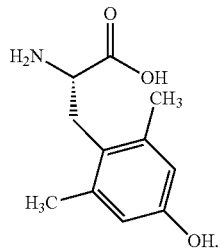

Scheme 1

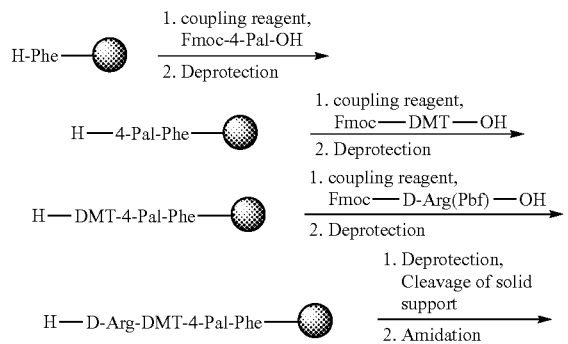

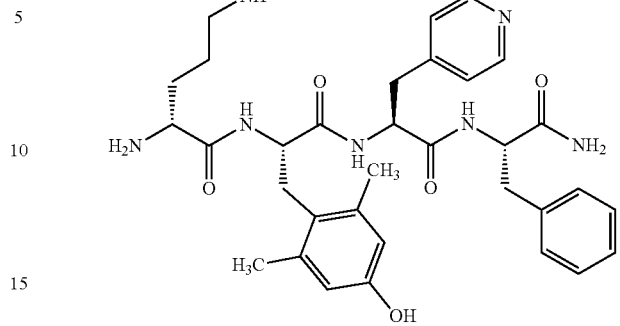

Alternatively, a compound of the invention may be synthesized in a convergent fashion, according to Scheme 2:

Scheme 2

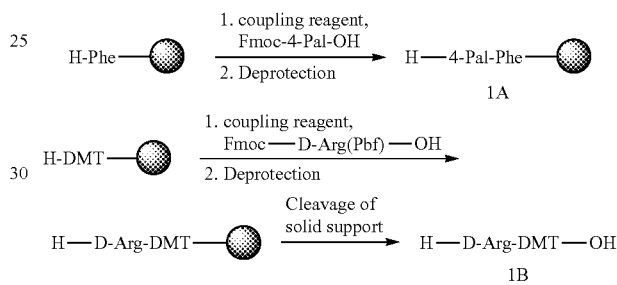

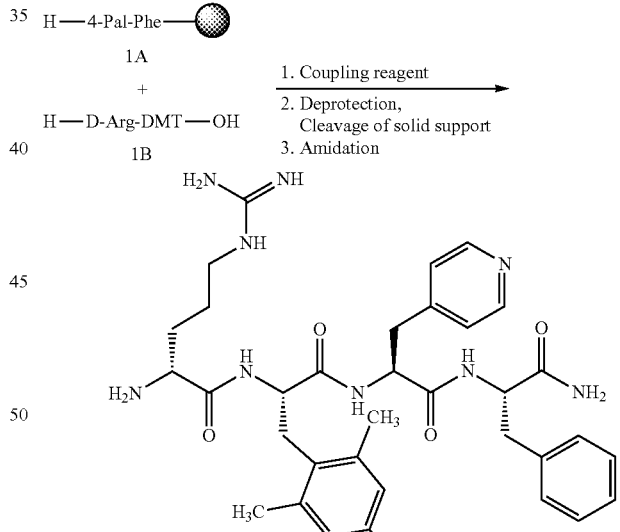

The compounds of the invention may also be synthesized according to conventional liquid-phase peptide synthetic routes. For example, the compound pictured below may be synthesized in a convergent liquid-phase synthesis, as depicted in Scheme 3.

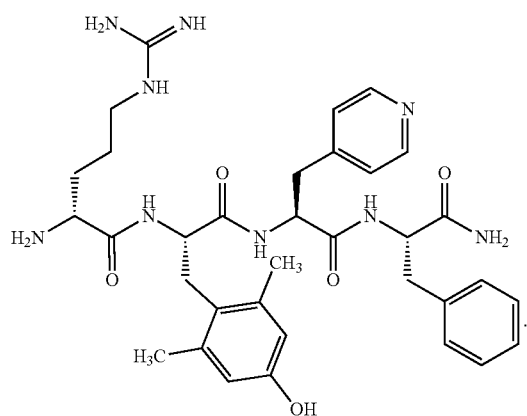 [SMILES: Cc1cc(O)cc(C)c1C[C@H](NC(=O)[C@H](N)CCCNC(=N)N)C(=O)N[C@@H](Cc1ccncc1)C(=O)N[C@@H](Cc1ccccc1)C(N)=O]
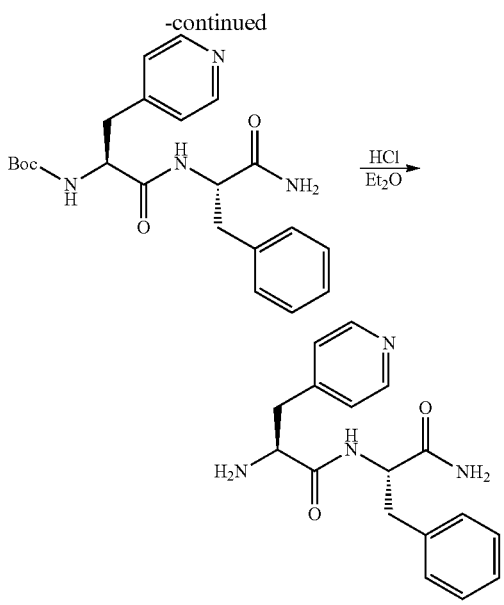
Scheme 3
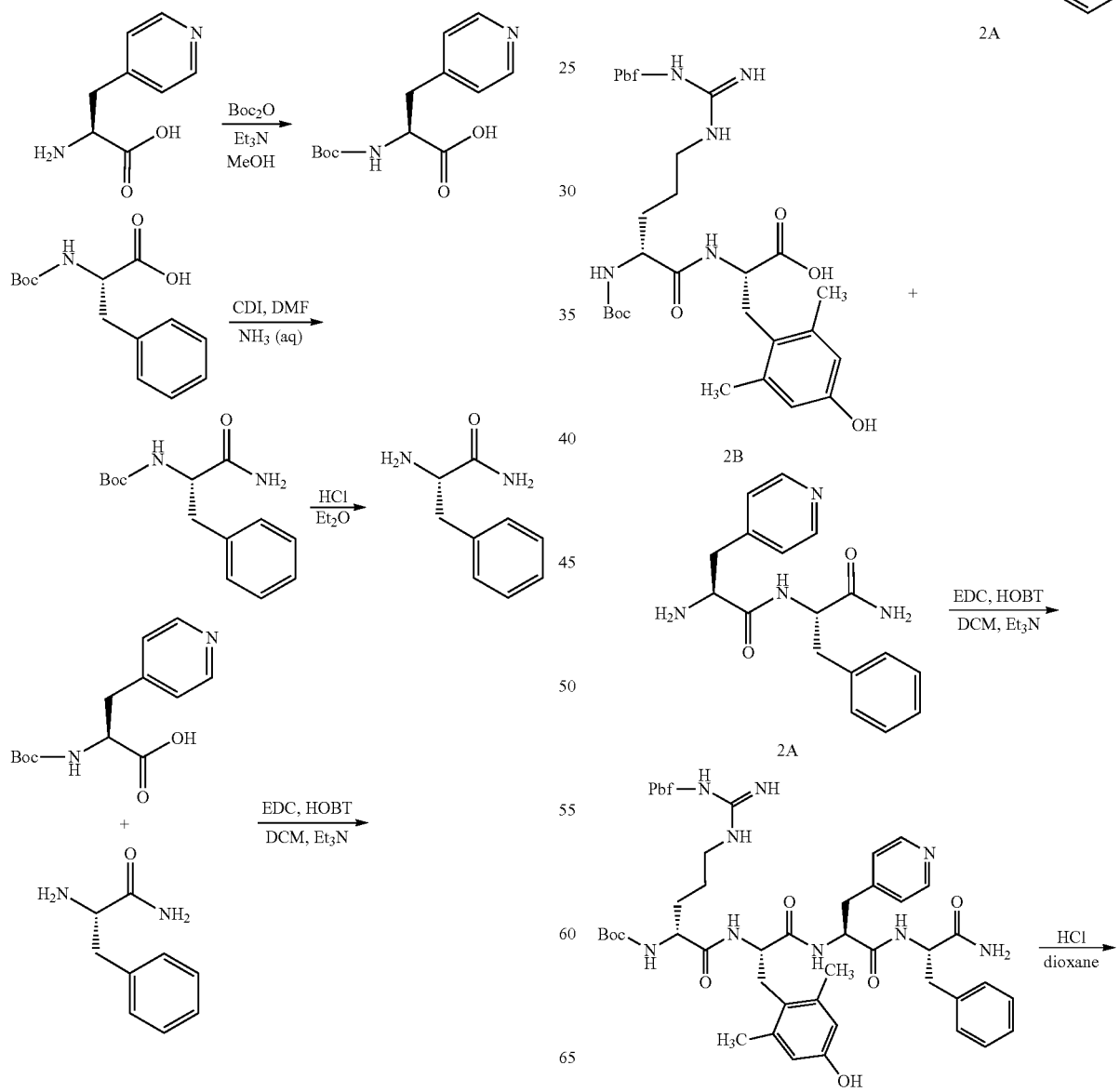

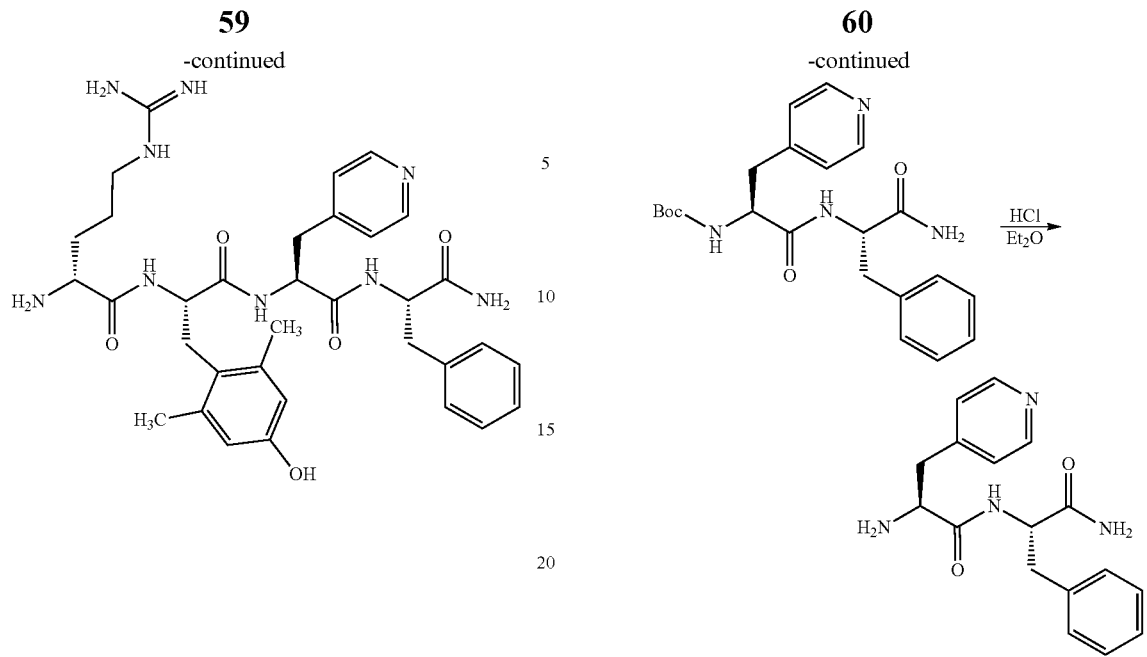
In another exemplary embodiment, the compound of the invention is made via the linear sequential liquid phase synthesis depicted in Scheme 4.
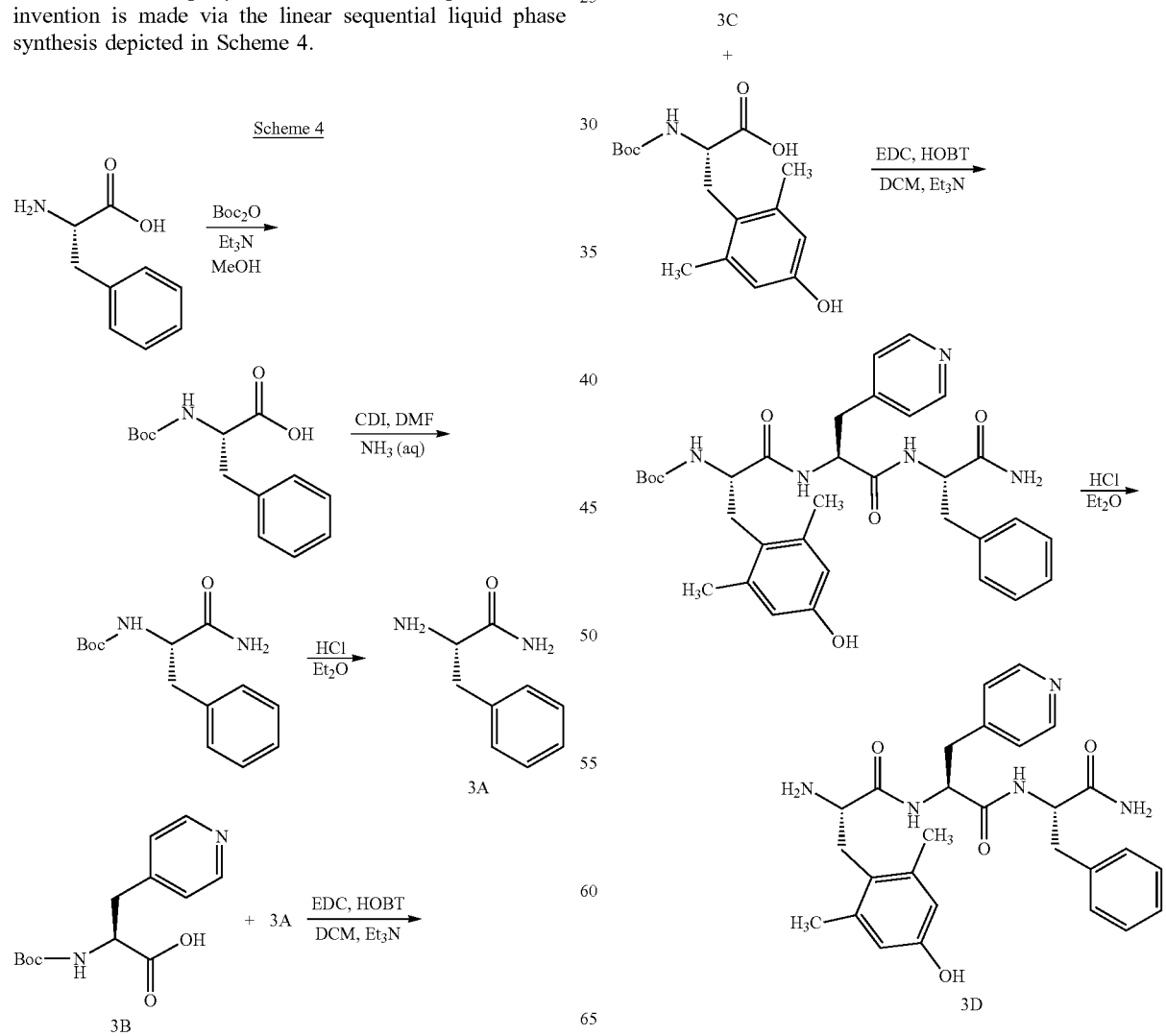

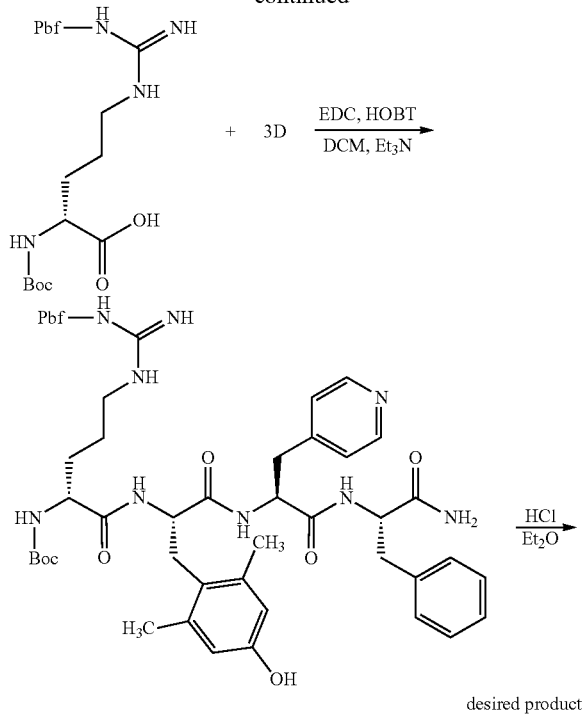

desired product

Definitions

The nomenclature used to define the peptide compounds described herein is that typically used in the art wherein the amino group at the N-terminus appears to the left and the carboxyl group at the C-terminus appears to the right.

As used herein, the term "amino acid" includes both a naturally occurring amino acid and a non-natural amino acid. The term "amino acid," unless otherwise indicated, includes both isolated amino acid molecules (i.e., molecules that include both, an amino-attached hydrogen and a carbonyl carbon-attached hydroxyl) and residues of amino acids (i.e., molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. An amino acid that is in D configuration may be written such that "D" precedes the amino acid abbreviation. For example, "D-Arg" represents arginine in the D configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

Many of the amino acids utilized herein are commercially available, or are otherwise known in the art.

With the exception of the N-terminal amino acid, all abbreviations of amino acids (for example, Phe) in this disclosure stand for the structure of —NH—C(R)(R')—CO—, wherein R and R' each is, independently, hydrogen or the side chain of an amino acid (e.g., R=benzyl and R'=H for Phe). Accordingly, phenylalanine is H-Phe-OH. The designation "OH" for these amino acids, or for peptides (e.g., Lys-Val-Leu-OH) indicates that the C-terminus is the free acid. The designation "NH$_2$" in, for example, Phe-D-Arg-Phe-Lys-NH$_2$ indicates that the C-terminus of the protected peptide fragment is amidated. Further, certain R and R', separately, or in combination as a ring structure, can include functional groups that require protection during the liquid phase synthesis.

Where the amino acid has isomeric forms, it is the L form of the amino acid that is represented unless otherwise explicitly indicated as D form, for example, D-Arg. Notably, many amino acid residues are commercially available in both D- and L-form. For example, D-Arg is a commercially available D-amino acid.

A capital letter "D" used in conjunction with an abbreviation for an amino acid residue refers to the D-form of the amino acid residue.

As used herein, the term "peptide" refers to two or more amino acids covalently linked by at least one amide bond (i.e., a bond between an amino group of one amino acid and a carboxyl group of another amino acid selected from the amino acids of the peptide fragment). The term "peptide" includes salts thereof, including pharmaceutically acceptable salts.

The articles "a" and "an" are used herein to refer to one or to more than one (i.e., to at least one) of the grammatical object of the article. By way of example, "an element" means one element or more than one element.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer (i.e., $C_1$-$C_{10}$), or 6 or fewer (i.e., $C_1$-$C_6$). Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "heterocyclyl" as used herein refers to a radical of a non-aromatic ring system, including, but not limited to, monocyclic, bicyclic, and tricyclic rings, which can be completely saturated or which can contain one or more units of unsaturation—for the avoidance of doubt, the degree of unsaturation does not result in an aromatic ring system—and having 3 to 12 atoms including at least one heteroatom, such as nitrogen, oxygen, or sulfur. For purposes of exemplification, which should not be construed as limiting the scope of this term, the following are examples of heterocyclyl rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl, and tetrahydrofuranyl.

The invention also provides salts of the compounds of the invention.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound. As another example, the salt may comprise less than one inorganic or organic acid molecule per molecule of base, such as two molecules of compound per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, 95, or 99 percent compared to control.

As used herein, the terms "treating" and "treat" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development or progression; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living animal. In various embodiments a subject is a mammal. In various embodiments a subject is a non-human mammal, including, without limitation, a mouse, rat, hamster, guinea pig, rabbit, sheep, goat, cat, dog, pig, horse, cow, or non-human primate. In certain embodiments, the subject is a human.

As used herein, "administering" has its usual meaning and encompasses administering by any suitable route of administration, including, without limitation, intravenous, intramuscular, intraperitoneal, subcutaneous, direct injection, mucosal, inhalation, oral, and topical.

As used herein, the phrase "effective amount" refers to any amount that is sufficient to achieve a desired biological effect. A "therapeutically effective amount" is an amount that is sufficient to achieve a desired therapeutic effect, e.g., to treat ischemia-reperfusion injury.

Compounds of the invention and the salts thereof can be combined with other therapeutic agents. The compounds of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compounds of the invention, when the administration of the other therapeutic agents and the compound of the invention is temporally separated. The separation in time between the administration of these compounds may be a matter of minutes or it may be longer.

Pharmaceutical Compositions, Routes of Administration, and Dosing

In certain embodiments, the invention is directed to a pharmaceutical composition, comprising a compound of the invention and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of ischemia-reperfusion injury.

Pharmaceutical compositions of the invention can be prepared by combining one or more compounds of the invention with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

In certain embodiments, intravenous administration of a compound may typically be from 0.1 mg/kg/day to 20 mg/kg/day. In one embodiment, intravenous administration of a compound may typically be from 0.1 mg/kg/day to 2 mg/kg/day. In one embodiment, intravenous administration of a compound may typically be from 0.5 mg/kg/day to 5 mg/kg/day. In one embodiment, intravenous administration of a compound may typically be from 1 mg/kg/day to 20 mg/kg/day. In one embodiment, intravenous administration of a compound may typically be from 1 mg/kg/day to 10 mg/kg/day.

Generally, daily oral doses of a compound will be, for human subjects, from about 0.01 milligrams/kg per day to 1000 milligrams/kg per day. It is expected that oral doses in the range of 0.5 to 50 milligrams/kg, in one or more administrations per day, will yield therapeutic results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For any compound described herein the therapeutically effective amount can be initially determined from animal models. A therapeutically effective dose can also be determined from human data for compounds which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode that delivers the compound to the desired surface. Administering a pharmaceutical composition may be accomplished by any means known to the skilled artisan. Routes of administration include but are not limited to intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound of the invention can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. For pharmaceutical usage, as indicated above, polyethylene glycol moieties are suitable.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds disclosed herein (or salts thereof). The compound is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of the compounds of the invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise a compound of the invention (or derivative) dissolved in water at a concentration of about 0.1 to 25 mg of biologically active compound of the invention per mL of solution. The formulation may also include a buffer and a simple sugar (e.g., for inhibitor stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, a compound may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990).

The compound of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound as described herein and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to a compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

Methods of Use

The present invention provides peptidic compounds that are useful for treating or preventing ischemia-reperfusion injury or myocardial infarction, or injury associated with myocardial infarction.

Accordingly, in certain embodiments, the invention is directed to a method of treating or preventing ischemia-reperfusion injury, comprising administering to a subject in need thereof a therapeutically effective amount of a compound of formula (I), described herein, or a pharmaceutically acceptable salt thereof. In certain such embodiments, the ischemia-reperfusion injury is cardiac ischemia-reperfusion injury. In some embodiments, the compound is administered orally, topically, systemically, intravenously, subcutaneously, intraperitoneally, or intramuscularly.

In other embodiments, the present invention provides a method for treating or preventing a myocardial infarction, comprising administering to a subject in need thereof a therapeutically effective amount of compound of formula (I), or a pharmaceutically acceptable salt thereof. Such methods may prevent injury to the heart upon reperfusion by preventing the initiation or progression of the infarction. In some embodiments, the compound is administered orally, topically, systemically, intravenously, subcutaneously, intraperitoneally, or intramuscularly.

Ischemia is reduction or decrease in blood supply to a tissue or an organ and has many different causes. Ischemia may be local, e.g., caused by thrombus or embolus, or more global, e.g., due to low perfusion pressure. An ischemic event can lead to hypoxia (reduced oxygen) and/or anoxia (absence of oxygen).

Ischemia in a tissue or organ of a mammal is a multifaceted pathological condition that is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition other molecules, such as apoptotic proteins normally compartmentalized within the mitochondria, may leak out into the cytoplasm and cause apoptotic cell death. Profound ischemia can lead to necrotic cell death.

Ischemia or hypoxia in a particular tissue or organ may be caused by a loss or severe reduction in blood supply to the tissue or organ. The loss or severe reduction in blood supply may, for example, be due to thromboembolic stroke, coronary atherosclerosis, or peripheral vascular disease. The tissue affected by ischemia or hypoxia is typically muscle, such as cardiac, skeletal, or smooth muscle.

The organ affected by ischemia or hypoxia may be any organ that is subject to ischemia or hypoxia. By way of example, but not by way of limitation, cardiac muscle ischemia or hypoxia is commonly caused by atherosclerotic or thrombotic blockages, which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Reperfusion is the restoration of blood flow to any organ or tissue in which the flow of blood is decreased or blocked. For example, blood flow can be restored to any organ or tissue affected by ischemia. The restoration of blood flow (reperfusion) can occur by any method known to those in the art. For instance, reperfusion of ischemic cardiac tissues may arise from angioplasty, coronary artery bypass graft, or the use of thrombolytic drugs.

Ischemia-reperfusion injury is the cellular or tissue damage caused when blood supply returns to the affected area after a period of ischemia. The lack of oxygen and nutrients during ischemia creates a condition in which the restoration of circulation results damage to the tissues. By way of example, but not by way of limitation, forms of myocardial reperfusion injury including reperfusion-induced arrhythmias, myocardial stunning, microvascular obstruction manifesting in sluggish coronary blood flow, and lethal myocardial reperfusion injury (i.e., reperfusion-induced death of cardiomyocytes that were viable at the end of the index ischemic event). Studies have suggested that lethal myocardial reperfusion injury accounts for about 50% of the final myocardial infarct size.

In certain embodiments, the peptide is administered orally, intravenously, or parenterally.

In certain embodiments, the subject is a human.

A peptidic compound of the invention, or a pharmaceutically acceptable salt thereof, such as acetate, tartrate, or trifluoroacetate salt, may be administered to a subject suspected of, or already suffering from ischemic injury in an amount sufficient to cure, or at least partially arrest, the symptoms of the disease, including its complications and intermediate pathological phenotypes in development of the disease. Subjects suffering from ischemic injury can be identified by any or a combination of diagnostic or prognostic assays known in the art. By way of example, but by way of limitation, in some embodiments, the ischemic injury is related to cardiac ischemia, brain ischemia, renal ischemia, cerebral ischemia, intestinal ischemia, hepatic ischemia, or myocardial infarction.

By way of example, but not by way of limitation, typical symptoms of cardiac ischemia include, but are not limited to, angina (e.g., chest pain and pressure), shortness of breath, palpitations, weakness, dizziness, nausea, sweating, rapid heartbeat, and fatigue.

In some embodiments, treatment of subjects diagnosed with cardiac ischemia with at least one peptide disclosed herein ameliorates or eliminates of one or more of the following symptoms of cardiac ischemia: angina (e.g., chest pain and pressure), shortness of breath, palpitations, weakness, dizziness, nausea, sweating, rapid heartbeat, and fatigue.

By way of example, but not by way of limitation, typical symptoms of renal ischemia include, but are not limited to, uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment of subjects diagnosed with renal ischemia with at least one peptide disclosed herein ameliorates or eliminates of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

By way of example, but not by way of limitation, typical symptoms of cerebral (or brain) ischemia include, but are not limited to, blindness in one eye, weakness in one arm or leg, weakness in one entire side of the body, dizziness, vertigo, double vision, weakness on both sides of the body, difficulty speaking, slurred speech, and the loss of coordination.

In some embodiments, treatment of subjects diagnosed with cerebral (or brain) ischemia with at least one peptide disclosed herein ameliorates or eliminates of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

In another aspect, the present invention relates to methods of treating ischemia reperfusion injury and/or side effects associated with existing therapeutics against ischemia reperfusion injury. In therapeutic applications, a composition or medicament comprising at least one compound of the invention, or a pharmaceutically acceptable salt thereof, such as acetate, tartrate or trifluoroacetate, is administered to a subject suspected of, or already suffering from ischemic reperfusion injury in an amount sufficient to cure, or at least partially arrest, the symptoms of the disease, including its complications and intermediate pathological phenotypes in development of the disease. Subjects suffering from ischemic-reperfusion injury can be identified by any or a combination of diagnostic or prognostic assays known in the art. In some embodiments, the ischemia-reperfusion injury is related to cardiac ischemia, brain ischemia, renal ischemia, cerebral ischemia, intestinal ischemia, and hepatic ischemia. In some embodiments, the peptidic compounds disclosed herein are useful in the treatment of cardiac ischemia-reperfusion injury.

In some embodiments, the peptidic compounds disclosed herein are useful in treating myocardial infarction in a subject to prevent injury to the heart upon reperfusion. In some embodiments, the invention relates to methods of coronary revascularization, comprising administering to a mammalian subject a therapeutically effective amount of a peptidic compound of the invention, or a pharmaceutically acceptable salt thereof, and performing a coronary artery bypass graft (CABG) procedure on the subject.

In some embodiments, treatment of myocardial infarction with the peptidic compounds disclosed herein reduces infarct size, increases LVDP, and increases maximal rates of contraction and relaxation (±dP/dt).

Prophylactic Methods

In some embodiments, the present invention provides methods for preventing or delaying the onset of ischemic injury or symptoms of ischemic injury in a subject at risk of having ischemia injury. In some embodiments, the present technology provides methods for preventing or reducing the symptoms of ischemic injury in a subject at risk of having ischemia injury.

In some embodiments, the present invention provides methods for preventing or delaying the onset of ischemia-reperfusion injury or symptoms of ischemia-reperfusion injury in a subject at risk of having ischemia-reperfusion injury. In some embodiments, the present invention provides methods for preventing or reducing the symptoms of ischemia reperfusion injury in a subject at risk of having ischemia-reperfusion injury.

In some embodiments, the ischemic injury, the ischemia-reperfusion injury, or symptoms of ischemic or ischemia-reperfusion injury is related to cardiac ischemia, brain ischemia, renal ischemia, cerebral ischemia, intestinal ischemia, and hepatic ischemia. In some embodiments, the ischemic injury is myocardial infarction.

In some embodiments, the peptidic compounds disclosed herein are useful in the treatment or prevention of cardiac ischemia-reperfusion injury. In some embodiments, the peptidic compounds disclosed herein are useful in the prevention of cardiac ischemia-reperfusion injury.

Subjects at risk for ischemic injury or ischemia-reperfusion injury can be identified by, e.g., any or a combination of diagnostic or prognostic assays known in the art. In prophylactic applications, a pharmaceutical composition or medicament of a compound of the invention, or a pharmaceutically acceptable salt thereof, such as acetate, tartrate, or trifluoroacetate salt, is administered to a subject susceptible to, or otherwise at risk of for ischemic injury or ischemia reperfusion injury in an amount sufficient to eliminate, reduce the risk, or delay the onset of the disease, including biochemical, histologic and/or behavioral symptoms of the disease, its complications and intermediate pathological phenotypes presenting during development of the disease or reduce the symptoms and/or complications and intermediate pathological phenotypes presenting during development of the disease. Administration of a prophylactic peptide can occur prior to the manifestation of symptoms characteristic of the disease or disorder, such that the disease or disorder is prevented, delayed in its progression, or the severity of the symptoms or side effects of the disease or disorder are reduced.

By way of example, in some embodiments, subjects may be at risk for cardiac ischemia if they have coronary artery disease (atherosclerosis), blood clots, or coronary artery spasm.

By way of example, but not by way of limitation, in some embodiments, subjects may be at risk for renal ischemia if they have kidney injury (e.g., acute kidney injury) and/or injuries or complications from surgeries in which the kidneys are deprived of normal blood flow for extended periods of time (e.g., heart-bypass surgery).

By way of example, but not by way of limitation, in some embodiments, subjects may be at risk for cerebral ischemia if they have sickle cell anemia, compressed blood vessels, ventricular tachycardia, plaque buildup in the arteries, blood clots, extremely low blood pressure as a result of heart attack, had a stroke, or congenital heart defects.

For therapeutic and/or prophylactic applications, a composition comprising at least one peptidic compound described herein, or a pharmaceutically acceptable salt thereof, such as acetate, tartrate, or trifluoroacetate salt, is administered to a subject in need thereof. In some embodiments, the peptide composition is administered one, two, three, four, or five times per day. In some embodiments, the peptide composition is administered more than five times per day. Additionally or alternatively, in some embodiments, the peptide composition is administered every day, every other day, every third day, every fourth day, every fifth day, or every sixth day. In some embodiments, the peptide composition is administered weekly, bi-weekly, tri-weekly, or monthly. In some embodiments, the peptide composition is administered for a period of one, two, three, four, or five weeks. In some embodiments, the peptide is administered for six weeks or more. In some embodiments, the peptide is administered for twelve weeks or more. In some embodiments, the peptide is administered for a period of less than one year. In some embodiments, the peptide is administered for a period of more than one year. In some embodiments, treatment with at least one peptide disclosed herein will prevent or delay the onset of one or more of the following symptoms of cardiac ischemia: angina (e.g., chest pain and pressure), shortness of breath, palpitations, weakness, dizziness, nausea, sweating, rapid heartbeat, and fatigue.

In some embodiments, treatment with at least one peptide disclosed herein will prevent or delay the onset of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment with at least one peptide disclosed herein will prevent or delay the onset of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

Methods of Evaluating Metabolic Stability

In certain embodiments, the following methods can be used to evaluate the metabolic stability of the compounds of the invention.

Certain in vitro liver metabolism studies have been described previously in the following references: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: Human liver microsomes (20 mg/mL) may be obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) may be purchased from Sigma-Aldrich.

Determination of Metabolic Stability: 7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM MgCl$_2$. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. Testing is done in triplicate.

Data analysis: The in vitro half-lives ($t_{1/2}$s) for test compounds are calculated from the slopes of the linear regression of % parent remaining (ln) vs incubation time relationship: in vitro $t_{1/2}$=0.693/k, where k=−[slope of linear regression of % parent remaining (ln) vs incubation time]

EQUIVALENTS

Having described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

INCORPORATION BY REFERENCE

All U.S. patents and U.S. and PCT published patent applications mentioned in the description above are incorporated by reference herein in their entirety.

We claim:

1. A compound of formula (I), or a pharmaceutically acceptable salt thereof:

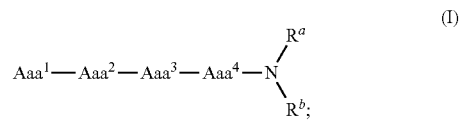

wherein:

Aaa$^1$ is an amino acid residue selected from the group consisting of:

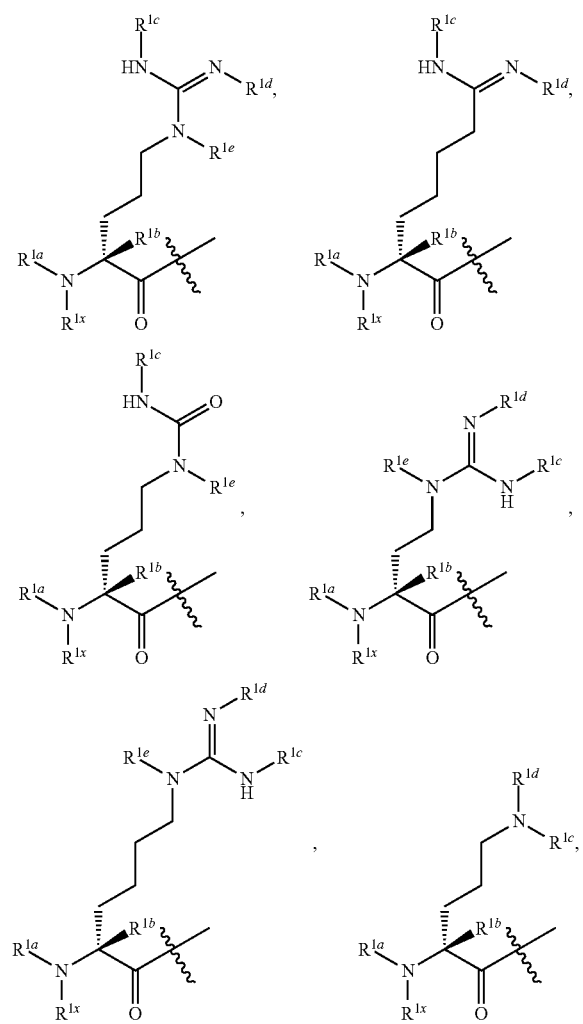

-continued
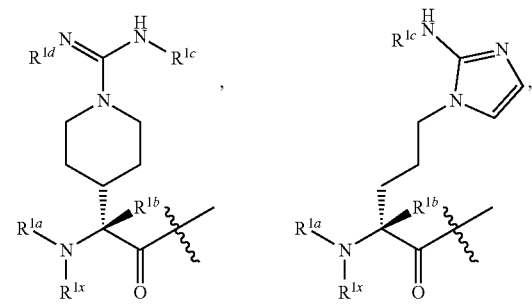
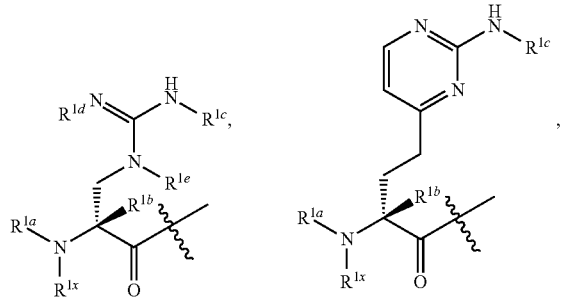
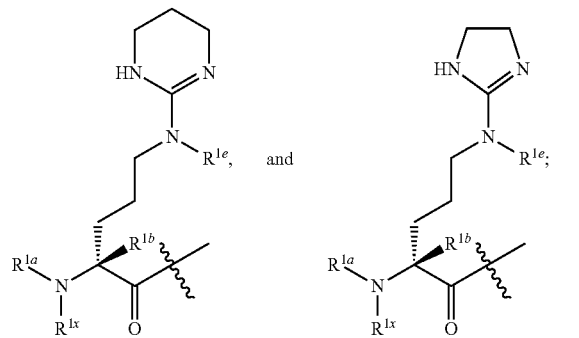
Aaa² is an amino acid residue selected from the group consisting of:
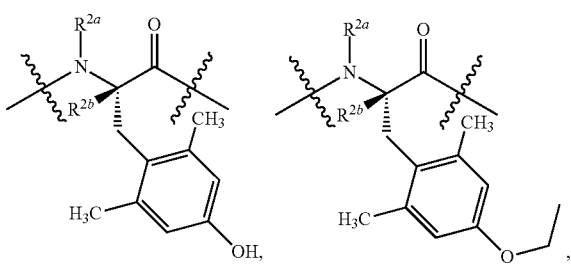
-continued
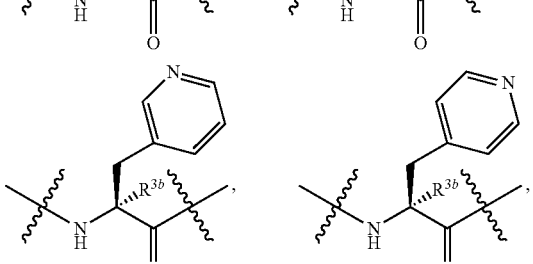
Aaa³ is an amino acid residue selected from the group consisting of:
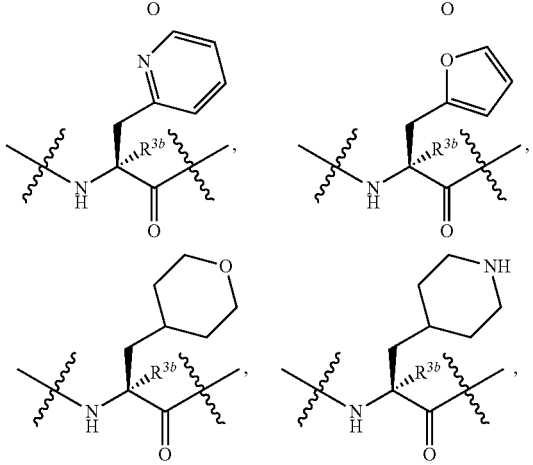

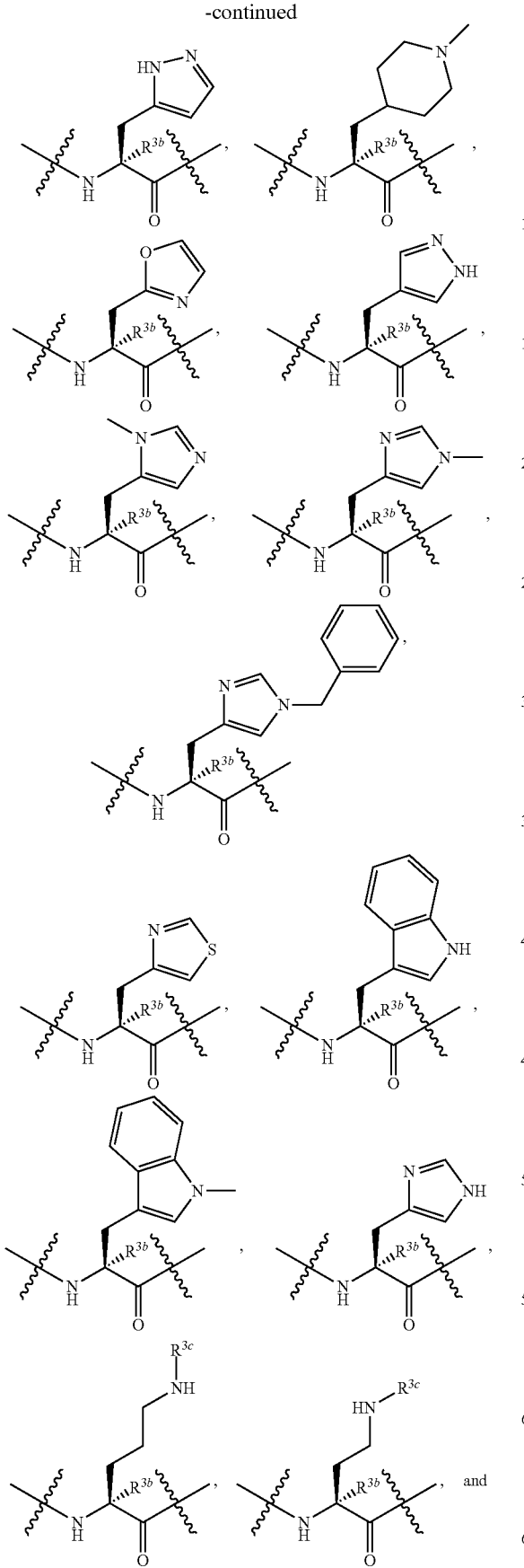
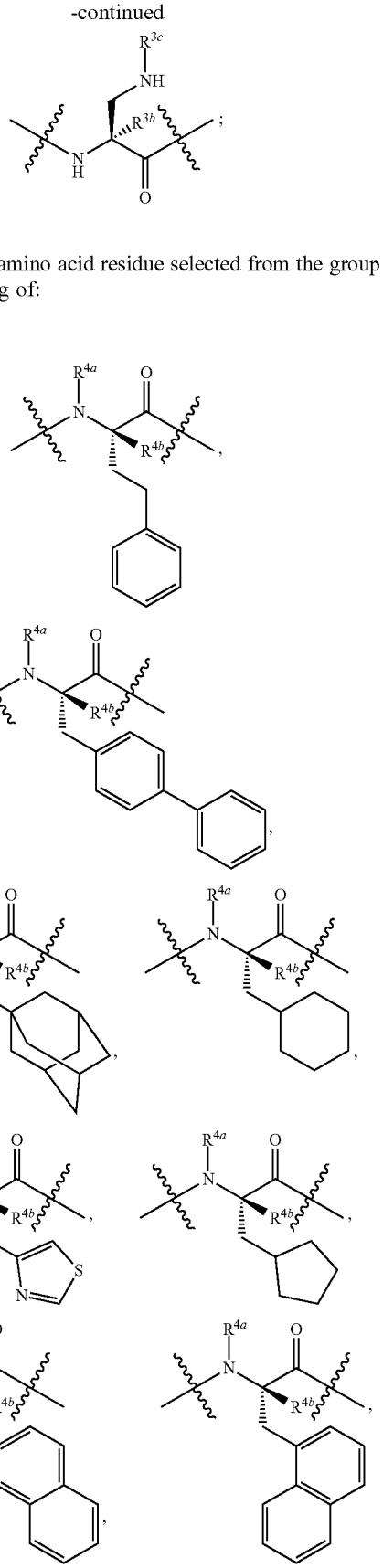
Aaa⁴ is an amino acid residue selected from the group consisting of:

-continued

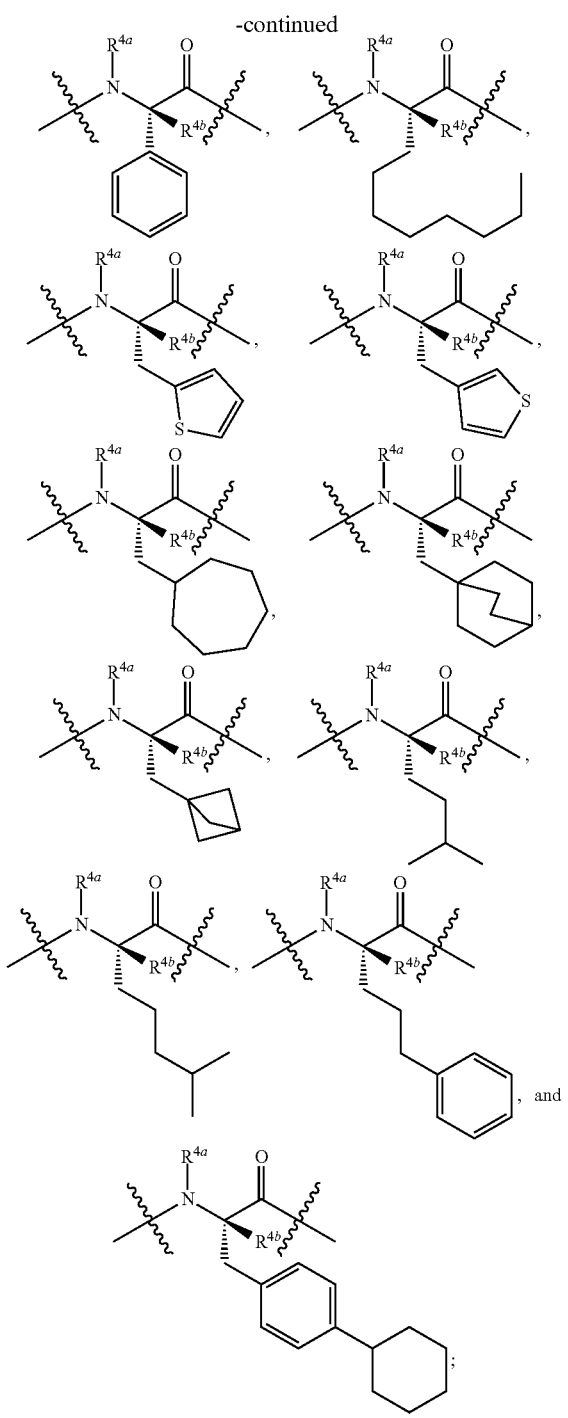

$R^{1a}$, $R^{1b}$, $R^{1e}$, $R^{1x}$, $R^{2a}$, $R^{2b}$, $R^{3a}$, $R^{3b}$, $R^{3c}$, $R^{4a}$, and $R^{4b}$ are each independently selected from the group consisting of H, methyl, ethyl, propyl, cyclopropyl, cyclobutyl, and $(C_1\text{-}C_6)$alkyl; or $R^{1a}$ and $R^{1x}$ together with the N atom to which they are attached form a 4-6-membered heterocyclyl; and $R^a$, $R^b$, $R^{1c}$ and $R^{1d}$ are each independently selected from the group consisting of H, methyl, ethyl, propyl, cyclopropyl, cyclobutyl, $(C_1\text{-}C_6)$alkyl, $C(O)((C_1\text{-}C_6)$alkyl), $C(O)((C_1\text{-}C_6)$haloalkyl), $C(O)O((C_1\text{-}C_6)$alkyl), and $C(O)O(aryl(C_1\text{-}C_6)$alkyl); or $R^a$ and $R^b$ together with the N atom to which they are attached form a 4-6-membered heterocyclyl.

2. The compound of claim 1, wherein $R^{1a}$ and $R^{1x}$ are independently H, methyl, ethyl, propyl, cyclopropyl, or cyclobutyl; or $R^{1a}$ and $R^{1x}$ together with the N atom to which they are attached form a 4-6-membered heterocyclyl.

3. The compound of claim 1, wherein $Aaa^1$ is selected from the group consisting of

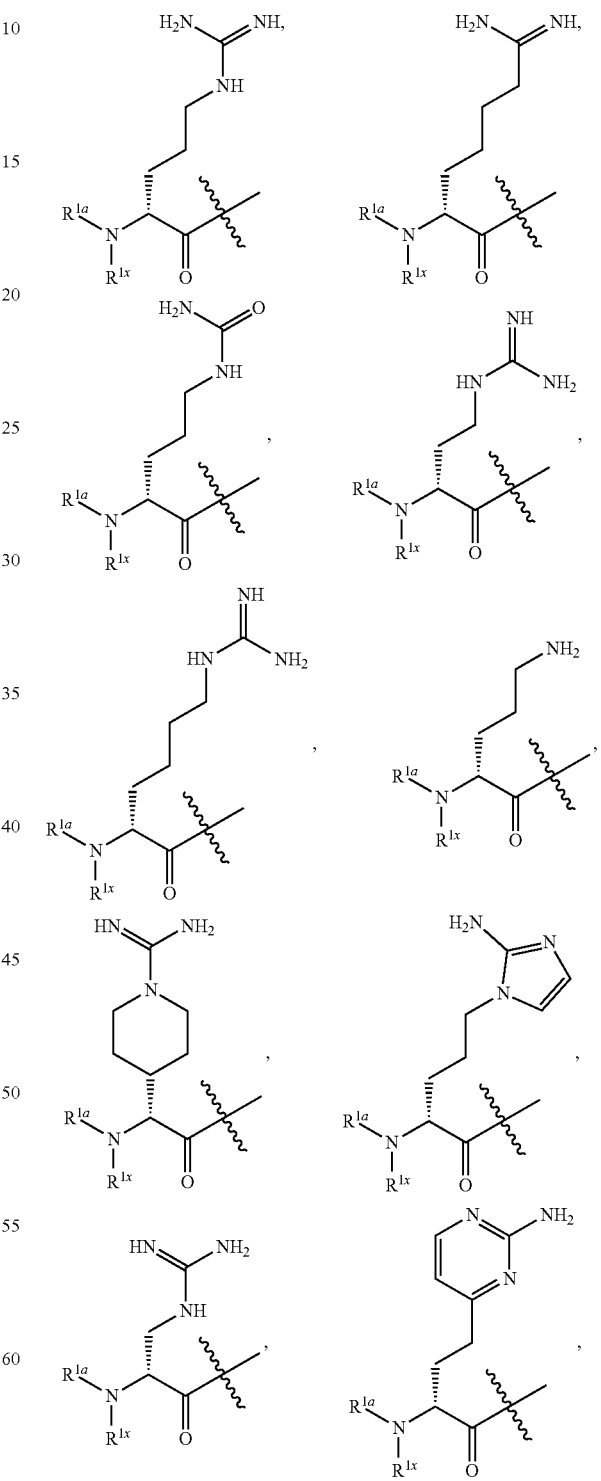

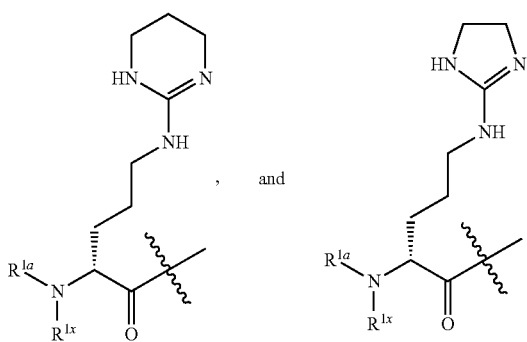
4. The compound of claim 1, wherein Aaa[1] is
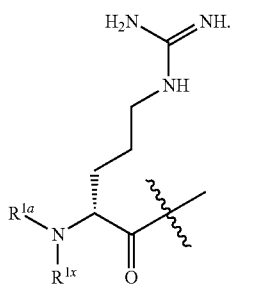
5. The compound of claim 1, wherein Aaa[1] is an amino acid residue selected from the group consisting of:
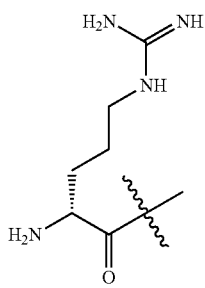 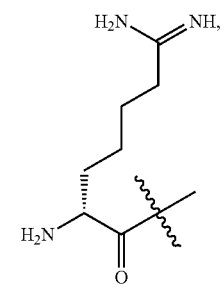
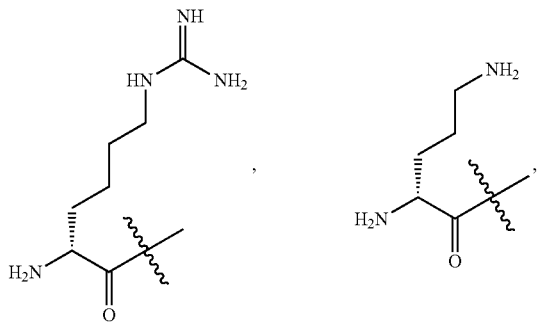
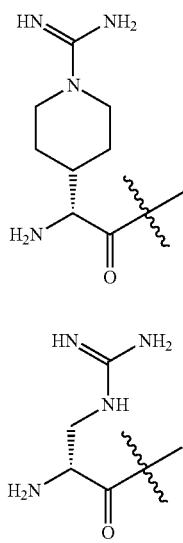 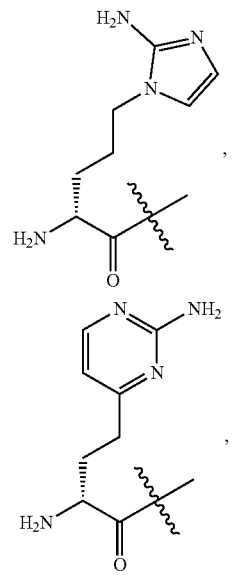
6. The compound of claim 5, wherein Aaa[1] is
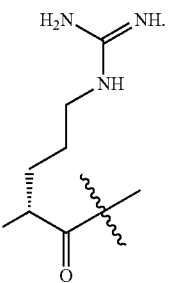
7. The compound of claim 1, wherein Aaa[2] is selected from the group consisting of:

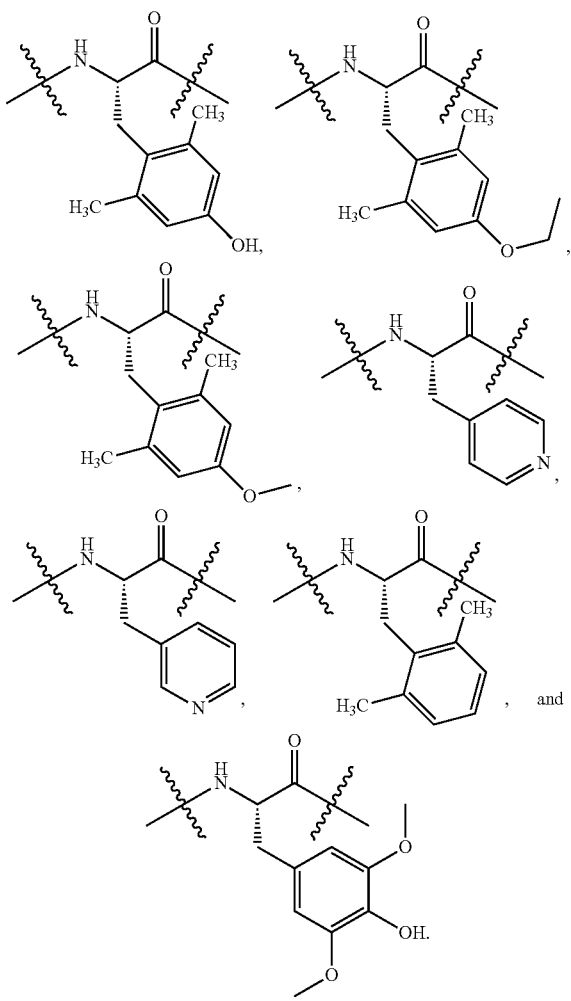
8. The compound of claim 1, wherein Aaa² is
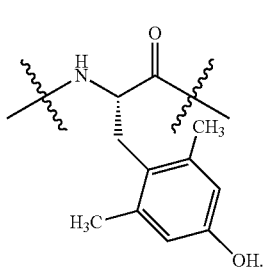 [SMILES: *N[C@@H](Cc1c(C)cc(O)cc1C)C(*)=O]
9. The compound of claim 1, wherein R³ᵇ is H or methyl.
10. The compound of claim 1, wherein Aaa³ is selected from the group consisting of:
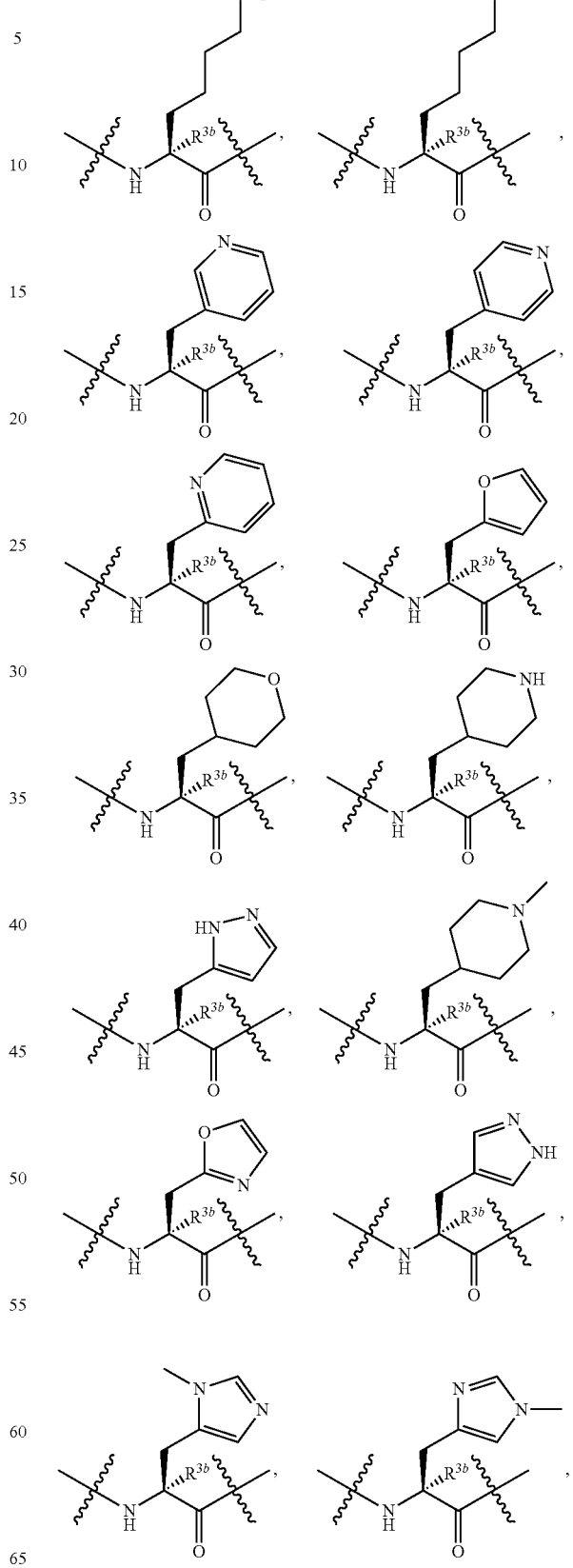

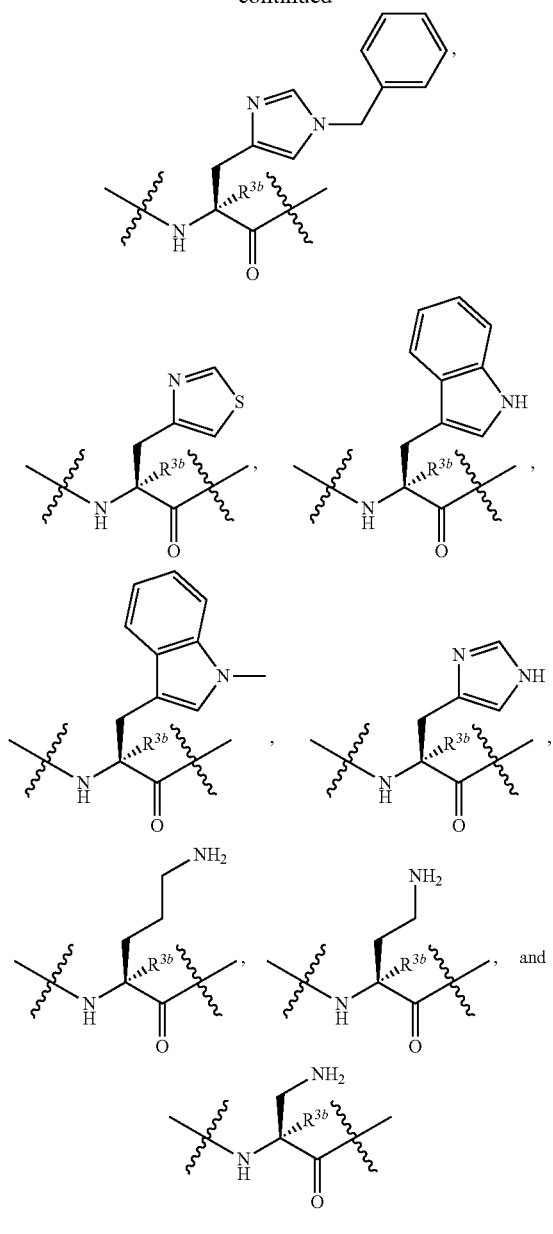
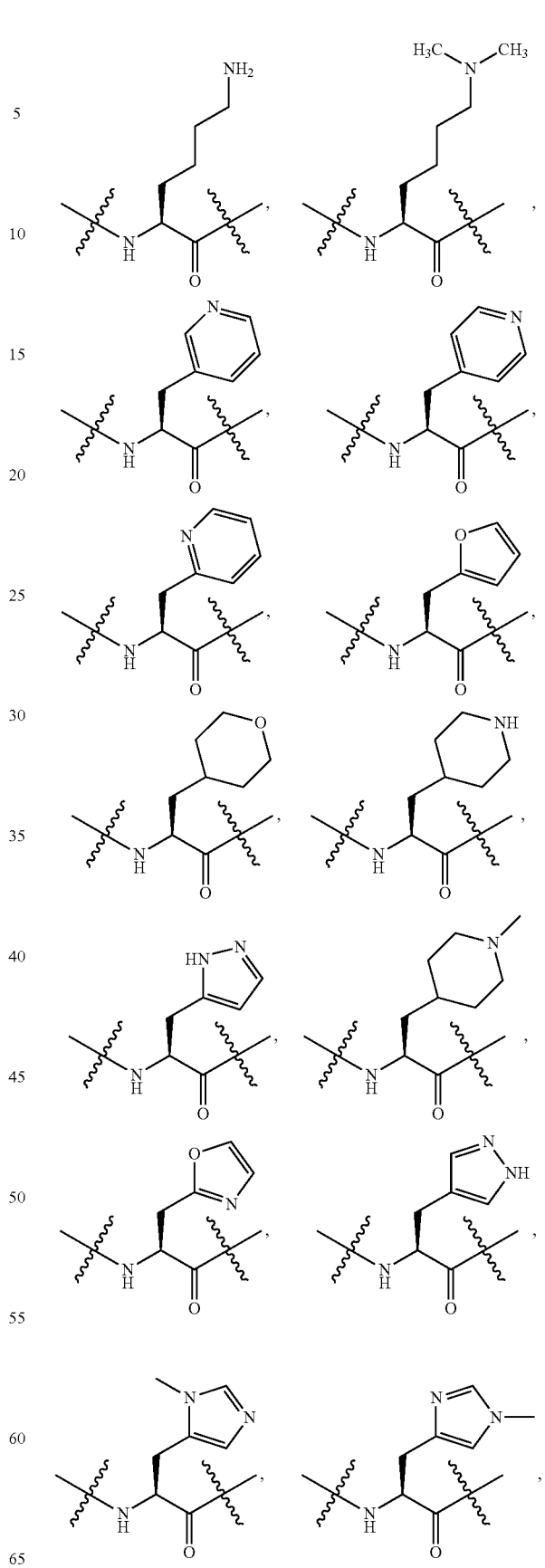
11. The compound of claim 1, wherein Aaa³ is
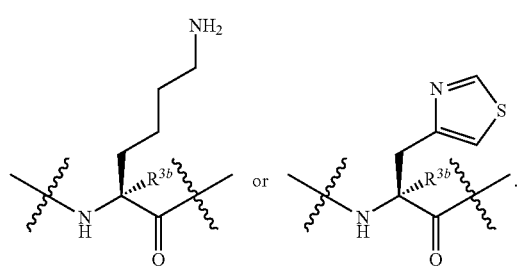
12. The compound of claim 1, wherein Aaa³ is selected from the group consisting of:

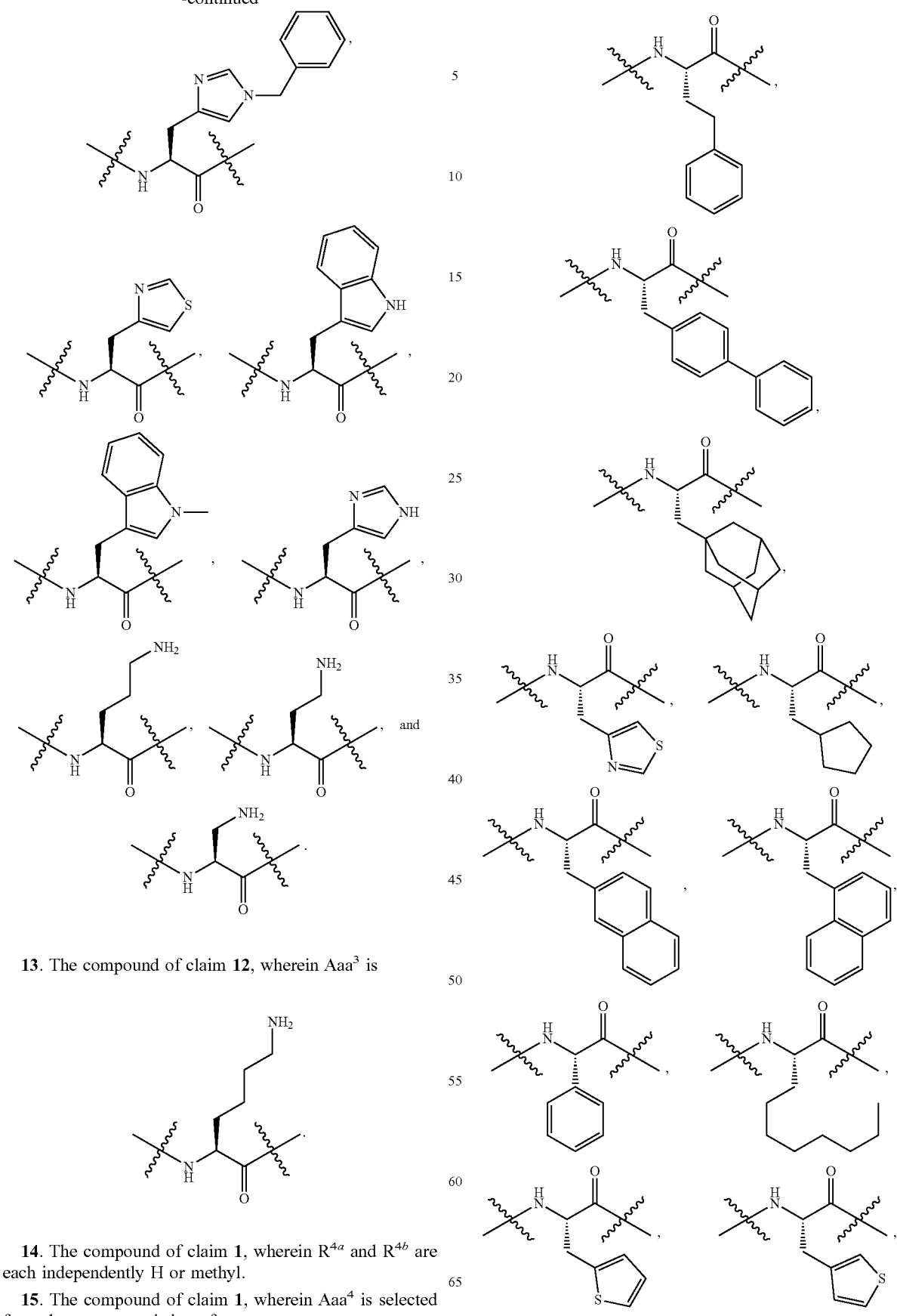
13. The compound of claim 12, wherein Aaa³ is
14. The compound of claim 1, wherein $R^{4a}$ and $R^{4b}$ are each independently H or methyl.
15. The compound of claim 1, wherein Aaa⁴ is selected from the group consisting of:

-continued
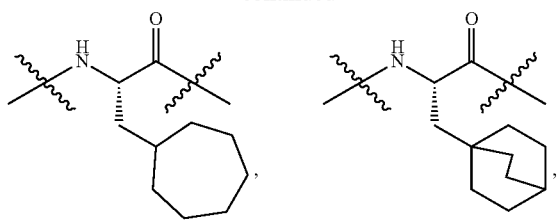
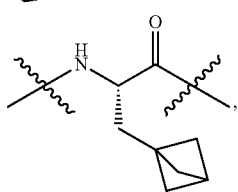
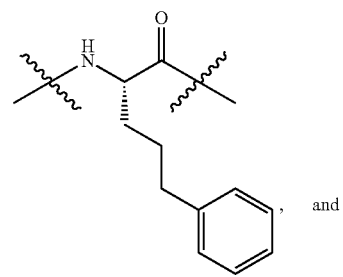
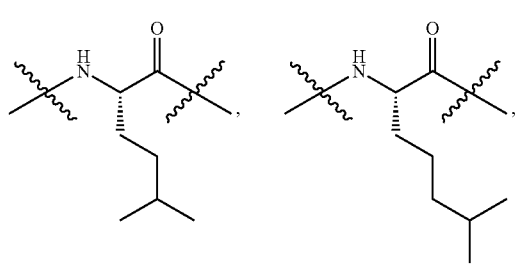 and
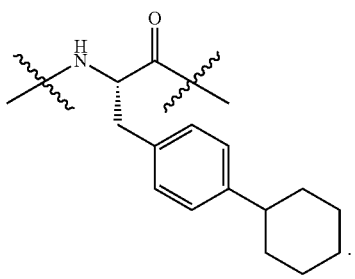
16. The compound of claim 1, wherein $R^a$ and $R^b$ are each independently H or methyl.
17. The compound of claim 16, wherein $R^a$ and $R^b$ are each H.
18. The compound of claim 1, or a pharmaceutically acceptable salt thereof, selected from the following table:
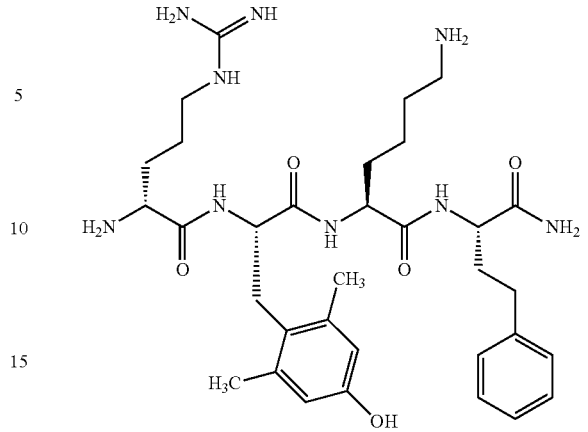
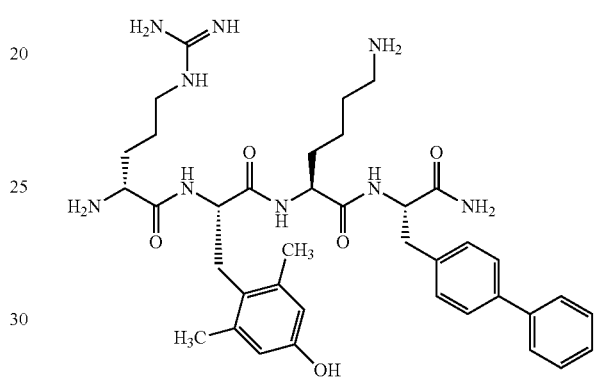
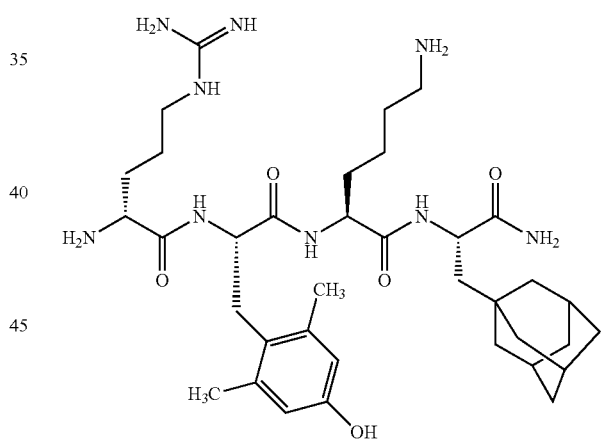
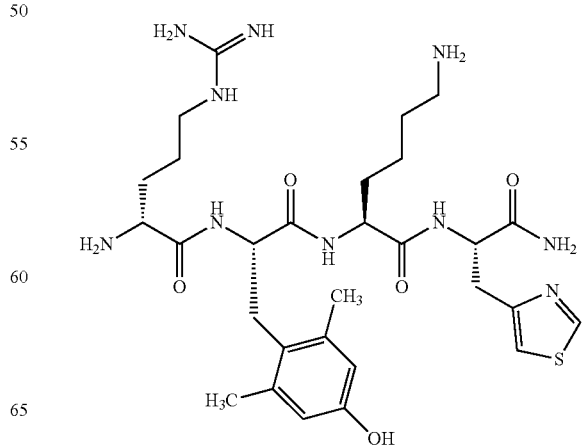

95
-continued
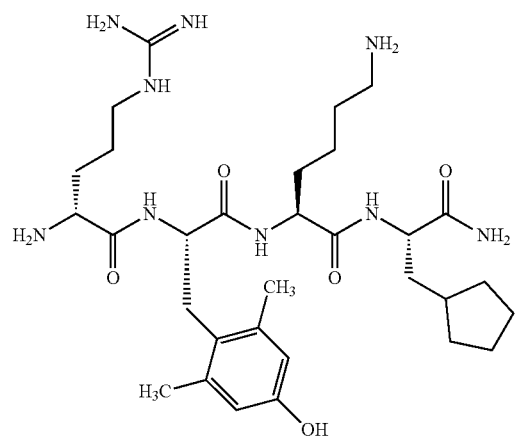 [SMILES: Cc1cc(O)cc(C)c1C[C@H](NC(=O)[C@H](N)CCCNC(=N)N)C(=O)N[C@@H](CCCCN)C(=O)N[C@@H](CC1CCCC1)C(N)=O]
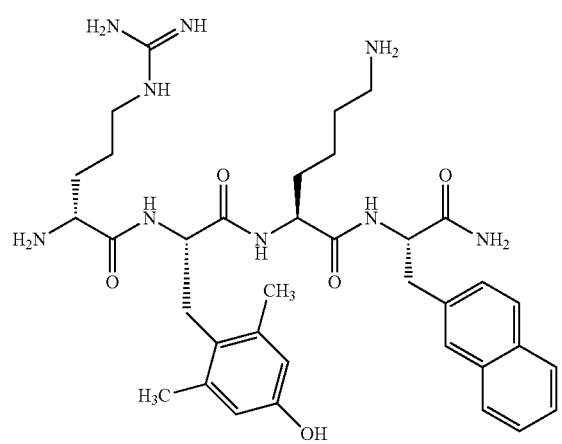 [SMILES: Cc1cc(O)cc(C)c1C[C@H](NC(=O)[C@H](N)CCCNC(=N)N)C(=O)N[C@@H](CCCCN)C(=O)N[C@@H](Cc1ccc2ccccc2c1)C(N)=O]
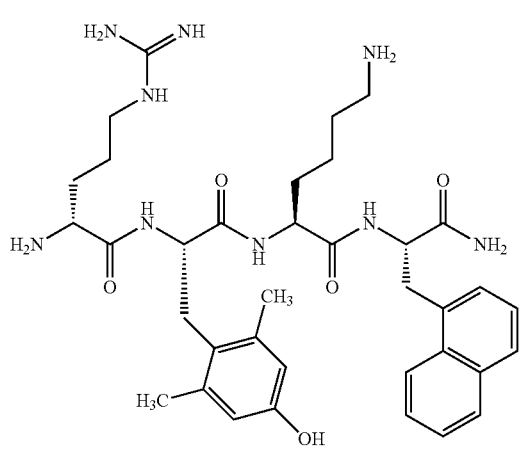 [SMILES: Cc1cc(O)cc(C)c1C[C@H](NC(=O)[C@H](N)CCCNC(=N)N)C(=O)N[C@@H](CCCCN)C(=O)N[C@@H](Cc1cccc2ccccc12)C(N)=O]
96
-continued
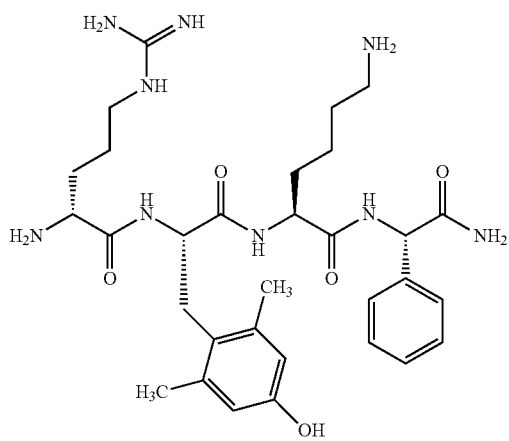 [SMILES: Cc1cc(O)cc(C)c1C[C@H](NC(=O)[C@H](N)CCCNC(=N)N)C(=O)N[C@@H](CCCCN)C(=O)N[C@H](C(N)=O)c1ccccc1]
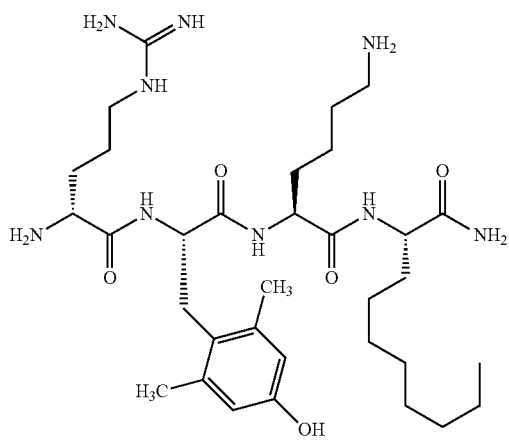 [SMILES: CCCCCCCC[C@H](NC(=O)[C@H](CCCCN)NC(=O)[C@H](Cc1c(C)cc(O)cc1C)NC(=O)[C@H](N)CCCNC(=N)N)C(N)=O]
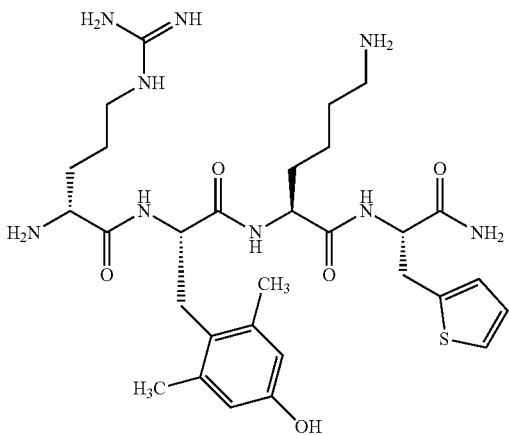 [SMILES: Cc1cc(O)cc(C)c1C[C@H](NC(=O)[C@H](N)CCCNC(=N)N)C(=O)N[C@@H](CCCCN)C(=O)N[C@@H](Cc1cccs1)C(N)=O]

97
-continued
98
-continued
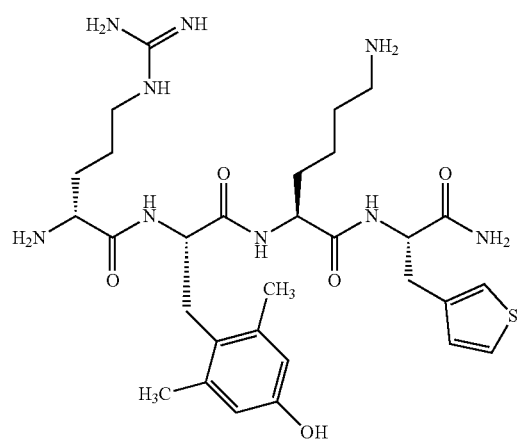 [SMILES: Cc1cc(O)cc(C)c1C[C@H](NC(=O)[C@H](N)CCCNC(=N)N)C(=O)N[C@@H](CCCCN)C(=O)N[C@@H](Cc1ccsc1)C(N)=O]
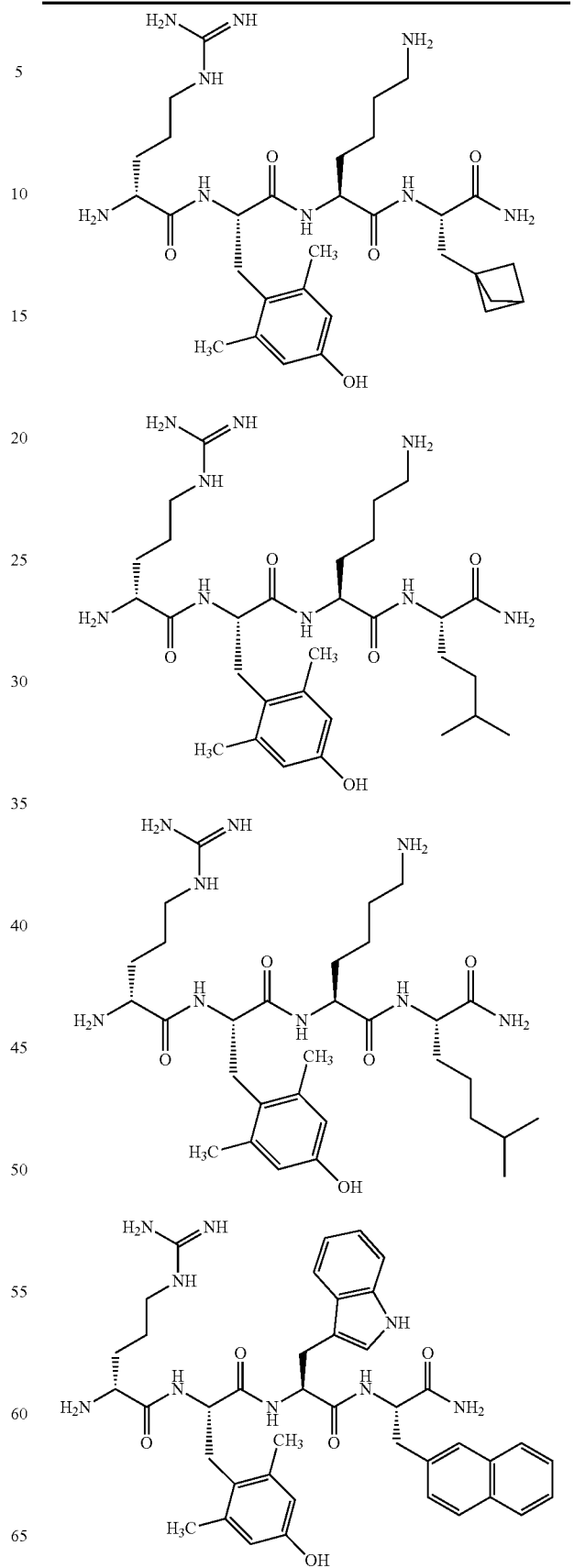

99
-continued
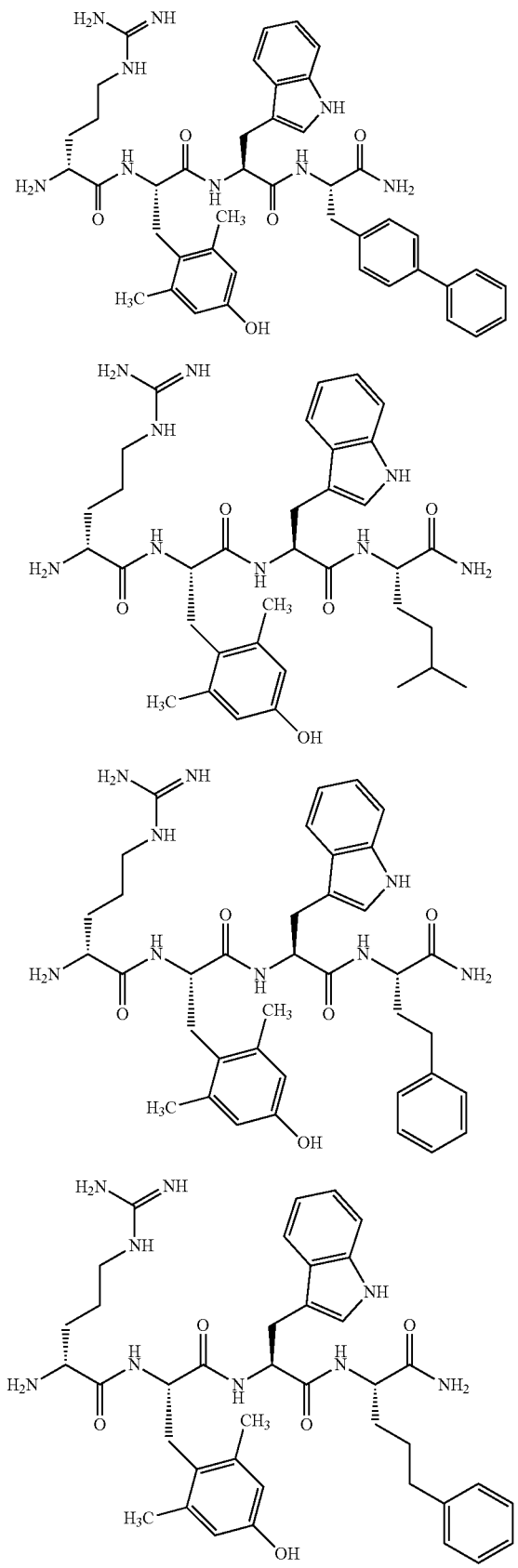
100
-continued
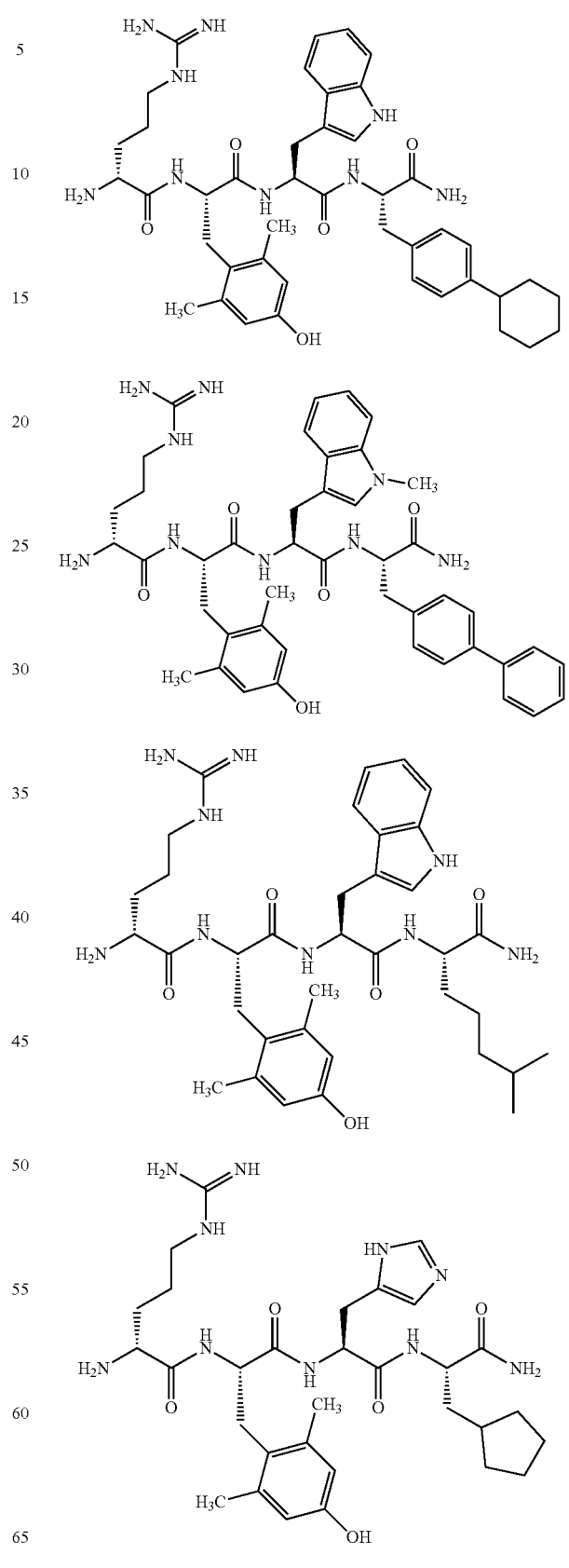

| 101 | 102 |
|---|---|
| -continued | -continued |
| 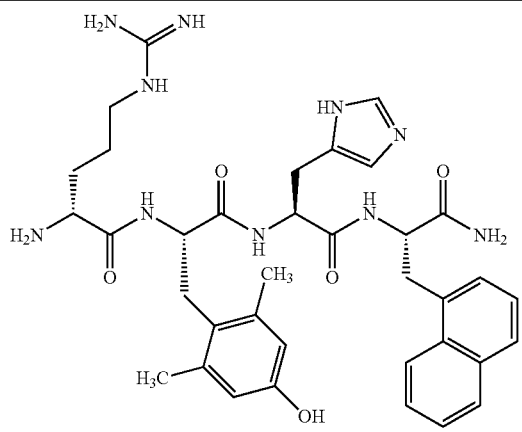 | 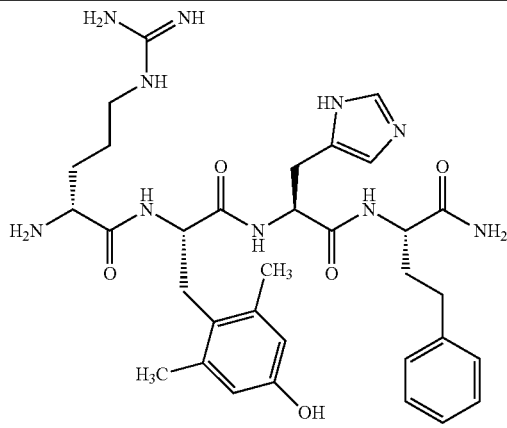 |
| 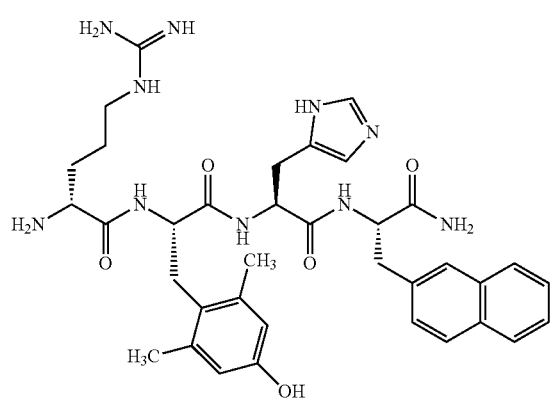 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](Cc1ccc2ccccc2c1)C(N)=O] | 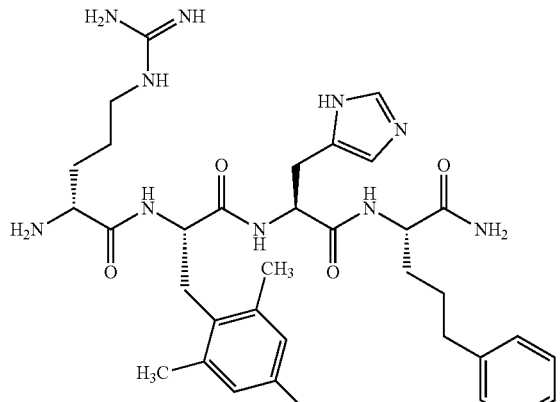 |
| 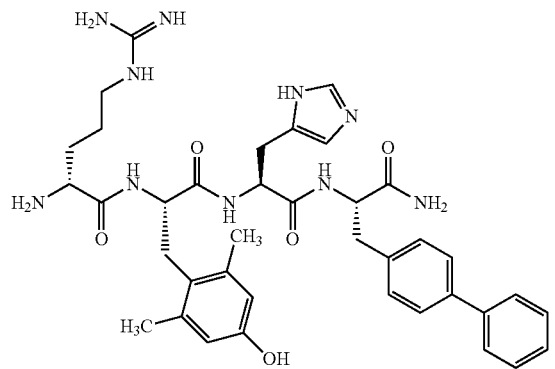 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](Cc1ccc(-c2ccccc2)cc1)C(N)=O] | 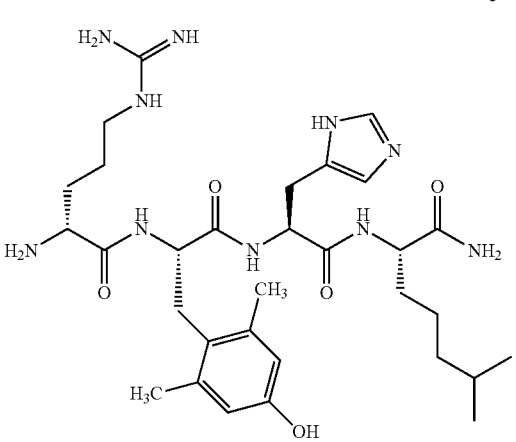 |
| 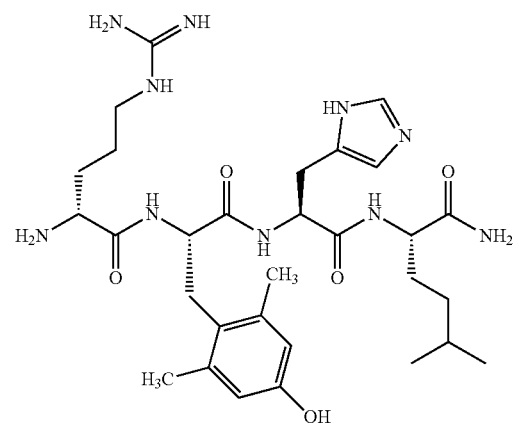 [SMILES: Cc1cc(O)cc(C)c1C[C@H](NC(=O)[C@H](N)CCCNC(=N)N)C(=O)N[C@@H](Cc1cnc[nH]1)C(=O)N[C@@H](CCC(C)C)C(N)=O] | 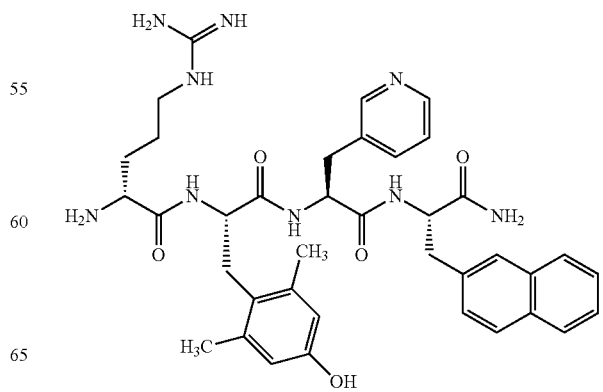 |

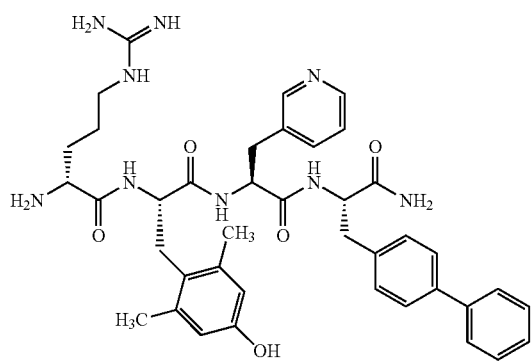 [SMILES: Cc1cc(O)cc(C)c1C[C@H](NC(=O)[C@H](N)CCCNC(=N)N)C(=O)N[C@@H](Cc1cccnc1)C(=O)N[C@@H](Cc1ccc(-c2ccccc2)cc1)C(N)=O]
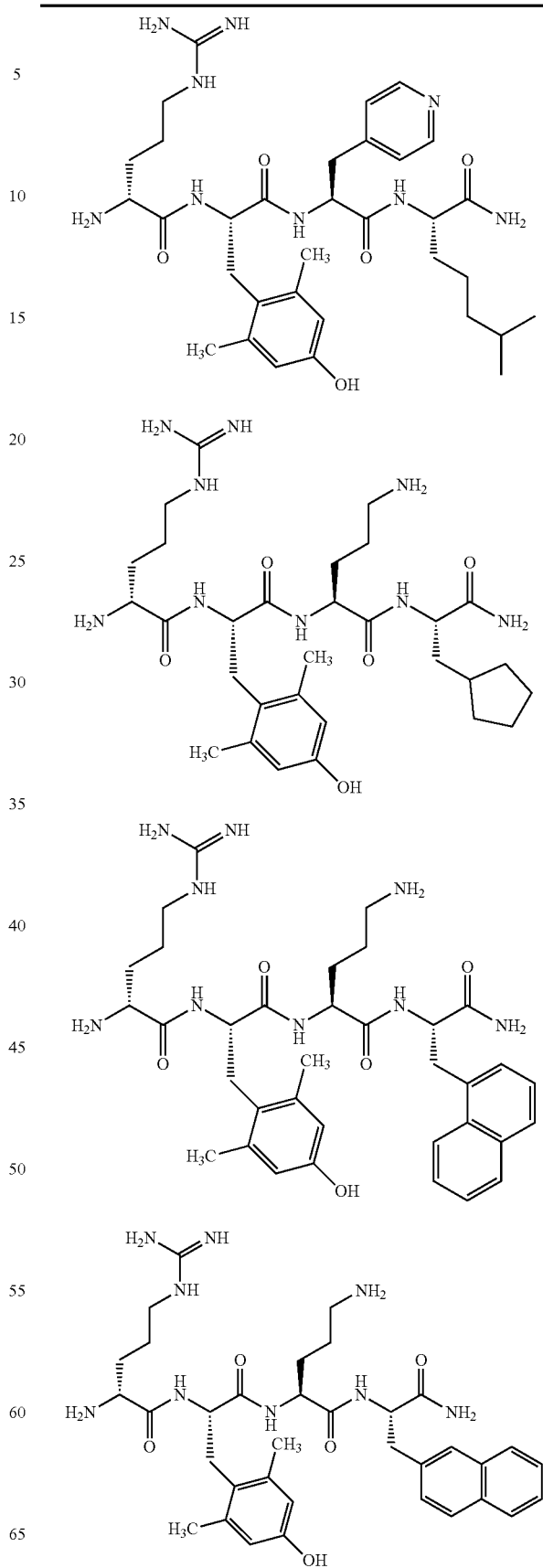

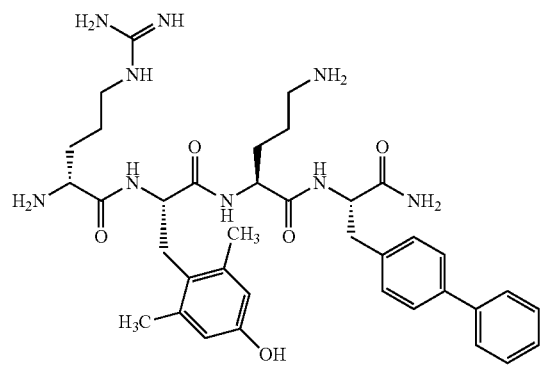 [SMILES: Cc1cc(O)cc(C)c1C[C@H](NC(=O)[C@H](N)CCCNC(=N)N)C(=O)N[C@@H](CCCN)C(=O)N[C@@H](Cc1ccc(-c2ccccc2)cc1)C(N)=O]

19. A pharmaceutical composition, comprising a compound of claim 1; and a pharmaceutically acceptable carrier.

20. The compound of claim 1, or a pharmaceutically acceptable salt thereof, represented by:

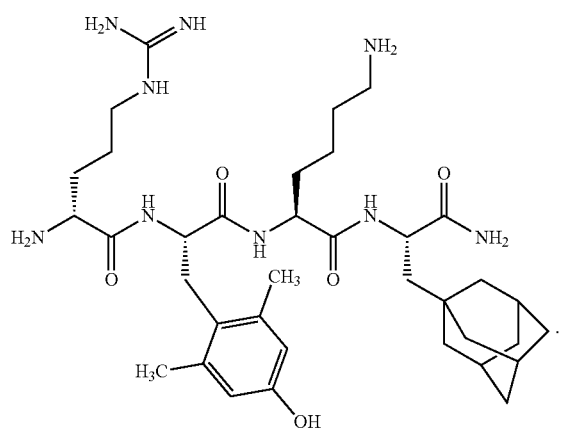 [SMILES: Cc1cc(O)cc(C)c1C[C@H](NC(=O)[C@H](N)CCCNC(=N)N)C(=O)N[C@@H](CCCCN)C(=O)N[C@@H](CC12CC3CC(CC(C3)C1)C2)C(N)=O]

21. A pharmaceutical composition, comprising a compound of claim 20 and a pharmaceutically acceptable carrier.

22. The compound of claim 1, wherein $Aaa^4$ is selected from the group consisting of:

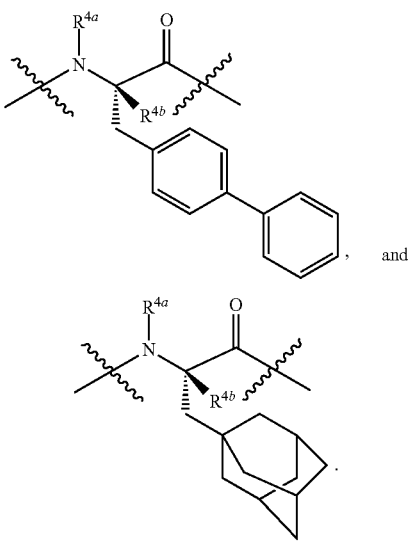

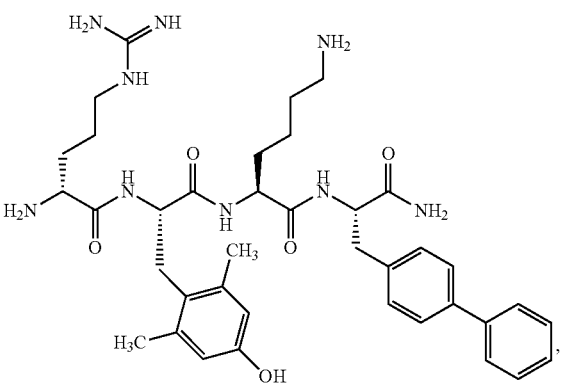

23. A pharmaceutical composition, comprising a compound of claim 22; and a pharmaceutically acceptable carrier.

24. The compound of claim 1, or a pharmaceutically acceptable salt thereof, represented by:

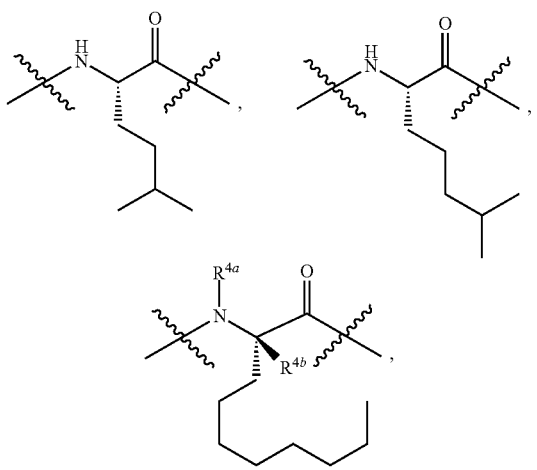

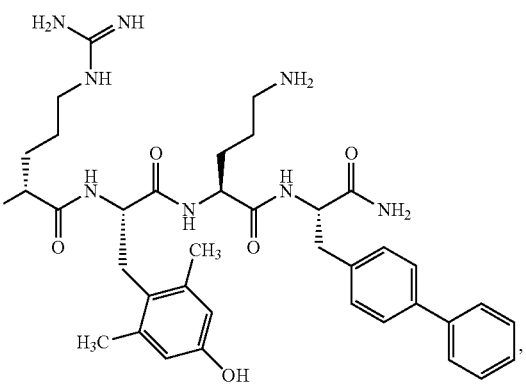

107
-continued
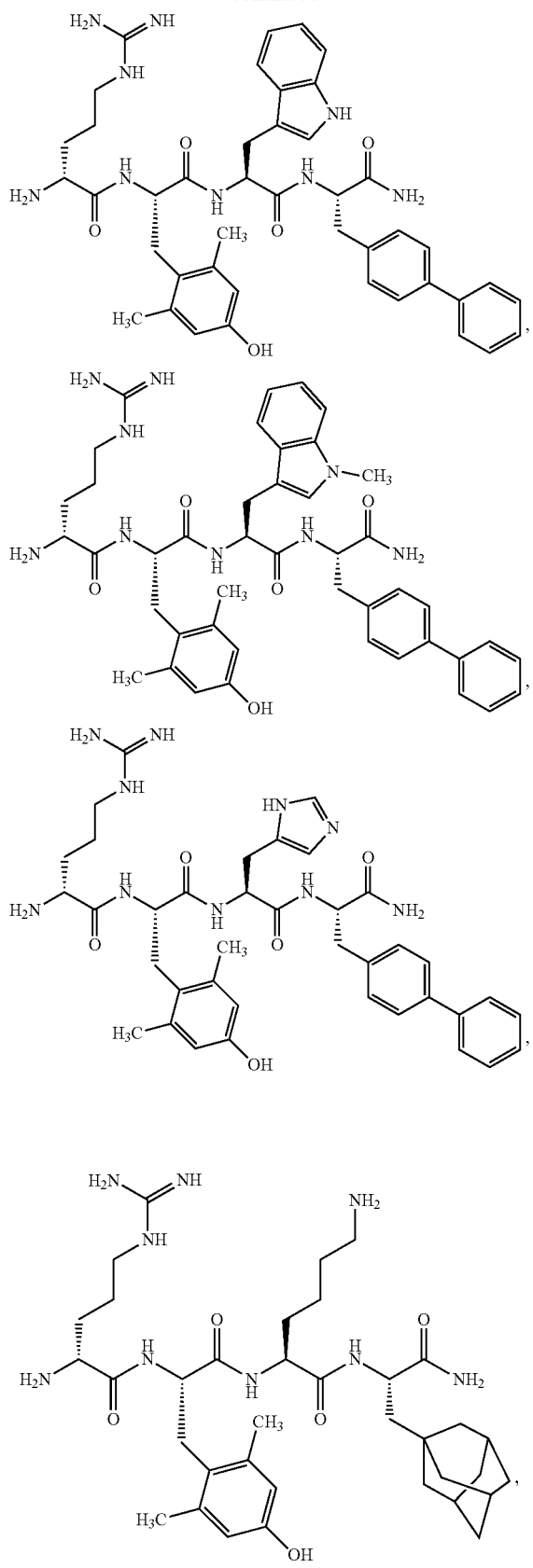
108
-continued
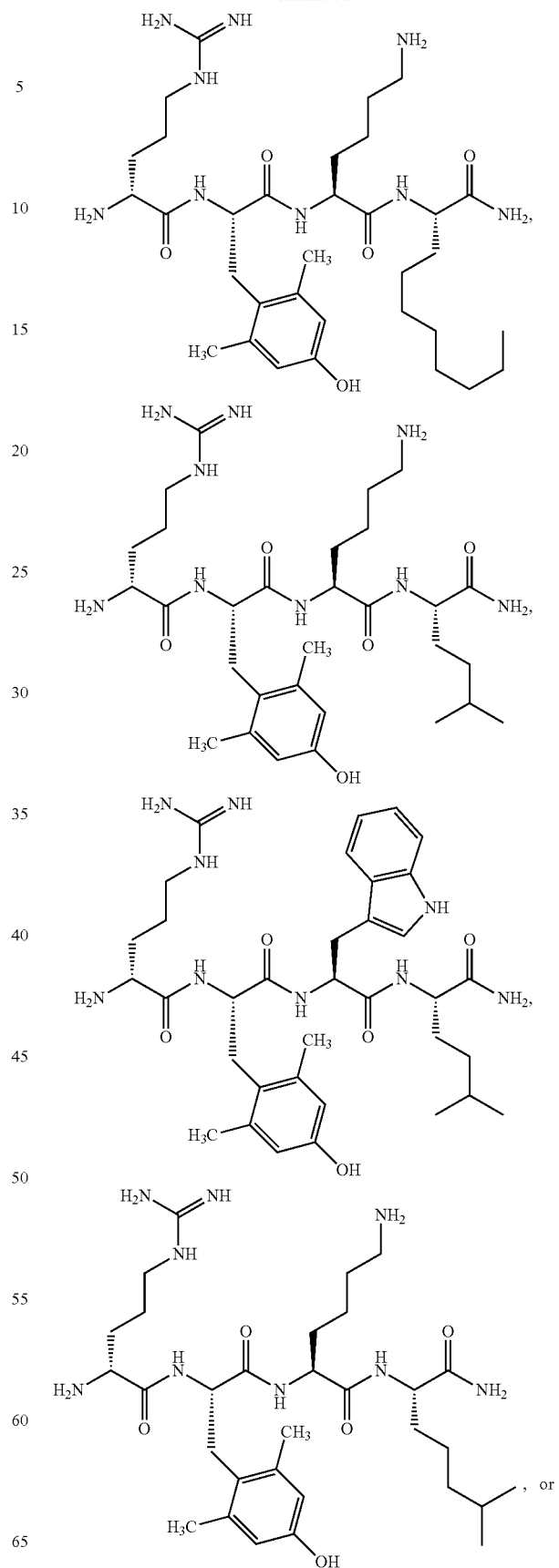

-continued
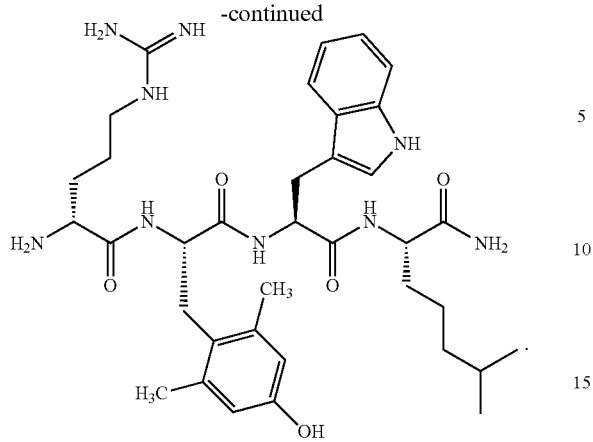
25. A pharmaceutical composition, comprising a compound of claim 24; and a pharmaceutically acceptable carrier.

UNITED STATES PATENT AND TRADEMARK OFFICE
CERTIFICATE OF CORRECTION

| | | |
|---|---|---|
| PATENT NO. | : 12,252,554 B2 | Page 1 of 2 |
| APPLICATION NO. | : 17/414168 | |
| DATED | : March 18, 2025 | |
| INVENTOR(S) | : Guozhu Zheng et al. | |

It is certified that error appears in the above-identified patent and that said Letters Patent is hereby corrected as shown below:

In the Claims

In Claim 1, at Column 82, Line 1-10, please replace:

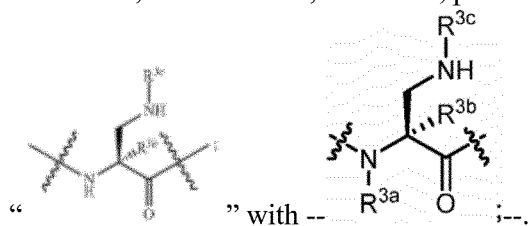

In Claim 1, at Column 82, Line 37-45, please remove the following structure:

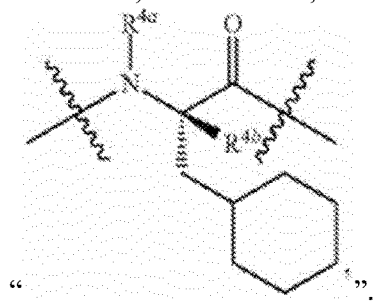

In Claim 3, at Column 84, Line 10-20, please replace:

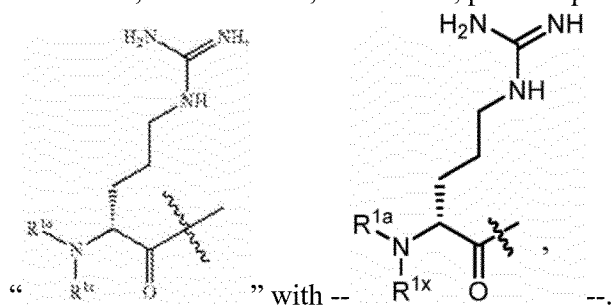

Signed and Sealed this
Eighteenth Day of November, 2025

John A. Squires
*Director of the United States Patent and Trademark Office*

CERTIFICATE OF CORRECTION (continued)
U.S. Pat. No. 12,252,554 B2

In Claim 4, at Column 85, Line 20-30, please replace:

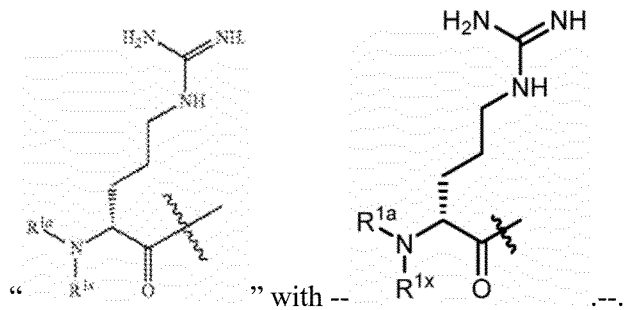

" with --                      .--.

In Claim 5, at Column 85, Line 40-49, please replace:

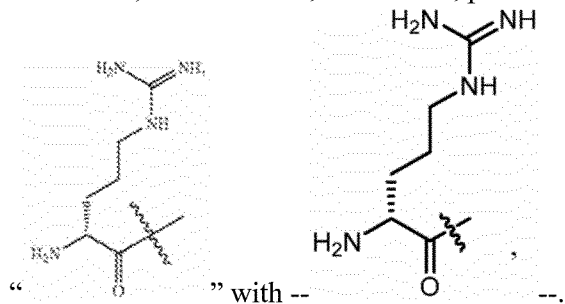

" with --                      .--.

In Claim 6, at Column 86, Line 53-63, please replace:

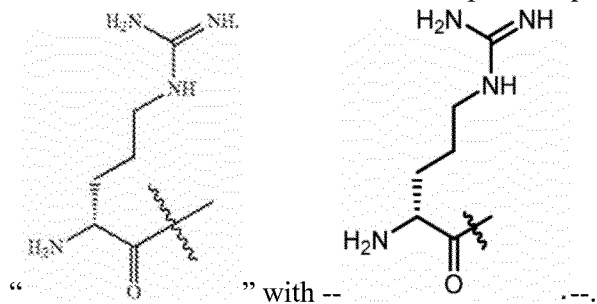

" with --                      .--.

Please add a "." at the end of Claim 10 at Column 89, Line 60.